(12) United States Patent
Benazet et al.

(10) Patent No.: US 9,169,246 B2
(45) Date of Patent: Oct. 27, 2015

(54) PYRAZOLOQUINOLINONE DERIVATIVES, PREPARATION THEREOF AND THERAPEUTIC USE THEREOF

(75) Inventors: Alexandre Benazet, Paris (FR); Olivier Duclos, Paris (FR); Nathalie Guillo, Paris (FR); Gilbert Lassalle, Paris (FR); Karim Macary, Paris (FR); Valérie Vin, Paris (FR)

(73) Assignee: SANOFI, Paris (FR)

( * ) Notice: Subject to any disclaimer, the term of this patent is extended or adjusted under 35 U.S.C. 154(b) by 352 days.

(21) Appl. No.: 13/245,468

(22) Filed: Sep. 26, 2011

(65) Prior Publication Data

US 2013/0079337 A1    Mar. 28, 2013

(51) Int. Cl.
C07D 471/04 (2006.01)
A61K 31/551 (2006.01)
A61K 9/20 (2006.01)

(52) U.S. Cl.
CPC ............ *C07D 471/04* (2013.01); *A61K 9/2054* (2013.01)

(58) Field of Classification Search
CPC ............................ C07D 471/04; A61K 9/2054
USPC .............................................. 546/82; 514/292
See application file for complete search history.

(56) References Cited

U.S. PATENT DOCUMENTS

| | | | |
|---|---|---|---|
| 3,880,855 A | 4/1975 | Frederick et al. | |
| 8,846,694 B2 | 9/2014 | Heinrich et al. | |
| 2005/0245563 A1* | 11/2005 | Boyle et al. | 514/292 |
| 2010/0222319 A1 | 9/2010 | Bernhart et al. | |
| 2014/0235616 A1 | 8/2014 | Benazet et al. | |

FOREIGN PATENT DOCUMENTS

| | | | |
|---|---|---|---|
| DE | 102008027574 A1 | | 12/2009 |
| JP | 2006-45118 | | 2/2006 |
| JP | 2006045118 | * | 2/2006 |
| WO | 2005028474 | * | 3/2005 |
| WO | WO-2006/063167 A1 | | 6/2006 |
| WO | WO-2006/072370 A1 | | 7/2006 |
| WO | WO-2009/074749 A2 | | 6/2009 |
| WO | WO-2009/074749 A3 | | 6/2009 |
| WO | 2012033144 | * | 3/2012 |

OTHER PUBLICATIONS

JP 2006045118, Caplus, English Abstract, Feb. 2006. DN 144:212771.*
Bradshaw, Ralph A. et al., "N-Terminal processing: the methionine aminopeptidase and N-acetyl transferase families," TIBS (1998), vol. 23, pp. 263-267.
Li, Xuan et al., "Evidence That the Human Homologue of a Rat Initiation Factor-2 Associated Protein (p67) is a Methionine Aminopeptidase," Biochemical and Biophysical Research Communications (1996), vol. 227, pp. 152-159.
Wang, Jieyi et al., "Physiologically Relevant Metal Cofactor for Methionine Aminopeptidase-2 Is Manganese," Biochemistry (2003), vol. 42, pp. 5035-5042.
Li, Xuan et al., "Amino-terminal protein processing in *Saccharomyces cerevisiae* is an essential function that requires two distinct methionine aminopeptidases," Proceedings of the National Academy of Sciences (1995), vol. 92, pp. 12357-12361.
Griffith, Eric C. et al., "Methionine aminopeptidase (type 2) is the common target for angiogenesis inhibitors AGM-1470 and ovalicin," Chemistry & Biology (1997), vol. 4, pp. 461-471.
Griffith, Eric C. et al., "Molecular recognition of angiogenesis inhibitors fumagillin and ovalicin by methionine aminopeptidase 2," Proceedings of the National Academy of Sciences (1998), vol. 95, pp. 15183-15188.
Kruger, Erwin A. et al., "TNP-470: an angiogenesis inhibitor in clinical development for cancer," Expert Opinion on Investigational Drugs (2000), vol. 9, No. 6, pp. 1383-1396.
Satchi-Fainaro, Ronit et al., "Targeting angiogenesis with a conjugate of HPMA copolymer and TNP-470," Nature Medicine (2004), vol. 10, No. 3, pp. 255.
Chauncey, M. A. et al. (1990). "Reactions of Heterocyclic Quinone Methides:1-Methyl-3methylene-2,4(1H,3H)-quinolinedione," *Synthesis* 11: 1005-1007.
Docampo, M.L. et al. (2007) "Ultrasound-Promoted Reaction of 2-Chlorobenzoic Acids and Aliphatic Amines," *Eur. J. Org. Chem.* 24: 4111-4115.
Marsais, F. (1989) "Directed ortho-Lithiation of Chloroquinolines. Application to Synthesis of 2, 3-Disubstituted Quinolines," *Journal of Heterocyclic Chemistry* 26 (6): 1589-1594.
Settimo De A et al. (1970) "Reaction of indole with bromine. Substitution, oxidation, and dimerization," *Journal of Organic Chemistry* 35(8): 2546-2551.
List of Compounds Entered Into STN Database on Apr. 14, 2011, 32 Total Pages.
Wheeler, H. H. et al. (1911) "Alkylation of Aromatic Amino Acids: nitroamino and Iodamino and Iodamino acids," *American Chemical Journal* 44: 441-452.
Wyatt, P. G. (2008) "Identification of N-(4-Piperidinyl)-4-(2,6-dichlorobenzoylamino)-IH-pyrazole-3-carboxamide (AT7519), a Novel Cyclin Dependent Kinase Inhibitor Using Fragment-Based X-Ray Crystallography and Structure Based Drug Design," *J. Med. Chem.* 51: 4986-4999.
Zhao, J. et al. (2007) "Synthesis of Xanthones, Thioxanthones, and Acridones by the Coupling of Arynes and Substituted Benzoates," *J. Org. Chem.* 72 (2): 583-588.
International Search Report mailed on Feb. 15, 2013, for PCT Patent Application No. PCT/EP2012/068786, filed on Sep. 24, 2012, seven pages.

* cited by examiner

Primary Examiner — Rita Desai
(74) Attorney, Agent, or Firm — Morrison & Foerster LLP

(57) ABSTRACT

The invention relates to compounds corresponding to formula (I)

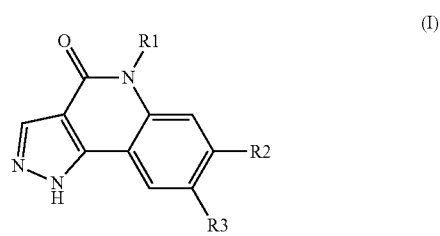

in which R1, R2 and R3 are as defined in Claim 1, and also to the process for preparing them and to their therapeutic use.

14 Claims, No Drawings

PYRAZOLOQUINOLINONE DERIVATIVES, PREPARATION THEREOF AND THERAPEUTIC USE THEREOF

The present invention relates to pyrazoloquinolinone derivatives, to their preparation and to their therapeutic use.

The compounds according to the present invention are reversible and selective inhibitors of type-2 methionine aminopeptidase (MetAP2).

MetAP2 is a ubiquitous cytosol-based metalloprotease involved in polypeptide catabolism.

MetAP2 catalyses the cleavage of methionine residues located at the N-terminal end of proteins newly synthesized by the cell (Bradshaw R. A. et al., *TIBS*, 1998, 23, 263-267). Cleavage of the N-terminal methionine residues is an important step in the maturation of many proteins and polypeptides. It enables the cell to continue the usual post-translational modifications (myristoylation, palmitoylation, etc.), and then to degrade these same proteins. However, MetAP2 can only cleave this residue on condition that the second residue is of smaller size and uncharged.

MetAP2 is active when the active site contains two divalent metal atoms such as Co(II) or Mn(II) (Li X., Chang Y. H., *Biochem. Biophys. Res. Commun*, 227, 1996, 152-159). Studies have moreover made it possible to establish that human MetAP2 quite probably uses manganese as physiological metal ion (Wang J. et al., *Biochemistry* 2003, 42, 5035-5042).

Another function of MetAP2 is combination with a protein translation factor, eIF2 (eukaryotic initiation factor 2), thus preventing its phosphorylation (Datta et al., 1988; Li and Chang, 1996). It has been shown that the phosphorylation of eIF2 results in inhibition of overall protein synthesis in eukaryotic cells. By binding to eIF2, MetAP2 protects the phosphorylation site (Datta, 2000; Kimball, 1999; Pestova et al., 2001). However, inhibitors of MetAP2 activity do not affect the capacity of MetAP2 to block the phosphorylation of eIF2 (Griffith, 1997), which suggests that the two functions are independent.

A MetAP2 isoform exists: MetAP1. These two isoforms are distinguished by the presence of an additional helical domain of about 60 residues within the C-terminal domain of MetAP2. Eukaryotes possess the two forms. A mutation of the two forms is lethal to the eukaryotic cell. This result underlines the interest in identifying inhibitors that are selective towards MetAP2. On the other hand, when only one isoform is mutated, growth reduction is observed (Li X. and Chang Y. H., *Proc. Natl. Acad. Sci.* 1995, 92, 12357-12361). These results confirm that methionine aminopeptidase (MAP) function is essential for cell growth and this activity cannot be relayed by a route independent of MetAPs.

Two types of MetAP2 inhibitor also exist: reversible inhibitors and irreversible inhibitors. Certain known irreversible inhibitors are fumagillin, TNP-470 and ovalicin. At the molecular level, TNP-470, just like fumagillin and ovalicin, binds covalently and irreversibly to MetAP2 (Griffith E. C. et al., *Chem. Biol.* 1997, 4, 461-471).

MetAP2 has been identified as being the target of a family of anti-angiogenic agents derived from fumagillin, described as powerful irreversible MetA2 inhibitors. The causal link between the inhibition of MetAP2 and the resulting inhibition of endothelial cell proliferation and of neovascularization is clearly established (Griffith E. C. et al., *Chem. Biol.* 1998, 95, 15183-15188).

At the cellular level, the target proteins of MetAP2 are still at the present time very scarcely known. One of them is glyceraldehyde-3-phosphate dehydrogenase. A defect in the synthesis of this enzyme has been observed during treatment of endothelial cells with TNP-470. Recent studies support the hypothesis that the anti-MetAP2 activity of TNP-470 is the source of its anti-angiogenic activity.

It has been shown that irreversible MetAP2 inhibitors play a role in the treatment of pulmonary and hepatic fibroses. Fibrosis is the abnormal formation of scar tissues following a tissue lesion and leads to chronic and progressive impairment of the affected organs, which may result in serious dysfunction of the affected organ. Many causes of fibrosis may exist, but in the majority of cases the cause of the affliction remains unknown and the lesions are difficult to detect. Aggregates of activated fibroblasts and myofibroblasts develop, which constitute the start of numerous fibrotic foci. When the lesions are formed, they are irreversible and cannot be eliminated. Treatments are thus directed towards slowing down the evolution of the complaint and of improving the symptoms. In this context, irreversible MetAP2 inhibitors have shown on in vivo models a reduction of pulmonary and hepatic fibrosis. However, substantial toxicity of these irreversible inhibitors has been demonstrated (Kruger E. A., *Exp. Opinion Invest. Drugs*, 2000; Satchi-Fainaro R. et al., *Nature Medicine*, 2004).

One subject of the present invention is compounds corresponding to formula (I)

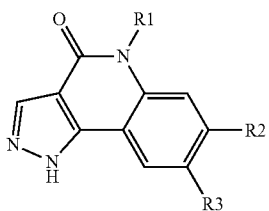

(I)

in which:
R1 represents:
  —(C1-C4)alkyl
  —(C1-C4) haloalkyl
R2 represents:
  a group:

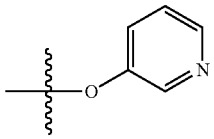 [SMILES: *Oc1cccnc1]

a group:

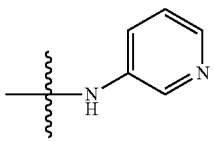 [SMILES: *Nc1cccnc1]

a group: -A—X
R3 represents:
  —H
  halogen
  —(C1-C6)alkyl
  a cyano group
  —CO₂H
  —CONH₂

A represents:
  an aryl or heteroaryl group
X is absent or represents:
  halogen
  a cyano group
  an oxo group
  —(CH₂)ₙOH
  -(C1-C6) haloalkyl
  —(C1-C6)alkyl
  —(C1-C6)alkoxy
  —CHOH-aryl
  heterocycle
  heteroaryl
  —(C1-C6)alkyl-heterocycle
  —(C1-C6)alkyl-heteroaryl
  —(C1-C6)alkyl-COORa
  —(C1-C6)alkyl-NRaRb
  -heteroaryl-(CH₂)n-NRaRb
  (CH2)n-NRa—C(O)—Rb
  —NRaRb
  —NRa—(CH2)n-O—Rb
  —NRa-heterocycle
  —NRa-aryl
  —NRa—C(O)—(CH2)n-NRaRb
  —NRaC(O)—(C1-C6)alkyl
  —NRa—C(O)—(C1-C6)alkyl-aryl
  —NRa—C(O)—(CH2)n-O—Rb
  —NRa—SO2-(CH2)n-aryl
  —NRa—SO2-(CH2)n-NRaRb
  —NRa—SO2-Rb
  —NRa—SO2-aryl-O-aryl
  —NRa—SO2-aryl-(CH2)n-NRb—C(O)—Rb
  —COORa
  —CONRaRb
  —C(O)—NRa—(CH2)n-O—Rb
  —C(O)—NRa-aryl-C(O)—NRaRb
  —C(O)—NRa—(CH2)n-NRaRb
  —C(O)—NRa—(CH2)n-heteroaryl
  —O—(CH2)n-NRaRb
  —O-heterocycle
  —CO-heterocycle
  —CO-heteroaryl
  —SO2NRaRb
  —SO2-heterocycle
Ra and Rb represent, independently:
  —H
  —(C1-C6)alkyl
    n represents 0, 1, 2 or 3.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of tautomers. These tautomeric forms form part of the invention.

The compounds of formula (I) may exist in the form of bases or salified with acids or bases, especially pharmaceutically acceptable acids or bases. Such addition salts form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates, i.e. in the form of associations or combinations with one or more water molecules. Such hydrates also form part of the invention.

In the context of the present invention, and unless otherwise mentioned in the text, the following definitions apply:

a halogen atom: a fluorine, a chlorine, a bromine or an iodine;

an alkyl group: a linear, branched or cyclic saturated aliphatic group. The alkyl group may be substituted with one or more alkoxy groups. Examples that may be mentioned include methyl, ethyl, propyl, isopropyl, cyclopropyl, cyclobutyl, oyclopentyl, cyclohexyl, etc. groups;

an alkoxy group: a radical —O-alkyl in which the alkyl group is as defined previously; an example that will be mentioned is methoxy;

a haloalkyl group: an alkyl group as defined above substituted with 1 to 5 halogen atoms, as defined previously. Examples that will be mentioned are trifluoromethyl, trifluoroethyl, etc. groups;

a cyano group: a group CN;

an oxo group: a radical containing a double-bonded oxygen atom in the form =O; this group may substitute an aryl, heteroaryl or heterocyclic group as in the following example:

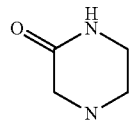

an aryl group: a cyclic aromatic group comprising between 5 and 10 carbon atoms, this group possibly being fused with a heterocycle such as a morpholine (compound 56). An example of an aryl group that may be mentioned is the phenyl group; the aryl group may be substituted with one or more halogen atoms or (C1-C6)alkyl, (C1-C6) alkoxy, NRaRb, OH, C(O)—(C1-C6)alkyl or oxo groups;

a heteroaryl group: a cyclic aromatic group comprising between 5 and 10 carbon atoms and comprising between 1 and 5 heteroatoms, such as nitrogen, oxygen or sulfur. The heteroaryl group may comprise an N-oxide group. Examples of heteroaryl groups that may be mentioned include pyridine, 2-pyridyl, 4-pyridyl, 3-pyridyl, pyrazole, thiophene, indole, pyrimidine, imidazole, furan, indazole, tetrazole, benzoxazine, oxazole, quinoline, triazole and oxadiazole groups; the heteroaryl group may be substituted with one or more halogen atoms or (C1-C6)alkyl, (C1-C6)alkoxy, NRaRb, OH, C(O)—(C1-C6)alkyl or oxo groups;

a heterocycle: an optionally bridged cyclic alkyl group comprising from 4 to 9 atoms forming this ring, 1 or 2 of which are heteroatoms, such as oxygen, nitrogen or sulfur. Mention may be made especially of pyrrolidine, piperazine, piperidine, morpholine, oxazepane, diazepane and azetidine groups; the heterocyclic group may be substituted with one or more halogen atoms or (C1-C6)alkyl, (C1-C6)alkoxy, NRaRb, OH, C(O)—(C1-C6) alkyl or oxo groups, Among the compounds that are subjects of the invention, mention may be made of a first group of compounds of formula (I) in which R3 represents H or a halogen atom, more particularly chlorine, the definition of the other substituents remaining unchanged.

Another group of compounds that are subjects of the invention is formed by the compounds of formula (I) in which R1 represents a (C1-C4)alkyl group, more particularly an ethyl group, or a (C1-C4)haloalkyl group, more particularly a trifluoroethyl group, the definition of the other substituents remaining unchanged.

Another group of compounds that are subjects of the invention is formed by the compounds of formula (I) in which R2 represents a group: -A-X with A representing an aryl or heteroaryl group and X being absent or representing a heterocycle, NRaRb, (C1-C6)alkyl, a halogen, more particularly chlorine or fluorine, a cyano. NRa—SO2-Rb or CO-heterocyclic group; the definition of the other substituents remaining unchanged.

The combinations of the abovementioned groups of compounds of the invention also form part of the invention as embodiments according to the invention.

Another group of compounds that are subjects of the invention is formed by the compounds of formula (I) with the exception of the following compounds:

compound 2: 7-(2-aminopyrid-3-yl)-5-(2,2,2-trifluoroethyl)-1,5-dihydro-4H-pyrazolo[4,3-c]quinolin-4-one;

compound 12: 7-[2-(morpholin-4-ylcarbonyl)phenyl]-5-(2,2,2-trifluoroethyl)-1,5-dihydro-4H-pyrazolo[4,3-c]quinolin-4-one;

compound 14: 7-(2-morpholin-4-ylphenyl)-5-(2,2,2-trifluoroethyl)-1,5-dihydro-4H-pyrazolo[4,3-c]quinolin-4-one;

compound 16: 7-(2-morpholin-4-ylmethylphenyl)-5-(2,2,2-trifluoroethyl)-1,5-dihydro-4H-pyrazolo[4,3-c]quinolin-4-one;

compound 19: 7-[4-(4-methylpiperazin-1-yl)phenyl]-5-(2,2,2-trifluoroethyl)-1,5-dihydro-4H-pyrazolo[4,3-c]quinolin-4-one;

compound 23: 7-(4-diethylaminophenyl)-5-(2,2,2-trifluoroethyl)-1,5-dihydro-4H-pyrazolo[4,3-c]quinolin-4-one;

compound 30: 7-[4-(piperazin-1-yl)phenyl]-5-(2,2,2-trifluoroethyl)-1,5-dihydro-4H-pyrazolo[4,3-c]quinolin-4-one;

compound 32: 7-(4-dimethylaminophenyl)-5-(2,2,2-trifluoroethyl)-1,5-dihydro-4H-pyrazolo[4,3-c]quinolin-4-one;

compound 42: 7-(2-{5-[(propan-2-ylamino)methyl]furan-2-yl}phenyl)-5-(2,2,2-trifluoroethyl)-2,5-dihydro-4H-pyrazolo[4,3-c]quinolin-4-one;

compound 66: 7-[6-(piperazin-1-yl)pyrid-3-yl]-5-(2,2,2-trifluoroethyl)-1,5-dihydro-4H-pyrazolo[4,3-c]quinolin-4-one;

compound 68: 7-[2-(4-methylpiperazin-1-yl)pyrid-4-yl]-5-(2,2,2-trifluoroethyl)-1,5-dihydro-4H-pyrazolo[4,3-c]quinolin-4-one;

compound 70: 7-[2-(piperazin-1-yl)pyrid-4-yl]-5-(2,2,2-trifluoroethyl)-1,5-dihydro-4H-pyrazolo[4,3-c]quinolin-4-one;

compound 83: 7-[6-(morpholin-4-yl)pyrid-3-yl]-5-(2,2,2-trifluoroethyl)-1,5-dihydro-4H-pyrazolo[4,3-c]quinolin-4-one;

compound 95: 7-(6-aminopyrid-3-yl)-5-ethyl-1,5-dihydro-4H-pyrazolo[4,3-c]quinolin-4-one;

compound 113: isopropyl 2-[4-oxo-5-(2,2,2-trifluoroethyl)-4,5-dihydro-1H-pyrazolo[4,3-c]quinolin-7-yl]benzoate;

compound 114: cyclopropanecarboxylic acid {2-[4-oxo-5-(2,2,2-trifluoroethyl)-4,5-dihydro-1H-pyrazolo[4,3-c]quinolin-7-yl]phenyl}amide;

compound 115: 7-[2-(1-methyl-1H-imidazole-2-carbonyl)phenyl]-5-(2,2,2-trifluoroethyl)-1,5-dihydro-4H-pyrazolo[4,3-c]quinolin-4-one;

compound 116: 7-(4-cyclopentylpyrimidin-5-yl)-5-(2,2,2-trifluoroethyl)-1,5-dihydro-4H-pyrazolo[4,3-c]quinolin-4-one;

compound 117: 7-(4-cyclohexylpyrimidin-5-yl)-5-(2,2,2-trifluoroethyl)-1,5-dihydro-4H-pyrazolo[4,3-c]quinolin-4-one;

compound 118: 7-(2-propylaminomethylphenyl)-5-(2,2,2-trifluoroethyl)-1,5-dihydro-4H-pyrazolo[4,3-c]quinolin-4-one;

compound 119: 2-methoxy-N-{2-[4-oxo-5-(2,2,2-trifluoroethyl)-4,5-dihydro-1H-pyrazolo[4,3-c]quinolin-7-yl]phenyl}acetamide;

compound 120: N-{2-[4-oxo-5-(2,2,2-trifluoroethyl)-4,5-dihydro-1H-pyrazolo[4,3-c]quinolin-7-yl]phenyl}isobutyramide;

compound 121: N-{4-methyl-2-[4-oxo-5-(2,2,2-trifluoroethyl)-4,5-dihydro-1H-pyrazolo[4,3-c]quinolin-7-yl]phenyl}propionamide;

compound 123: 7-[4-methyl-2-(piperidin-4-yloxy)phenyl]-5-(2,2,2-trifluoroethyl)-1,5-dihydro-4H-pyrazolo[4,3-c]quinolin-4-one;

compound 124: 7-[2-(1,4-diazepan-1-ylmethyl)phenyl]-5-(2,2,2-trifluoroethyl)-1,5-dihydro-4H-pyrazolo[4,3-c]quinolin-4-one;

compound 125: ethyl 2-[4-oxo-5-(2,2,2-trifluoroethyl)-4,5-dihydro-1H-pyrazolo[4,3-c]quinolin-7-yl]benzoate;

compound 126: 7-(2-aminophenyl)-5-(2,2,2-trifluoroethyl)-2,5-dihydro-4H-pyrazolo[4,3-c]quinolin-4-one;

compound 127: 7-(2-piperazin-1-ylphenyl)-5-(2,2,2-trifluoroethyl)-2,5-dihydro-4H-pyrazolo[4,3-c]quinolin-4-one;

compound 172: 7-[2-(morpholin-4-yl)pyrid-3-yl]-5-(2,2,2-trifluoroethyl)-1,5-dihydro-4H-pyrazolo[4,3-c]quinolin-4-one;

compound 174: 7-(2-cyclopropylaminopyrid-3-yl)-5-(2,2,2-trifluoroethyl)-1,5-dihydro-4H-pyrazolo[4,3-c]quinolin-4-one;

compound 178: methyl 2-[4-oxo-5-(2,2,2-trifluoroethyl)-4,5-dihydro-1H-pyrazolo[4,3-c]quinolin-7-yl]nicotinoate;

compound 181: 7-[2-(4-fluorophenylamino)pyrid-3-yl]-5-(2,2,2-trifluoroethyl)-1,5-dihydro-4H-pyrazolo[4,3-c]quinolin-4-one;

compound 196: 8-chloro-7-(pyrid-4-yl)-5-(2,2,2-trifluoroethyl)-1,5-dihydro-4H-pyrazolo[4,3-c]quinolin-4-one;

compound 204: 2-[4-oxo-5-(2,2,2-trifluoroethyl)-4,5-dihydro-1H-pyrazolo[4,3-c]quinolin-7-yl]benzoic acid;

compound 209: 7-{2-[(4-methyl-1,4-diazepan-1-yl)carbonyl]phenyl}-5-(2,2,2-trifluoroethyl)-1,5-dihydro-4H-pyrazolo[4,3-c]quinolin-4-one;

compound 210: 7-{2-[(4-methylpiperazin-1-yl)carbonyl]phenyl}-5-(2,2,2-trifluoroethyl)-1,5-dihydro-4H-4H-pyrazolo[4,3-c]quinolin-4-one;

compound 212: N-(3-dimethylaminopropyl)-2-[4-oxo-5-(2,2,2-trifluoroethyl)-4,5-dihydro-1H-pyrazolo[4,3-c]quinolin-7-yl]benzamide;

compound 214: 2-[4-oxo-5-(2,2,2-trifluoroethyl)-4,5-dihydro-1H-pyrazolo[4,3-c]quinolin-7-yl]-N-[2-(pyrid-4-yl)ethyl]benzamide;

compound 218: 2-[4-oxo-5-(2,2,2-trifluoroethyl)-4,5-dihydro-1H-pyrazolo[4,3-c]quinolin-7-yl]-N-(pyrid-3-ylmethyl)benzamide;

compound 219: N-ethyl-2-[4-oxo-5-(2,2,2-trifluoroethyl)-4,5-dihydro-1H-pyrazolo[4,3-c]quinolin-7-yl]-N-(pyrid-4-ylmethyl)benzamide;

compound 223: N-{3-[4-oxo-5-(2,2,2-trifluoroethyl)-4,5-dihydro-1H-pyrazolo[4,3-c]quinolin-7-yl]pyrid-2-yl}acetamide;

compound 224: 3-dimethylamino-N-{2-[4-oxo-5-(2,2,2-trifluoroethyl)-4,5-dihydro-2H,4H-pyrazolo[4,3-c]quinolin-7-yl]phenyl}propionamide;

compound 225: 4-(dimethylamino)-N-{2-[4-oxo-5-(2,2,2-trifluoroethyl)-4,5-dihydro-1H-pyrazolo[4,3-c]quinolin-7-yl]phenyl}butanamide;

compound 230: 2-(3-chlorophenyl)-N-{-4-[4-oxo-5-(2,2,2-trifluoroethyl)-4,5-dihydro-1H-pyrazolo[4,3-c]quinolin-7-yl]pyrid-3-yl}acetamide;

compound 231: 2-(2,4-dichlorophenyl)-N-{-4-[4-oxo-5-(2,2,2-trifluoroethyl)-4,5-dihydro-1H-pyrazolo[4,3-c]quinolin-7-yl]pyrid-3-yl}acetamide;

compound 232: N-{2-[4-oxo-5-(2,2,2-trifluoroethyl)-4,5-dihydro-2H-pyrazolo[4,3-c]quinolin-7-yl]phenyl}methanesulfonamide;

compound 233: 2-(dimethylamino)-N-{2-[4-oxo-5-(2,2,2-trifluoroethyl)-4,5-dihydro-1H-pyrazolo[4,3-c]quinolin-7-yl]phenyl}ethanesulfonamide;

compound 234: N-{2-[4-oxo-5-(2,2,2-trifluoroethyl)-4,5-dihydro-1H-pyrazolo[4,3-c]quinolin-7-yl]phenyl}-1-phenylmethanesulfonamide;

compound 235: 3-chloro-N-12-[4-oxo-5-(2,2,2-trifluoroethyl)-4,5-dihydro-1H-pyrazolo[4,3-c]quinolin-7-yl]phenyl]benzenesulfonamide;

compound 236: N-{4-[4-oxo-5-(2,2,2-trifluoroethyl)-4,5-dihydro-1H-pyrazolo[4,3-c]quinolin-7-yl]pyrid-3-yl}methanesulfonamide;

compound 237: N-{-4-[4-oxo-5-(2,2,2-trifluoroethyl)-4,5-dihydro-1H-pyrazolo[4,3-c]quinolin-7-yl]pyrid-3-yl}-1-phenylmethanesulfonamide;

compound 238: 3-chloro-N-{-4-[4-oxo-5-(2,2,2-trifluoroethyl)-4,5-dihydro-1H-pyrazolo[4,3-c]quinolin-7-yl]pyrid-3-yl}benzenesulfonamide;

compound 240: N-{4-[4-oxo-5-(2,2,2-trifluoroethyl)-4,5-dihydro-1H-pyrazolo[4,3-c]quinolin-7-yl]pyrid-3-yl}-2-phenoxybenzenesulfonamide.

Among the compounds of formula (I) that are subjects of the invention, mention may be made especially of the following compounds:

compound 1: 7-(pyrid-2-yl)-5-(2,2,2-trifluoroethyl)-1,5-dihydro-4H-pyrazolo[4,3-c]quinolin-4-one;

compound 2: 7-(2-aminopyrid-3-yl)-5-(2,2,2-trifluoroethyl)-1,5-dihydro-4H-pyrazolo[4,3-c]quinolin-4-one;

compound 3: 7-(2-fluorophenyl)-5-(2,2,2-trifluoroethyl)-1,5-dihydro-4H-pyrazolo[4,3-c]quinolin-4-one;

compound 4: 5-ethyl-7-pyrid-2-yl-1,5-dihydro-4H-pyrazolo[4,3-c]quinolin-4-one;

compound 5: 5-ethyl-7-(4-fluorophenyl)-2,5-dihydro-4H-pyrazolo[4,3-c]quinolin-4-one;

compound 6: 7-(pyrid-4-yl)-5-(2,2,2-trifluoroethyl)-1,5-dihydro-4H-pyrazolo[4,3-c]quinolin-4-one;

compound 7: 5-ethyl-7-pyrid-4-yl-1,5-dihydro-4H-pyrazolo[4,3-c]quinolin-4-one;

compound 8: 7-(2-dimethylaminophenyl)-5-ethyl-1,5-dihydro-4H-pyrazolo[4,3-c]quinolin-4-one;

compound 9: N-(3-dimethylaminopropyl)-4-(5-ethyl-4-oxo-4,5-dihydro-1H-pyrazolo[4,3-c]quinolin-7-yl)benzamide;

compound 10: 5-ethyl-7-(4-piperazin-1-ylphenyl)-1,5-dihydro-4H-pyrazolo[4,3-c]quinolin-4-one;

compound 11: 5-ethyl-7-[4-(4-methylpiperazin-1-yl)phenyl]-1,5-dihydro-4H-pyrazolo[4,3-c]quinolin-4-one;

compound 12: 7-[2-(morpholin-4-ylcarbonyl)phenyl]-5-(2,2,2-trifluoroethyl)-1,5-dihydro-4H-pyrazolo[4,3-c]quinolin-4-one:

compound 13: N-(2-dimethylaminoethyl)-4-(5-ethyl-4-oxo-4,5-dihydro-1H-pyrazolo[4,3-c]quinolin-7-yl)benzamide;

compound 14: 7-(2-morpholin-4-ylphenyl)-5-(2,2,2-trifluoroethyl)-1,5-dihydro-4H-pyrazolo[4,3-c]quinolin-4-one;

compound 15: 7-[4-(1-dimethylaminoethyl)phenyl]-5-ethyl-1,5-dihydro-4H-pyrazolo[4,3-c]quinolin-4-one;

compound 16: 7-(2-morpholin-4-ylmethylphenyl)-5-(2,2,2-trifluoroethyl)-1,5-dihydro-4H-pyrazolo[4,3-c]quinolin-4-one;

compound 17: 5-ethyl-7-(2-morpholin-4-ymethylphenyl)-1,5-dihydro-4H-pyrazolo[4,3-c]quinolin-4-one;

compound 18: 5-ethyl-7-[4-(piperazine-1-carbonyl)phenyl]-1,5-dihydro-4H-pyrazolo[4,3-c]quinolin-4-one;

compound 19: 7-[4-(4-methylpiperazin-1-yl)phenyl]-5-(2,2,2-trifluoroethyl)-1,5-dihydro-4H-pyrazolo[4,3-c]quinolin-4-one;

compound 20: 5-ethyl-7-(2-piperazin-1-ylpyrimidin-5-yl)-1,5-dihydro-4H-pyrazolo[4,3-c]quinolin-4-one;

compound 21: 5-ethyl-7-[4-(4-methylpiperazine-1-carbonyl)phenyl]-1,5-dihydro-4H-pyrazolo[4,3-c]quinolin-4-one;

compound 22: 5-ethyl-7-[4-(1-pyrrolidin-1-yl-ethyl)phenyl]-1,5-dihydro-4H-pyrazolo[4,3-c]quinolin-4-one;

compound 23: 7-(4-diethylaminophenyl)-5-(2,2,2-trifluoroethyl)-1,5-dihydro-4H-pyrazolo[4,3-c]quinolin-4-one;

compound 24: 7-(4-amino-2-methylphenyl)-5-ethyl-1,5-dihydro-4H-pyrazolo[4,3-c]quinolin-4-one;

compound 25: 7-(4-morpholin-4-ylphenyl)-5-(2,2,2-trifluoroethyl)-1,5-dihydro-4H-pyrazolo[4,3-c]quinolin-4-one;

compound 26: 5-ethyl-7-(4-morpholin-4-ylphenyl)-1,5-dihydro-4H-pyrazolo[4,3-c]quinolin-4-one;

compound 27: 5-(5-ethyl-4-oxo-4,5-dihydro-1H-pyrazolo[4,3-c]quinolin-7-yl)-2-fluoro-N-methylbenzamide;

compound 28: 5-ethyl-7-(2-fluoro-5-methoxyphenyl)-1,5-dihydro-4H-pyrazolo[4,3-c]quinolin-4-one;

compound 29: 7-[3-chloro-4-(morpholine-4-carbonyl)phenyl]-5-ethyl-1,5-dihydro-4H-pyrazolo[4,3-c]quinolin-4-one;

compound 30: 7-[4-(piperazin-1-yl)phenyl]-5-(2,2,2-trifluoroethyl)-1,5-dihydro-4H-pyrazolo[4,3-c]quinolin-4-one;

compound 31: 5-ethyl-7-[2-(4-methylpiperazin-1-yl)pyrimidin-5-yl]-1,5-dihydro-4H-pyrazolo[4,3-c]quinolin-4-one;

compound 32: 7-(4-dimethylaminophenyl)-5-(2,2,2-trifluoroethyl)-1,5-dihydro-4H-pyrazolo[4,3-c]quinolin-4-one;

compound 33: 2-chloro-4-(5-ethyl-4-oxo-4,5-dihydro-1H-pyrazolo[4,3-c]quinolin-7-yl)benzamide;

compound 34: 5-ethyl-7-(1H-indazol-5-yl)-1,5-dihydro-4H-pyrazolo[4,3-c]quinolin-4-one;

compound 35: N-ethyl-3-(5-ethyl-4-oxo-4,5-dihydro-1H-pyrazolo[4,3-c]quinolin-7-yl)benzamide;

compound 36: 5-(5-ethyl-4-oxo-4,5-dihydro-1H-pyrazolo[4,3-c]quinolin-7-yl)-2-fluoro-benzamide;

compound 37: N-(2-dimethylaminoethyl)-3-(5-ethyl-4-oxo-4,5-dihydro-1H-pyrazolo[4,3-c]quinolin-7-yl)benzamide;

compound 38: N-[4-(5-ethyl-4-oxo-4,5-dihydro-1H-pyrazolo[4,3-c]quinolin-7-yl)benzy]acetamide;

compound 39: 3-(5-ethyl-4-oxo-4,5-dihydro-1H-pyrazolo[4,3-c]quinolin-7-yl)-N-(2-methoxyethyl)benzamide;

compound 40: 7-(3-hydroxyphenyl)-5-(2,2,2-trifluoroethyl)-1,5-dihydro-4H-pyrazolo[4,3-c]quinolin-4-one;

compound 41: 7-(2-chloro-3-fluoropyrid-4-yl)-5-(2,2,2-trifluoroethyl)-1,5-dihydro-4H-pyrazolo[4,3-c]quinolin-4-one;

compound 42: 7-(2-{5-[(propan-2-ylamino)methyl]furan-2-yl}phenyl)-5-(2,2,2-trifluoroethyl)-2,5-dihydro-4H-pyrazolo[4,3-c]quinolin-4-one;

compound 43: N-[2-(5-ethyl-4-oxo-4,5-dihydro-1H-pyrazolo[4,3-c]quinolin-7-yl)phenyl]methanesulfonamide;

compound 44: 7-(2-aminophenyl)-5-ethyl-1,5-dihydro-4H-pyrazolo[4,3-c]quinolin-4-one;

compound 45: 5-ethyl-7-(3-morpholin-4-ylphenyl)-1,5-dihydro-4H-pyrazolo[4,3-c]quinolin-4-one;

compound 46: N-[2-(5-ethyl-4-oxo-4,5-dihydro-1H-pyrazolo[4,3-c]quinolin-7-yl)phenyl]acetamide;

compound 47: 5-ethyl-7-(2-hydroxyphenyl)-1,5-dihydro-4H-pyrazolo[4,3-c]quinolin-4-one;

compound 48: 5-ethyl-7-[4-(morpholine-4-sulfonyl)phenyl]-1,5-dihydro-4H-pyrazolo[4,3-c]quinolin-4-one;
compound 49: 7-(2-hydroxymethyl-4-methoxyphenyl)-5-(2,2,2-trifluoroethyl)-1,5-dihydro-4H-pyrazolo[4,3-c]quinolin-4-one;
compound 50: 5-ethyl-7-(3-pyrazol-1-ylphenyl)-1,5-dihydro-4H-pyrazolo[4,3-c]quinolin-4-one;
compound 51: 5-ethyl-7-(1H-indol-5-yl)-1,5-dihydro-4H-pyrazolo[4,3-c]quinolin-4-one;
compound 52: 5-(5-ethyl-4-oxo-4,5-dihydro-1H-pyrazolo[4,3-c]quinolin-7-yl)-thiophene-2-carbonitrile;
compound 53: 7-(3-chloro-2-hydroxyphenyl)-5-(2,2,2-trifluoroethyl)-1,5-dihydro-4H-pyrazolo[4,3-c]quinolin-4-one;
compound 54: 5-ethyl-7-(2-hydroxy-3-methoxyphenyl)-1,5-dihydro-4H-pyrazolo[4,3-c]quinolin-4-one;
compound 55: methyl 3-amino-4-[4-oxo-5-(2,2,2-trifluoroethyl)-4,5-dihydro-1H-pyrazolo[4,3-c]quinolin-7-yl]benzoate;
compound 56: 5-ethyl-7-(4-methyl-3,4-dihydro-2H-benzo[1,4]oxazin-7-yl)-1,5-dihydro-4H-pyrazolo[4,3-c]quinolin-4-one;
compound 57: 7-(2,5-dichloropyrid-3-yl)-5-(2,2,2-trifluoroethyl)-1,5-dihydro-4H-pyrazolo[4,3-c]quinolin-4-one;
compound 58: 7-(2-chloro-5-methoxyphenyl)-5-ethyl-1,5-dihydro-4H-pyrazolo[4,3-c]quinolin-4-one;
compound 59: N-(3-dimethylaminopropyl)-3-(5-ethyl-4-oxo-4,5-dihydro-1H-pyrazolo[4,3-c]quinolin-7-yl)benzamide:
compound 60: 5-ethyl-7-(4-fluoro-2-hydroxyphenyl)-1,5-dihydro-4H-pyrazolo[4,3-c]quinolin-4-one;
compound 61: 5-ethyl-7-(2-fluoro-4-methoxyphenyl)-1,5-dihydro-4H-pyrazolo[4,3-c]quinolin-4-one;
compound 62: 7-(4-aminomethylphenyl)-5-ethyl-1,5-dihydro-4H-pyrazolo[4,3-c]quinolin-4-one;
compound 63: 5-ethyl-7-(2-fluoro-3-methoxyphenyl)-1,5-dihydro-4H-pyrazolo[4,3-c]quinolin-4-one;
compound 64: 7-(2-dimethylaminomethylphenyl)-5-ethyl-1,5-dihydro-4H-pyrazolo[4,3-c]quinolin-4-one;
compound 65: 4-(5-ethyl-4-oxo-4,5-dihydro-1H-pyrazolo[4,3-c]quinolin-7-yl)benzoic acid;
compound 66: 7-[6-(piperazin-1-yl)pyrid-3-yl]-5-(2,2,2-trifluoroethyl)-1,5-dihydro-4H-pyrazolo[4,3-c]quinolin-4-one;
compound 67: 5-ethyl-7-[6-(piperazin-1-yl)pyrid-3-yl]-1,5-dihydro-4H-pyrazolo[4,3-c]quinolin-4-one;
compound 68: 7-[2-(4-methylpiperazin-1-yl)pyrid-4-yl]-5-(2,2,2-trifluoroethyl)-1,5-dihydro-4H-pyrazolo[4,3-c]quinolin-4-one;
compound 69: 5-ethyl-7-[2-(4-methylpiperazin-1-yl)pyrid-4-yl]-1,5-dihydro-4H-pyrazolo[4,3-c]quinolin-4-one;
compound 70: 7-[2-(piperazin-1-yl)pyrid-4-yl]-5-(2,2,2-trifluoroethyl)-1,5-dihydro-4H-pyrazolo[4,3-c]quinolin-4-one;
compound 71: 5-ethyl-7-(2-piperazin-1-ylpyrid-4-yl)-1,5-dihydro-4H-pyrazolo[4,3-c]quinolin-4-one;
compound 72: 7-(2-methylpyrid-3-yl)-5-(2,2,2-trifluoroethyl)-1,5-dihydro-4H-[4,3-c]quinolin-4-one;
compound 73: 5-ethyl-7-(2-methylpyrid-3-yl)-1,5-dihydro-4H-pyrazolo[4,3-c]quinolin-4-one;
compound 74: 7-(2-chloro-6-methylpyrid-3-yl)-5-ethyl-1,5-dihydro-4H-pyrazolo[4,3-c]quinolin-4-one;
compound 75: 7-(2-chloro-6-methylpyrid-3-yl)-5-(2,2,2-trifluoroethyl)-1,5-dihydro-4H-pyrazolo[4,3-c]quinolin-4-one;
compound 76: 7-(2-chloropyrid-4-yl)-5-(2,2,2-trifluoroethyl)-1,5-dihydro-4H-pyrazolo[4,3-c]quinolin-4-one;
compound 77: 7-(2-fluoropyrid-3-yl)-5-(2,2,2-trifluoroethyl)-1,5-dihydro-4H-pyrazolo[4,3-c]quinolin-4-one;
compound 78: 5-ethyl-7-(2-fluoropyrid-3-yl)-1,5-dihydro-4H-pyrazolo[4,3-c]quinolin-4-one;
compound 79: 7-(6-chloro-2-methylpyrid-3-yl)-5-(2,2,2-trifluoroethyl)-1,5-dihydro-4H-pyrazolo[4,3-c]quinolin-4-one;
compound 80: 7-(2-methoxypyrid-3-yl)-5-(2,2,2-trifluoroethyl)-2,5-dihydro-4H-pyrazolo[4,3-c]quinolin-4-one;
compound 81: 5-ethyl-7-(2-methoxypyrid-3-yl)-1,5-dihydro-4H-pyrazolo[4,3-c]quinolin-4-one;
compound 82: 7-(6-chloro-4-methylpyrid-3-yl)-5-(2,2,2-trifluoroethyl)-1,5-dihydro-4H-pyrazolo[4,3-c]quinolin-4-one;
compound 83: 7-[6-(morpholin-4-yl)pyrid-3-yl]-5-(2,2,2-trifluoroethyl)-1,5-dihydro-4H-pyrazolo[4,3-c]quinolin-4-one;
compound 84: 7-[6-(3-dimethylaminopropoxy)pyrid-3-yl]-5-ethyl-1,5-dihydro-4H-pyrazolo[4,3-c]quinolin-4-one;
compound 85: 5-ethyl-7-quinolin-8-yl-1,5-dihydro-4H-pyrazolo[4,3-c]quinolin-4-one;
compound 86: 7-(6-chloropyrid-2-yl)-5-(2,2,2-trifluoroethyl)-2,5-dihydro-4H-pyrazolo[4,3-c]quinolin-4-one;
compound 87: 5-ethyl-7-quinolin-6-yl-1,5-dihydro-4H-pyrazolo[4,3-c]quinolin-4-one;
compound 88: 7-(6-chloropyrid-3-yl)-5-(2,2,2-trifluoroethyl)-1,5-dihydro-4H-pyrazolo[4,3-c]quinolin-4-one;
compound 89: 7-(6-chloro-5-methylpyrid-3-yl)-5-(2,2,2-trifluoroethyl)-1,5-dihydro-4H-pyrazolo[4,3-c]quinolin-4-one;
compound 90: 5-ethyl-7-(3-fluoropyrid-4-yl)-1,5-dihydro-4H-pyrazolo[4,3-c]quinolin-4-one;
compound 91: 7-(3-chloropyrid-4-yl)-5-ethyl-1,5-dihydro-4H-pyrazolo[4,3-c]quinolin-4-one;
compound 92: 5-ethyl-7-(6-fluoro-5-methylpyrid-3-yl)-1,5-dihydro-4H-pyrazolo[4,3-c]quinolin-4-one;
compound 93: 7-(2-ethoxypyrid-3-yl)-5-ethyl-1,5-dihydro-4H-pyrazolo[4,3-c]quinolin-4-one;
compound 94: 5-ethyl-7-(5-methoxypyrid-3-yl)-1,5-dihydro-4H-pyrazolo[4,3-c]quinolin-4-one;
compound 95: 7-(6-aminopyrid-3-yl)-5-ethyl-1,5-dihydro-4H-pyrazolo[4,3-c]quinolin-4-one;
compound 96: 5-ethyl-7-pyrid-3-yl-2,5-dihydro-4H-pyrazolo[4,3-c]quinolin-4-one;
compound 97: 7-(2-chloro-6-isopropylpyrid-3-yl)-5-(2,2,2-trifluoroethyl)-1,5-dihydro-4H-pyrazolo[4,3-c]quinolin-4-one;
compound 98: 7-(5-chloro-2-methoxypyrid-4-yl)-5-(2,2,2-trifluoroethyl)-1,5-dihydro-4H-pyrazolo[4,3-c]quinolin-4-one;
compound 99: 7-(pyrid-3-yloxy)-5-(2,2,2-trifluoroethyl)-2,5-dihydro-4H-pyrazolo[4,3-c]quinolin-4-one;
compound 100: 5-ethyl-7-(pyrid-3-yloxy)-2,5-dihydro-4H-pyrazolo[4,3-c]quinolin-4-one;
compound 101: 7-(pyrid-3-ylamino)-5-(2,2,2-trifluoroethyl)-2,5-dihydro-4H-pyrazolo[4,3-c]quinolin-4-one;
compound 102: 5-(2,2-difluoroethyl)-7-pyrid-4-yl-1,5-dihydro-4H-pyrazolo[4,3-c]quinolin-4-one;
compound 103: 5-cyclopropylmethyl-7-pyrid-4-yl-1,5-dihydro-4H-pyrazolo[4,3-c]quinolin-4-one;
compound 104: 5-propyl-7-pyrid-4-yl-1,5-dihydro-4H-pyrazolo[4,3-c]quinolin-4-one;
compound 105: 5-(2,2-difluorocyclopropylmethyl)-7-pyrid-4-yl-1,5-dihydro-4H-pyrazolo[4,3-c]quinolin-4-one;
compound 106: 5-(2-fluoroethyl)-7-pyrid-4-yl-1,5-dihydro-4H-pyrazolo[4,3-c]quinolin-4-one;

compound 107: 5-isopropyl-7-pyrid-4-yl-1,5-dihydro-4H-pyrazolo[4,3-c]quinolin-4-one;

compound 108: 5-cyclopropyl-7-pyrid-4-yl-1,5-dihydro-4H-pyrazolo[4,3-c]quinolin-4-one;

compound 109: 8-fluoro-7-pyrid-2-yl-5-(2,2,2-trifluoroethyl)-1,5-dihydro-4H-pyrazolo[4,3-c]quinolin-4-one;

compound 110: 7-(2-chloropyrid-3-yl)-8-methyl-5-(2,2,2-trifluoroethyl)-1,5-dihydro-4H-pyrazolo[4,3-c]quinolin-4-one;

compound 111: 7-(2-chloropyrid-3-yl)-5-(2,2,2-trifluoroethyl)-1,5-dihydro-4H-pyrazolo[4,3-c]quinolin-4-one;

compound 112: 7-[2-(dimethylamino)phenyl]-5-(2,2,2-trifluoroethyl)-1,5-dihydro-4H-pyrazolo[4,3-c]quinolin-4-one;

compound 113: isopropyl 2-[4-oxo-5-(2,2,2-trifluoroethyl)-4,5-dihydro-1H-pyrazolo[4,3-c]quinolin-7-yl]benzoate;

compound 114: cyclopropanecarboxylic acid {2-[4-oxo-5-(2,2,2-trifluoroethyl)-4,5-dihydro-1H-pyrazolo[4,3-c]quinolin-7-yl]phenyl}amide;

compound 115: 7-[2-(1-methyl-1H-imidazole-2-carbonyl)phenyl]-5-(2,2,2-trifluoroethyl)-1,5-dihydro-4H-pyrazolo[4,3-c]quinolin-4-one;

compound 116: 7-(4-cyclopentylpyrimidin-5-yl)-5-(2,2,2-trifluoroethyl)-1,5-dihydro-4H-pyrazolo[4,3-c]quinolin-4-one;

compound 117: 7-(4-cyclohexylpyrimidin-5-yl)-5-(2,2,2-trifluoroethyl)-1,5-dihydro-4H-pyrazolo[4,3-c]quinolin-4-one;

compound 118: 7-(2-propylaminomethylphenyl)-5-(2,2,2-trifluoroethyl)-1,5-dihydro-4H-pyrazolo[4,3-c]quinolin-4-one;

compound 119: 2-methoxy-N-{2-[4-oxo-5-(2,2,2-trifluoroethyl)-4,5-dihydro-1H-pyrazolo[4,3-c]quinolin-7-yl]phenyl}acetamide;

compound 120: N-{2-[4-oxo-5-(2,2,2-trifluoroethyl)-4,5-dihydro-1H-pyrazolo[4,3-c]quinolin-7-yl]phenyl}isobutyramide;

compound 121: N-{4-methyl-2-[4-oxo-5-(2,2,2-trifluoroethyl)-4,5-dihydro-1H-pyrazolo[4,3-c]quinolin-7-yl]phenyl}propionamide;

compound 122: N-isopropyl-2-[4-oxo-5-(2,2,2-trifluoroethyl)-4,5-dihydro-1H-pyrazolo[4,3-c]quinolin-7-yl]benzamide;

compound 123: 7-[4-methyl-2-(piperidin-4-yloxy)phenyl]-5-(2,2,2-trifluoroethyl)-1,5-dihydro-4H-pyrazolo[4,3-c]quinolin-4-one;

compound 124: 7-[2-(1,4-diazepan-1-ylmethyl)phenyl]-5-(2,2,2-trifluoroethyl)-1,5-dihydro-4H-pyrazolo[4,3-c]quinolin-4-one;

compound 125: ethyl 2-[4-oxo-5-(2,2,2-trifluoroethyl)-4,5-dihydro-1H-pyrazolo[4,3-c]quinolin-7-yl]benzoate;

compound 126: 7-(2-aminophenyl)-5-(2,2,2-trifluoroethyl)-2,5-dihydro-41-/- pyrazolo[4,3-c]quinolin-4-one;

compound 127: 7-(2-piperazin-1-ylphenyl)-5-(2,2,2-trifluoroethyl)-2,5-dihydro-4H-pyrazolo[4,3-c]quinolin-4-one;

compound 128: 7-(6-methoxypyrid-3-yl-5-(2,2,2-trifluoroethyl)-1,5-dihydro-4H-pyrazolo[4,3-c]quinolin-4-one;

compound 129: 7-(5-chloro-2-fluoropyrid-3-yl)-5-(2,2,2-trifluoroethyl)-1,5-dihydro-4H-pyrazolo[4,3-c]quinolin-4-one;

compound 130: N-{5-methyl-3-[4-oxo-5-(2,2,2-trifluoroethyl)-4,5-dihydro-1H-pyrazolo[4,3-c]quinolin-7-yl]pyrid-2-yl}acetamide;

compound 131: 7-[2-(2-hydroxy-ethyl)phenyl]-5-(2,2,2-trifluoroethyl)-1,5-dihydro-4H-pyrazolo[4,3-c]quinolin-4-one;

compound 132: 7-(2-amino-5-fluoropyrid-3-yl)-5-(2,2,2-trifluoroethyl)-1,5-dihydro-4H-pyrazolo[4,3-c]quinolin-4-one;

compound 133: 7-[2-(pyrrolidine-1-sulfonyl)phenyl]-5-(2,2,2-trifluoroethyl)-1,5-dihydro-4H-pyrazolo[4,3-c]quinolin-4-one;

compound 134: N-isopropyl-2-[4-oxo-5-(2,2,2-trifluoroethyl)-4,5-dihydro-1H-pyrazolo[4,3-c]quinolin-7-yl]benzenesulfonamide;

compound 135: 7-(2-fluoro-5-methylpyrid-3-yl)-5-(2,2,2-trifluoroethyl)-1,5-dihydro-4H-pyrazolo[4,3-c]quinolin-4-one;

compound 136: N,N-diethyl-2-[4-oxo-5-(2,2,2-trifluoroethyl)-4,5-dihydro-1H-pyrazolo[4,3-c]quinolin-7-yl]benzenesulfonamide;

compound 137: 7-(6-amino-4-methylpyrid-3-yl)-5-(2,2,2-trifluoroethyl)-1,5-dihydro-4H-pyrazolo[4,3-c]quinolin-4-one;

compound 138: 7-(6-methoxy-2-methylpyrid-3-yl)-5-(2,2,2-trifluoroethyl)-1,5-dihydro-4H-pyrazolo[4,3-c]quinolin-4-one;

compound 139: 7-(5-methyl-6-[1,2,4]triazol-4-ylpyrid-3-yl-5-(2,2,2-trifluoroethyl)-1,5-dihydro-4H-pyrazolo[4,3-c]quinolin-4-one;

compound 140: 7-(4-methyl-6-[1,2,4]triazol-4-ylpyrid-3-yl)-5-(2,2,2-trifluoroethyl)-1,5-dihydro-4H-pyrazolo[4,3-c]quinolin-4-one;

compound 141: 7-[6-(morpholine-4-carbonyl)pyrid-3-yl]-5-(2,2,2-trifluoroethyl)-1,5-dihydro-4H-pyrazolo[4,3-c]quinolin-4-one;

compound 142: 7-(6-amino-2-methylpyrid-3-yl)-5-(2,2,2-trifluoroethyl)-1,5-dihydro-4H-pyrazolo[4,3-c]quinolin-4-one;

compound 143: 7-(4-ethylpyrimidin-5-yl)-5-(2,22-trifluoroethyl)-1,5-dihydro-4H-pyrazolo[4,3-c]quinolin-4-one;

compound 144: methyl {2-[4-oxo-5-(2,2,2-trifluoroethyl)-4,5-dihydro-1H-pyrazolo[4,3-c]quinolin-7-yl]phenyl}acetate;

compound 145: 7-(4-methoxypyrid-2-yl)-5-(2,2,2-trifluoroethyl)-1,5-dihydro-4H-pyrazolo[4,3-c]quinolin-4-one;

compound 146: 7-(4-propylpyrimidin-5-yl)-5-(2,2,2-trifluoroethyl)-1,5-dihydro-4H-pyrazolo[4,3-c]quinolin-4-one;

compound 147: N-{6-methyl-5-[4-oxo-5-(2,2,2-trifluoroethyl)-4,5-dihydro-1H-pyrazolo[4,3-c]quinolin-7-yl]pyrid-2-yl}propionamide;

compound 148: 7-(2-oxazol-5-ylphenyl)-5-(2,2,2-trifluoroethyl)-1,5-dihydro-4H-pyrazolo[4,3-c]quinolin-4-one;

compound 149: 7-(4-dimethylamino-2-methoxypyrimidin-5-yl)-5-(2,2,2-trifluoroethyl)-1,5-dihydro-4H-pyrazolo[4,3-c]quinolin-4-one;

compound 150: 7-[2-(5-ethyl-[1,2,4]oxadiazol-3-yl)phenyl]-5-(2,2,2-trifluoroethyl)-1,5-dihydro-4H-pyrazolo[4,3-c]quinolin-4-one;

compound 151: N-{2-[4-oxo-5-(2,2,2-trifluoroethyl)-4,5-dihydro-1H-pyrazolo[4,3-c]quinolin-7-yl]benzyl}acetamide;

compound 152: 7-[5-(hydroxyphenylmethyl)pyrid-2-yl]-5-(2,2,2-trifluoroethyl)-1, 5-dihydro-4H-pyrazolo[4,3-c]quinolin-4-one;

compound 153: 6-[4-oxo-5-(2,2,2-trifluoroethyl)-4,5-dihydro-1H-pyrazolo[4,3-c]quinolin-7-yl]pyridine-2-carbonitrile;

compound 154: 7-(6-hydroxymethylpyrid-2-yl)-5-(2,2,2-trifluoroethyl)-1,5-dihydro-4H-pyrazolo[4,3-c]quinolin-4-one;

compound 155: 7-[3-(2-dimethylaminoethoxy)phenyl]-5-(2,2,2-trifluoroethyl)-1,5-dihydro-4H-pyrazolo[4,3-c]quinolin-4-one;

compound 156: methyl 2-[4-oxo-5-(2,2,2-trifluoroethyl)-4,5-dihydro-1H-pyrazolo[4,3-c]quinolin-7-yl]benzoate;

compound 157: 7-(5-hydroxymethylpyrid-2-yl)-5-(2,2,2-trifluoroethyl)-1,5-dihydro-4H-pyrazolo[4,3-c]quinolin-4-one;

compound 158: 7-(2-methoxypyrid-4-yl)-5-(2,2,2-trifluoroethyl)-1,5-dihydro-4H-pyrazolo[4,3-c]quinolin-4-one;

compound 159: 7-(2-[1,2,4]triazol-1-ylmethylphenyl)-5-(2,2,2-trifluoroethyl)-1,5-dihydro-4H-pyrazolo[4,3-c]quinolin-4-one;

compound 160: 7-(4-phenylpyrimidin-5-yl-5-(2,2,2-trifluoroethyl)-1,5-dihydro-4H-pyrazolo[4,3-c]quinolin-4-one;

compound 161: 7-(6-methoxy-4-methylpyrid-3-yl)-5-(2,2,2-trifluoroethyl)-1,5-dihydro-4H-pyrazolo[4,3-c]quinolin-4-one;

compound 162: 7-(4-isopropylpyrimidin-5-yl)-5-(2,2,2-trifluoroethyl)-1,5-dihydro-4H-pyrazolo[4,3-c]quinolin-4-one;

compound 163: 7-(6-fluoropyrid-2-yl)-5-(2,2,2-trifluoroethyl)-1,5-dihydro-4H-[4,3-c]quinolin-4-one;

compound 164: methyl 6-[4-oxo-5-(2,2,2-trifluoroethyl)-4,5-dihydro-1H-pyrazolo[4,3-c]quinolin-7-yl]pyridine-2-carboxylate;

compound 165: 7-(5-fluoropyrid-2-yl)-5-(2,2,2-trifluoroethyl)-1,5-dihydro-4H-pyrazolo[4,3-c]quinolin-4-one;

compound 166: 7-[2-(4-methylpiperazin-1-yl)pyrid-3-yl]-5-(2,2,2-trifluoroethyl)-1,5-dihydro-4H-pyrazolo[4,3-c]quinolin-4-one;

compound 167: 7-(3-aminopyrid-4-yl)-5-(2,2,2-trifluoroethyl)-1,5-dihydro-4H-pyrazolo[4,3-c]quinolin-4-one;

compound 168: 7-(2,6-dimethylpyrid-4-yl)-5-(2,2,2-trifluoroethyl)-1,5-dihydro-4H-pyrazolo[4,3-c]quinolin-4-one;

compound 169: 7-(3-chloropyrid-2-yl)-5-(2,2,2-trifluoroethyl)-1,5-dihydro-4H-pyrazolo[4,3-c]quinolin-4-one;

compound 170: methyl 3-[4-oxo-5-(2,2,2-trifluoroethyl)-4,5-dihydro-1H-pyrazolo[4,3-c]quinolin-7-yl]pyridine-2-carboxylate;

compound 171: 7-(6-methylpyrid-2-yl)-5-(2,2,2-trifluoroethyl)-1,5-dihydro-4H-pyrazolo[4,3-e]quinolin-4-one;

compound 172: 7-[2-(morpholin-4-yl)pyrid-3-yl]-5-(2,2,2-trifluoroethyl)-1,5-dihydro-4H-pyrazolo[4,3-c]quinolin-4-one;

compound 173: 5-(2,2,2-trifluoroethyl)-7-(2-trifluoromethylpyrid-3-yl)-1,5-dihydro-4H-pyrazolo[4,3-c]quinolin-4-one;

compound 174: 7-(2-cyclopropylaminopyrid-3-yl)-5-(2,2,2-trifluoroethyl)-1,5-dihydro-4H-pyrazolo[4,3-c]quinolin-4-one;

compound 175: 5-(2,2,2-trifluoroethyl)-7-(3-trifluoromethylpyrid-2-yl)-1,5-dihydro-4H-pyrazolo[4,3-c]quinolin-4-one;

compound 176: 3-[4-oxo-5-(2,2,2-trifluoroethyl)-4,5-dihydro-1H-pyrazolo[4,3-c]quinolin-7-yl]pyridine-2-carbonitrile;

compound 177: 2-[4-oxo-5-(2,2,2-trifluoroethyl)-4,5-dihydro-1H-pyrazolo[4,3-c]quinolin-7-yl]pyridine-3-carbonitrile;

compound 178: methyl 2-[4-oxo-5-(2,2,2-trifluoroethyl)-4,5-dihydro-1H-pyrazolo[4,3-c]quinolin-7-yl]nicotinoate;

compound 179: 7-(2-propoxypyrid-3-yl)-5-(2,2,2-trifluoroethyl)-1,5-dihydro-4H-pyrazolo[4,3-c]quinolin-4-one;

compound 180: 7-(3-hydroxypyrid-2-yl)-5-(2,2,2-trifluoroethyl)-1,5-dihydro-4H-pyrazolo[4,3-c]quinolin-4-one;

compound 181: 7-[2-(4-fluorophenylamino)pyrid-3-yl]-5-(2,2,2-trifluoroethyl)-1,5-dihydro-4H-pyrazolo[4,3-c]quinolin-4-one;

compound 182: 7-(2-methylaminophenyl)-5-(2,2,2-trifluoroethyl)-1,5-dihydro-4H-pyrazolo[4,3-c]quinolin-4-one;

compound 183: 7-(2-ethoxypyrid-3-yl)-5-(2,2,2-trifluoroethyl)-1,5-dihydro-4H-pyrazolo[4,3-c]quinolin-4-one;

compound 184: 7-(2-isopropoxypyrid-3-yl)-5-(2,2,2-trifluoroethyl)-1,5-dihydro-4H-pyrazolo[4,3-c]quinolin-4-one;

compound 185: 7-(5-chloro-2-methoxypyrid-3-yl)-5-(2,2,2-trifluoroethyl)-1,5-dihydro-4H-pyrazolo[4,3-c]quinolin-4-one;

compound 186: 7-(2-methylpyrid-4-yl)-5-(2,2,2-trifluoroethyl)-1,5-dihydro-4H-pyrazolo[4,3-c]quinolin-4-one;

compound 187: 7-(4-methylpyrid-2-yl)-5-(2,2,2-trifluoroethyl)-1,5-dihydro-4H-pyrazolo[4,3-c]quinolin-4-one;

compound 188: 7-(6-morpholin-4-ylpyrid-2-yl)-5-(2,2,2-trifluoroethyl)-1,5-dihydro-4H-pyrazolo[4,3-c]quinolin-4-one;

compound 189: 7-(4-methylaminophenyl)-5-(2,2,2-trifluoroethyl)-1,5-dihydro-4H-pyrazolo[4,3-c]quinolin-4-one;

compound 190: 5-(2,2,2-trifluoroethyl)-7-(6-trifluoromethylpyrid-3-yl)-1,5-dihydro-4H-pyrazolo[4,3-c]quinolin-4-one;

compound 191: 7-(6-methoxypyrid-2-yl)-5-(2,2,2-trifluoroethyl)-1,5-dihydro-4H-pyrazolo[4,3-c]quinolin-4-one;

compound 192: 7-[4-(2H-tetrazol-5-yl)phenyl]-5-(2,2,2-trifluoroethyl)-2,5-dihydro-4H-pyrazolo[4,3-c]quinolin-4-one;

compound 193: 7-(3,5-dichloropyrid-2-yl)-5-(2,2,2-trifluoroethyl)-1,5-dihydro-4H-pyrazolo[4,3-c]quinolin-4-one;

compound 194: 8-chloro-7-(pyrid-2-yl)-5-(2,2,2-trifluoroethyl)-1,5-dihydro-4H-pyrazolo[4,3-c]quinolin-4-one;

compound 195: 8-bromo-7-pyrid-2-yl-5-(2,2,2-trifluoroethyl)-1,5-dihydro-4H-pyrazolo[4,3-c]quinolin-4-one;

compound 196: 8-chloro-7-(pyrid-4-yl)-5-(2,2,2-trifluoroethyl)-1,5-dihydro-4H-pyrazolo[4,3-c]quinolin-4-one;

compound 197: 8-bromo-7-(pyrid-4-yl)-5-(2,2,2-trifluoroethyl)-2,5-dihydro-4H-pyrazolo[4,3-c]quinolin-4-one;

compound 198: 8-chloro-5-ethyl-7-pyrid-4-yl-1,5-dihydro-4H-pyrazolo[4,3-c]quinolin-4-one;

compound 199: 8-chloro-7-(2-chloropyrid-3-yl)-5-(2,2,2-trifluoroethyl)-1,5-dihydro-4H-pyrazolo[4,3-c]quinolin-4-one;

compound 200: 8-methyl-7-pyrid-2-yl-5-(2,2,2-trifluoroethyl)-1,5-dihydro-4H-pyrazolo[4,3-c]quinolin-4-one;

compound 201: 4-oxo-7-pyrid-4-yl-5-(2,2,2-trifluoroethyl)-4,5-dihydro-2H,4H-pyrazolo[4,3-c]quinoline-8-carbonitrile;

compound 202: 4-oxo-7-pyrid-4-yl-5-(2,2,2-trifluoroethyl)-4,5-dihydro-2H,4H-pyrazolo[4,3-c]quinoline-8-carboxylic acid;

compound 203: 3-[4-oxo-5-(2,2,2-trifluoroethyl)-4,5-dihydro-1H-pyrazolo[4,3-c]quinolin-7-yl]pyridine-2-carboxylic acid;

compound 204: 2-[4-oxo-5-(2,2,2-trifluoroethyl)-4,5-dihydro-1H-pyrazolo[4,3-c]quinolin-7-yl]benzoic acid;

compound 205: 4-oxo-7-(pyrid-4-yl)-5-(2,2,2-trifluoroethyl)-4,5-dihydro-2H-pyrazolo[4,3-c]quinoline-8-carboxamide;

compound 206: 7-[2-(morpholin-4-ylcarbonyl)pyrid-3-yl]-5-(2,2,2-trifluoroethyl)-1,5dihydro-4H-pyrazolo[4,3-c]quinolin-4-one;

compound 207: N-[2-(dimethylamino)ethyl]-N-methyl-2-[4-oxo-5-(2,2,2-trifluoroethyl)-4,5-dihydro-1H-pyrazolo[4,3-c]quinolin-7-yl]benzamide;

compound 208: N-(2-dimethyaminoethyl)-N-ethyl-2-[4-oxo-5-(2,2,2-trifluoroethyl)-4,5-dihydro-1H-pyrazolo[4,3-c]quinolin-7-yl]benzamide;

compound 209: 7-{2-[(4-methyl-1,4-diazepan-1-yl)carbonyl]phenyl}-5-(2,2,2-trifluoroethyl)-1,5-dihydro-4H-pyrazolo[4,3-c]quinolin-4-one;

compound 210: 7-{2-[(4-methylpiperazin-1-yl)carbonyl]phenyl}-5-(2,2,2-trifluoroethyl)-1,5-dihydro-4H-4H-pyrazolo[4,3-c]quinolin-4-one;

compound 211: N-(3-carbamoylphenyl)-2-[4-oxo-5-(2,2,2-trifluoroethyl)-4,5-dihydro-1H-pyrazolo[4,3-c]quinolin-7-yl]benzamide;

compound 212: N-(3-dimethylaminopropyl)-2-[4-oxo-5-(2,2,2-trifluoroethyl)-4,5-dihydro-1H-pyrazolo[4,3-c]quinolin-7-yl]benzamide;

compound 213: N,N-dimethyl-3-[4-oxo-5-(2,2,2-trifluoroethyl)-4,5-dihydro-1H-pyrazolo[4,3-c]quinolin-7-yl]pyridine-2-carboxamide;

compound 214: 2-[4-oxo-5-(2,2,2-trifluoroethyl)-4,5-dihydro-1H-pyrazolo[4,3-c]quinolin-7-yl]-N-[2-(pyrid-4-yl)ethyl]benzamide;

compound 215: N-[2-(dimethylamino)ethyl]-N-methyl-3-[4-oxo-5-(2,2,2-trifluoroethyl)-4,5-dihydro-1H-pyrazolo[4,3-c]quinolin-7-yl]pyridine-2-carboxamide;

compound 216: 7-[2-(1,4-oxazepan-4-ylcarbonyl)pyrid-3-yl]-5-(2,2,2-trifluoroethyl)-1,5-dihydro-4H-pyrazolo[4,3-c]quinolin-4-one;

compound 217: N-methyl-3-[4-oxo-5-(2,2,2-trifluoroethyl)-4,5-dihydro-1H-pyrazolo[4,3-c]quinolin-7-yl]pyridine-2-carboxamide;

compound 218: 2-[4-oxo-5-(2,2,2-trifluoroethyl)-4,5-dihydro-1H-pyrazolo[4,3-c]quinolin-7-yl]-N-(pyrid-3-ylmethyl)benzamide;

compound 219: N-ethyl-2-[4-oxo-5-(2,2,2-trifluoroethyl)-4,5-dihydro-1H-pyrazolo[4,3-c]quinolin-7-yl]-N-(pyrid-4-ylmethyl)benzamide;

compound 220: 3-[4-oxo-5-(2,2,2-trifluoroethyl)-4,5-dihydro-1H-pyrazolo[4,3-c]quinolin-7-yl]pyridine-2-carboxamide;

compound 221: N-[2-(dimethylamino)ethyl]-N-ethyl-3-[4-oxo-5-(2,2,2-trifluoroethyl)-4,5-dihydro-1H-pyrazolo[4,3-c]quinolin-7-yl]pyridine-2-carboxamide;

compound 222: 7-[2-((2S,6R)-2,6-dimethylmorpholine-4-carbonyl)pyrid-3-yl]-5-(2,2,2-trifluoroethyl)-1,5-dihydro-4H-pyrazolo[4,3-c]quinolin-4-one;

compound 223: N-{3-[4-oxo-5-(2,2,2-trifluoroethyl)-4,5-dihydro-1H-pyrazolo[4,3-c]quinolin-7-yl]pyrid-2-yl}acetamide;

compound 224: 3-dimethylamino-N-{2-[4-oxo-5-(2,2,2-trifluoroethyl)-4,5-dihydro-2H,4H-pyrazolo[4,3-c]quinolin-7-yl]phenyl}propionamide;

compound 225: 4-(dimathylamino)-N-{2-[4-oxo-5-(2,2,2-trifluoroethyl)-4,5-dihydro-1H-pyrazolo[4,3-c]quinolin-7-yl]phenyl}butanamide;

compound 226: N-{-4-[4-oxo-5-(2,2,2-trifluoroethyl)-4,5-dihydro-1H-pyrazolo[4,3-c]quinolin-7-yl]pyrid-3-yl}acetamide;

compound 227: N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 228: 2-methoxy-N-{4-[4-oxo-5-(2,2,2-trifluoroethyl)-4,5-dihydro-1H-pyrazolo[4,3-c]quinolin-7-yl]pyrid-3-yl}-2-phenylacetamide;

compound 229: N-{-4-[4-oxo-5-(2,2,2-trifluoroethyl)-4,5-dihydro-1H-pyrazolo[4,3-c]quinolin-7-yl]pyrid-3-yl}-2-phenylpropionamide;

compound 230: 2-(3-chlorophenyl)-N-{-4-[4-oxo-5-(2,2,2-trifluoroethyl)-4,5-dihydro-1H-pyrazolo[4,3-c]quinolin-7-yl]pyrid-3-yl}acetamide;

compound 231: 2-(2,4-dichlorophenyl)-N-{-4-[4-oxo-5-(2,2,2-trifluoroethyl)-4,5-dihydro-1H-pyrazolo[4,3-c]quinolin-7-yl]pyrid-3-yl}acetamide;

compound 232: N-{2-[4-oxo-5-(2,2,2-trifluoroethyl)-4,5-dihydro-2H-pyrazolo[4,3-c]quinolin-7-yl]phenyl}methanesulfonamide;

compound 233: 2-(dimethylamino)-N-{2-[4-oxo-5-(2,2,2-trifluoroethyl)-4,5-dihydro-1H-pyrazolo[4,3-c]quinolin-7-yl]phenyl}ethanesulfonamide;

compound 234: N-{2-[4-oxo-5-(2,2,2-trifluoroethyl)-4,5-dihydro-1H-pyrazolo[4,3-c]quinolin-7-yl]phenyl}-1-phenylmethanesulfonamide;

compound 235: 3-chloro-N-{2-[4-oxo-5-(2,2,2-trifluoroethyl)-4,5-dihydro-1H-pyrazolo[4,3-c]quinolin-7-yl]phenyl}benzenesulfonamide;

compound 236: N-{-4-[4-oxo-5-(2,2,2-trifluoroethyl)-4,5-dihydro-1H-pyrazolo[4,3-c]quinolin-7-yl]pyrid-3-yl}methanesulfonamide;

compound 237: N-{-4-[4-oxo-5-(2,2,2-trifluoroethyl)-4,5-dihydro-1H-pyrazolo[4,3-c]quinolin-7-yl]pyrid-3-yl}-1-phenylmethanesulfonamide;

compound 238: 3-chloro-N-{-4-[4-oxo-5-(2,2,2-trifluoroethyl)-4,5-dihydro-1H-pyrazolo[4,3-c]quinolin-7-yl]pyrid-3-yl}benzenesulfonamide;

compound 239: N-(4-methoxy-3-{-4-[4-oxo-5-(2,2,2-trifluoroethyl)-4,5-dihydro-1H-pyrazolo[4,3-c]quinolin-7-yl]pyrid-3-ylsulfamoyl}benzyl)acetamide;

compound 240: N-{-4-[4-oxo-5-(2,2,2-trifluoroethyl)-4,5-dihydro-1H-pyrazolo[4,3-c]quinolin-7-yl]pyrid-3-yl}-2-phenoxybenzenesulfonamide;

compound 241: N-methyl-N-{3-[4-oxo-5-(2,2,2-trifluoroethyl)-4,5-dihydro-1H-pyrazolo[4,3-c]quinolin-7-yl]pyrid-2-yl}acetamide;

compound 242: N-methyl-N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 243: 7-[2-(methylamino)pyrid-3-yl]-5-(2,2,2-trifluoroethyl)-1,5-dihydro-4H-pyrazolo[4,3-c]quinolin-4-one;

compound 244: 7-[2-(1,4-diazepan-1-yl)pyrid-3-yl]-5-(2,2,2-trifluoroethyl)-1,5-dihydro-4H-pyrazolo[4,3-c]quinolin-4-one;

compound 245: 7-(3,4,5,6-tetrahydro-2H-[1,2]bipyridinyl-3'-yl)-5-(2,2,2-trifluoroethyl)-2,5-dihydro-4H-pyrazolo[4,3-c]quinolin-4-one;

compound 246: 7-[2-(3-hydroxypyrrolidin-1-yl)pyrid-3-yl]-5-(2,2,2-trifluoroethyl)-1,5-dihydro-4H-pyrazolo[4,3-c]quinolin-4-one;

compound 247: 7-[2-(3,4-dihydroxypyrrolidin-1-yl)pyrid-3-yl]-5-(2,2,2-trifluoroethyl)-2,5-dihydro-4H-pyrazolo[4,3-c]quinolin-4-one;

compound 248: 7-[2-(dimethylamino)pyrid-3-yl]-5-(2,2,2-trifluoroethyl)-1,5-dihydro-4H-pyrazolo[4,3-c]quinolin-4-one;

compound 249: 7-{2-[ethyl(methyl)amino]pyrid-3-yl}-5-(2,2,2-trifluoroethyl)-1,5-dihydro-4H-pyrazolo[4,3-c]quinolin-4-one;

compound 250: 7-{2-[(2-hydroxyethyl)(methyl)amino]pyrid-3-yl}-5-(2,2,2-trifluoroethyl)-1,5-dihydro-4H-pyrazolo[4,3-c]quinolin-4-one;

compound 251: 7-[2-(pyrrolidin-1-yl)pyrid-3-yl]-5-(2,2,2-trifluoroethyl)-1,5-dihydro-4H-pyrazolo[4,3-c]quinolin-4-one;

compound 252: 7-[2-(1,4-oxazepan-4-yl)pyrid-3-yl]-5-(2,2,2-trifluoroethyl)-1,5-dihydro-4H-pyrazolo[4,3-c]quinolin-4-one;

compound 253: 7-[2-(3-oxopiperazin-1-W)pyrid-3-yl]-5-(2,2,2-trifluoroethyl)-1,5-dihydro-4H-pyrazolo[4,3-c]quinolin-4-one;

compound 254: 7-[2-(azetidin-1-yl)pyrid-3-yl]-5-(2,2,2-trifluoroethyl)-1,5-dihydro-4H-pyrazolo[4,3-c]quinolin-4-one;

compound 255: 7-{2-[(2-methoxyethyl)methylamino]pyrid-3-yl}-5-(2,2,2-trifluoroethyl)-2,5-dihydro-4H-pyrazolo[4,3-c]quinolin-4-one;

compound 256: 7-[2-(4-acetylpiperazin-1-W)pyrid-3-yl]-5-(2,2,2-trifluoroethyl)-2,5-dihydro-4H-pyrazolo[4,3-c]quinolin-4-one;

compound 257: 7-[2-(diethylamino)pyrid-3-yl]-5-(2,2,2-trifluoroethyl)-1,5-dihydro-4H-pyrazolo[4,3-c]quinolin-4-one;

compound 258: 7-[2-(cyclobutylamino)pyrid-3-yl]-5-(2,2,2-trifluoroethyl)-1,5-dihydro-4H-pyrazolo[4,3-c]quinolin-4-one;

compound 259: 7-[2-(2,6-dimethylmorpholin-4-yl)pyrid-3-yl]-5-(2,2,2-trifluoroethyl)-2,5-dihydro-4H-pyrazolo[4,3-c]quinolin-4-one;

compound 260: 7-[2-(4-cyclopropylpiperazin-1-yl)pyrid-4-yl]-5-(2,2,2-trifluoroethyl)-1,5-dihydro-4H-pyrazolo[4,3-c]quinolin-4-one;

compound 261: 7-(2-cyclohexylaminopyrid-3-yl)-5-(2,2,2-trifluoroethyl)-2,5-dihydro-4H-pyrazolo[4,3-c]quinolin-4-one;

compound 262: 7-[2-(isopropylmethylamino)pyrid-3-yl]-5-(2,2,2-trifluoroethyl)-2,5-dihydro-4H-pyrazolo[4,3-c]quinolin-4-one;

compound 263: 7-(2-cyclopentylaminopyrid-3-yl)-5-(2,2,2-trifluoroethyl)-2,5-dihydro-4H-pyrazolo[4,3-c]quinolin-4-one;

compound 264: 7-(6-pyrrolidin-1-ylpyrid-2-yl)-5-(2,2,2-trifluoroethyl)-2,5-dihydro-4H-pyrazolo[4,3-c]quinolin-4-one;

compound 265: 7-[6-(2,6-dimethylmorpholin-4-yl)pyrid-2-yl]-5-(2,2,2-trifluoroethyl)-2,5-dihydro-4H-pyrazolo[4,3-c]quinolin-4-one;

compound 266: 7-{2-[cyclohexyl(methyl)amino]pyrid-3-yl}-5-(2,2,2-trifluoroethyl)-1,5-dihydro-4H-pyrazolo[4,3-c]quinolin-4-one;

compound 267: 7-[2-(4-cyclopropylpiperazin-1-yl)pyrid-3-yl]-5-(2,2,2-trifluoroethyl)-2,5-dihydro-4H-pyrazolo[4,3-c]quinolin-4-one;

compound 268: 7-[3-(4-cyclopropylpiperazin-1-yl)phenyl]-5-(2,2,2-trifluoroethyl)-1,5-dihydro-4H-pyrazolo[4,3-c]quinolin-4-one;

compound 269: 7-[2-(4-acetyl-1,4-diazepan-1-yl)pyrid-3-yl]-5-(2,2,2-trifluoroethyl)-1,5-dihydro-4H-pyrazolo[4,3-c]quinolin-4-one;

compound 270: 7-[2-(4-methyl-1,4-diazepan-1-yl)pyrid-3-yl]-5-(2,2,2-trifluoroethyl)-1,5-dihydro-4H-pyrazolo[4,3-c]quinolin-4-one;

compound 271: 7-[2-(4-cyclopropyl-[1,4]diazepan-1-yl)pyrid-3-yl]-5-(2,2,2-trifluoroethyl)-2,5-dihydro-4H-pyrazolo[4,3-c]quinolin-4-one;

compound 272: 7-[2-(3-fluoropyrrolidin-1-yl)pyrid-3-yl]-5-(2,2,2-trifluoroethyl)-2,5-dihydro-4H-pyrazolo[4,3-c]quinolin-4-one;

compound 273: 7-[2-(4-fluoropiperidin-1-yl)pyrid-3-yl]-5-(2,2,2-trifluoroethyl)-1,5-dihydro-4H-pyrazolo[4,3-c]quinolin-4-one;

compound 274: 7-(2-hydroxypyrid-3-yl)-5-(2,2,2-trifluoroethyl)-1,5-dihydro-4H-pyrazolo[4,3-c]quinolin-4-one;

compound 275: 7-(1-oxypyrid-2-yl-5-(2,2,2-trifluoroethyl)-1,5-dihydro-4H-pyrazolo[4,3-c]quinolin-4-one;

compound 276: 7-(1-oxypyrid-4-yl)-5-(2,2,2-trifluoroethyl)-1,5-dihydro-4H-pyrazolo[4,3-c]quinolin-4-one; in the form of the base or of an acid-addition salt, and also in hydrate form.

Among the compounds of formula (I) that are subjects of the invention, mention may be made especially of the following compounds:

compound 1: 7-(pyrid-2-yl)-5-(2,2,2-trifluoroethyl)-1,5-dihydro-4H-pyrazolo[4,3-c]quinolin-4-one;

compound 3: 7-(2-fluorophenyl)-5-(2,2,2-trifluoroethyl)-1,5-dihydro-4H-pyrazolo[4,3-c]quinolin-4-one;

compound 4: 5-ethyl-7-pyrid-2-yl-1,5-dihydro-4H-pyrazolo[4,3-c]quinolin-4-one compound 5: 5-ethyl-7-(4-fluorophenyl)-2,5-dihydro-4H-pyrazolo[4,3-c]quinolin-4-one;

compound 6: 7-(pyrid-4-yl)-5-(2,2,2-trifluoroethyl)-1,5-dihydro-4H-pyrazolo[4,3-c]quinolin-4-one;

compound 7: 5-ethyl-7-pyrid-4-yl-1,5-dihydro-4H-pyrazolo[4,3-c]quinolin-4-one;

compound 8: 7-(2-dimethylaminophenyl)-5-ethyl-1,5-dihydro-4H-pyrazolo[4,3-c]quinolin-4-one;

compound 9: N-(1-dimethylaminopropyl)-4-(5-ethyl-4-oxo-4,5-dihydro-1H pyrazolo[4,3-c]quinolin-7-yl)benzamide;

compound 10: 5-ethyl-7-(4-piperazin-1-ylphenyl)-1,5-dihydro-4H-pyrazolo[4,3-c]quinolin-4-one;

compound 11: 5-ethyl-7-[4-(4-methylpiperazin-1-yl)phenyl]-1,5-dihydro-4H-pyrazolo[4,3-c]quinolin-4-one;

compound 13: N-(2-dimethylaminoethyl)-4-(5-ethyl-4-oxo-4,5-dihydro-1H-pyrazolo[4,3-c]quinolin-7-yl)benzamide;

compound 15: 7-[4-(1-dimethylaminoethyl)phenyl]-5-ethyl-1,5-dihydro-4H-pyrazolo[4,3-c]quinolin-4-one;

compound 17: 5-ethyl-7-(2-morpholin-4-ylmethylphenyl)-1,5-dihydro-4H-pyrazolo[4,3-c]quinolin-4-one;

compound 18: 5-ethyl-7-[4-(piperazine-1-carbonyl)phenyl]-1,5-dihydro-4H-pyrazolo[4,3-c]quinolin-4-one;

compound 20: 5-ethyl-7-(2-piperazin-1-ylpyrimidin-5-yl)-1,5-dihydro-4H-pyrazolo[4,3-c]quinolin-4-one;

compound 21: 5-ethyl-7-[4-(4-methylpiperazine-1-carbonyl)phenyl]-1,5-dihydro-4H-pyrazolo[4,3-c]quinolin-4-one;

compound 22: 5-ethyl-7-[4-(1-pyrrolidin-1-yl-ethyl)phenyl]-1,5-dihydro-4H-pyrazolo[4,3-c]quinolin-4-one;

compound 24: 7-(4-amino-2-methylphenyl)-5-ethyl-1,5-dihydro-4H-pyrazolo[4,3-c]quinolin-4-one;

compound 25: 7-(4-morpholin-4-ylphenyl)-5-(2,2,2-trifluoroethyl)-1,5-dihydro-4H-pyrazolo[4,3-c]quinolin-4-one;

compound 26: 5-ethyl-7-(4-morpholin-4-ylphenyl)-1,5-dihydro-4H-pyrazolo[4,3-c]quinolin-4-one;

compound 27: 5-(5-ethyl-4-oxo-4,5-dihydro-1H-pyrazolo[4,3-c]quinolin-7-yl)-2-fluoro-N-methylbenzamide;

compound 28: 5-ethyl-7-(2-fluoro-5-methoxyphenyl)-1,5-dihydro-4H-pyrazolo[4,3-c]quinolin-4-one;

compound 29: 7-[3-chloro-4-(morpholine-4-carbonyl)phenyl]-5-ethyl-1,5-dihydro-4H-pyrazolo[4,3-c]quinolin-4-one;

compound 31: 5-ethyl-7-[2-(4-methylpiperazin-1-yl)pyrimidin-5-yl]-1,5-dihydro-4H-pyrazolo[4,3-c]quinolin-4-one;

compound 33: 2-chloro-4-(5-ethyl-4-oxo-4,5-dihydro-1H-pyrazolo[4,3-c]quinolin-7-yl)benzamide;

compound 34: 5-ethyl-7-(1H-indazol-5-yl)-1,5-dihydro-4H-pyrazolo[4,3-c]quinolin-4-one;

compound 35: N-ethyl-3-(5-ethyl-4-oxo-4,5-dihydro-1H-pyrazolo[4,3-c]quinolin-7'yl)benzamide;

compound 36: 5-(5-ethyl-4-oxo-4,5-dihydro-1H-pyrazolo[4,3-c]quinolin-7-yl)-2-fluoro-benzamide;
compound 37: N-(2-dimethylaminoethyl)-3-(5-ethyl-4-oxo-4,5-dihydro-1H-pyrazolo[4,3-c]quinolin-7-yl)benzamide;
compound 38: N-[4-(5-ethyl-4-oxo-4,5-dihydro-1H-pyrazolo[4,3-c]quinolin-7-yl)benzyl]acetamide;
compound 39: 3-(5-ethyl-4-oxo-4,5-dihydro-1H-pyrazolo[4,3-c]quinolin-7-yl)-N-(2-methoxyethyl)benzamide;
compound 40: 7-(3-hydroxyphenyl)-5-(2,2,2-trifluoroethyl)-1,5-dihydro-4H-pyrazolo[4,3-c]quinolin-4-one;
compound 41: 7-(2-chloro-3-fluoropyrid-4-yl)-5-(2,2,2-trifluoroethyl)-1,5-dihydro-4H-pyrazolo[4,3-c]quinolin-4-one;
compound 43: N-[2-(5-ethyl-4-oxo-4,5-dihydro-1H-pyrazolo[4,3-c]quinolin-7-yl)phenyl]methanesulfonamide;
compound 44: 7-(2-aminophenyl)-5-ethyl-1,5-dihydro-4H-pyrazolo[4,3-c]quinolin-4-one;
compound 45: 5-ethyl-7-(3-morpholin-4-ylphenyl)-1,5-dihydro-4H-pyrazolo[4,3-c]quinolin-4-one;
compound 46: N-[2-(5-ethyl-4-oxo-4,5-dihydro-1H-pyrazolo[4,3-c]quinolin-7-yl)phenyl]acetamide;
compound 47: 5-ethyl-7-(2-hydroxyphenyl)-1,5-dihydro-4H-pyrazolo[4,3-c]quinolin-4-one;
compound 48: 5-ethyl-7-[4-(morpholine-4-sulfonyl)phenyl]-1,5-dihydro-4H-pyrazolo[4,3-c]quinolin-4-one;
compound 49: 7-(2-hydroxymethyl-4-methoxyphenyl)-5-(2,2,2-trifluoroethyl)-1,5-dihydro-4H-pyrazolo[4,3-c]quinolin-4-one;
compound 50: 5-ethyl-7-(3-pyrazol-1-ylphenyl)-1,5-dihydro-4H-pyrazolo[4,3-c]quinolin-4-one;
compound 51: 5-ethyl-7-(1H-indol-5-yl)-1,5-dihydro-4H-pyrazolo[4,3-c]quinolin-4-one;
compound 52: 5-(5-ethyl-4-oxo-4,5-dihydro-1H-pyrazolo[4,3-c]quinolin-7-yl)-thiophene-2-carbonitrile;
compound 53: 7-(3-chloro-2-hydroxyphenyl)-5-(2,2,2-trifluoroethyl)-1-dihydro-4H-pyrazolo[4,3-c]quinolin-4-one;
compound 54: 5-ethyl-7-(2-hydroxy-3-methoxyphenyl)-1,5-dihydro-4H-pyrazolo[4,3-c]quinolin-4-one;
compound 55: methyl 3-amino-4-[4-oxo-5-(2,2,2-trifluoroethyl)-4,5-dihydro-1H-pyrazolo[4,3-c]quinolin-7-yl]benzoate;
compound 56: 5-ethyl-7-(4-methyl-3,4-dihydro-2H-benzo[1,4]oxazin-7-yl)-1,5-dihydro-4H-pyrazolo[4,3-c]quinolin-4-one;
compound 57: 7-(2,5-dichloropyrid-3-yl)-5-(2,2,2-trifluoroethyl)-1,5-dihydro-4H-pyrazolo[4,3-c]quinolin-4-one;
compound 58: 7-(2-chloro-5-methoxyphenyl)-5-ethyl-1,5-dihydro-4H-pyrazolo[4,3-c]quinolin-4-one;
compound 59: N-(3-dimethylaminopropyl)-3-(5-ethyl-4-oxo-4,5-dihydro-1H-pyrazolo[4,3-c]quinolin-7-yl)benzamide;
compound 60: 5-ethyl-7-(4-fluoro-2-hydroxyphenyl)-1,5-dihydro-4H-pyrazolo[4,3-c]quinolin-4-one;
compound 61: 5-ethyl-7-(2-fluoro-4-methoxyphenyl)-1,5-dihydro-4H-pyrazolo[4,3-c]quinolin-4-one;
compound 62: 7-(4-aminomethylphenyl)-5-ethyl-1,5-dihydro-4H-pyrazolo[4,3-c]quinolin-4-one;
compound 63: 5-ethyl-7-(2-fluoro-3-methoxyphenyl)-1,5-dihydro-4H-pyrazolo[4,3-c]quinolin-4-one;
compound 64: 7-(2-dimethylaminomethylphenyl)-5-ethyl-1,5-dihydro-4H-pyrazolo[4,3-c]quinolin-4-one;
compound 65: 4-(5-ethyl-4-oxo-4,5-dihydro-1H-pyrazolo[4,3-c]quinolin-7-yl)benzoic acid;
compound 67: 5-ethyl-7-[6-(piperazin-1-yl)pyrid-3-yl]-1,5-dihydro-4H-pyrazolo[4,3-c]quinolin-4-one;
compound 69: 5-ethyl-7-[2-(4-methylpiperazin-1-yl)pyrid-4-yl]-1,5-dihydro-4H-pyrazolo[4,3-c]quinolin-4-one;
compound 71: 5-ethyl-7-(2-piperazin-1-ylpyrid-4-yl)-1,5-dihydro-4H-pyrazolo[4,3-c]quinolin-4-one;
compound 72: 7-(2-methylpyrid-3-yl)-5-(2,2,2-trifluoroethyl)-1,5-dihydro-4H-pyrazolo[4,3-c]quinolin-4-one;
compound 73: 5-ethyl-7-(2-methylpyrid-3-yl)-1,5-dihydro-4H-pyrazolo[4,3-c]quinolin-4-one;
compound 74: 7-yl-chloro-6-methylpyrid-3-yl)-5-ethyl-1,5-dihydro-4H-pyrazolo[4,3-c]quinolin-4-one;
compound 75: 7-(2-chloro-6-methylpyrid-3-yl)-5-(2,2,2-trifluoroethyl)-1,5-dihydro-4H-pyrazolo[4,3-c]quinolin-4-one;
compound 76: 7-(2-chloropyrid-4-yl)-5-(2,2,2-trifluoroethyl)-1,5-dihydro-4H-pyrazolo[4,3-c]quinolin-4-one;
compound 77: 7-(2-fluoropyrid-3-yl-5-(2,2,2-trifluoroethyl)-1,5-dihydro-4H-pyrazolo[4,3-c]quinolin-4-one;
compound 78: 5-ethyl-7-(2-fluoropyrid-3-yl)-1,5-dihydro-4H-pyrazolo[4,3-c]quinolin-4-one;
compound 79: 7-(6-chloro-2-methylpyrid-3-yl)-5-(2,2,2-trifluoroethyl)-1,5-dihydro-4H-pyrazolo[4,3-c]quinolin-4-one;
compound 80: 7-(2-methoxypyrid-3-yl)-5-(2,2,2-trifluoroethyl)-2,5-dihydro-4H-pyrazolo[4,3-c]quinolin-4-one;
compound 81: 5-ethyl-7-(2-methoxypyrid-3-yl)-1,5-dihydro-4H-pyrazolo[4,3-c]quinolin-4-one;
compound 82: 7-(6-chloro-4-methylpyrid-3-yl)-5-(2,2,2-trifluoroethyl)-1,5-dihydro-4H-pyrazolo[4,3-c]quinolin-4-one;
compound 84: 7-[6-(3-dimethylaminopropoxy)pyrid-3-yl]-5-ethyl-1,5-dihydro-4H-pyrazolo[4,3-c]quinolin-4-one;
compound 85: 5-ethyl-7-quinolin-8-yl-1,5-dihydro-4H-pyrazolo[4,3-c]quinolin-4-one;
compound 86: 7-(6-chloropyrid-2-yl)-5-(2,2,2-trifluoroethyl)-2,5-dihydro-4H-pyrazolo[4,3-c]quinolin-4-one;
compound 87: 5-ethyl-7-quinolin-6-yl-1,5-dihydro-4H-pyrazolo[4,3-c]quinolin-4-one;
compound 88: 7-(6-chloropyrid-3-yl)-5-(2,2,2-trifluoroethyl)-1,5-dihydro-4H-pyrazolo[4,3-c]quinolin-4-one;
compound 89: 7-(6-chloro-5-methylpyrid-3-yl)-5-(2,2,2-trifluoroethyl)-1,5-dihydro-4H-pyrazolo[4,3-c]quinolin-4-one;
compound 90: 5-ethyl-7-(3-fluoropyrid-4-yl)-1,5-dihydro-4H-pyrazolo[4,3-c]quinolin-4-one;
compound 91: 7-(3-chloropyrid-4-yl)-5-ethyl-1,5-dihydro-4H-pyrazolo[4,3-c]quinolin-4-one;
compound 92: 5-ethyl-7-(6-fluoro-5-methylpyrid-3-yl)-1,5-dihydro-4H-pyrazolo[4,3-c]quinolin-4-one;
compound 93: 7-(2-ethoxypyrid-3-yl)-5-ethyl-1,5-dihydro-4H-pyrazolo[4,3-c]quinolin-4-one;
compound 94: 5-ethyl-7-(5-methoxypyrid-3-yl)-1,5-dihydro-4H-pyrazolo[4,3-c]quinolin-4-one;
compound 96: 5-ethyl-7-pyrid-3-yl-2,5-dihydro-4H-pyrazolo[4,3-c]quinolin-4-one;
compound 97: 7-(2-chloro-6-isopropylpyrid-3-yl)-5-(2,2,2-trifluoroethyl)-1,5-dihydro-4H-pyrazolo[4,3-c]quinolin-4-one;
compound 98: 7-(5-chloro-2-methoxypyrid-4-yl-5-(2,2,2-trifluoroethyl)-1,5-dihydro-4H-pyrazolo[4,3-c]quinolin-4-one;
compound 99: 7-(pyrid-3-yloxy)-5-(2,2,2-trifluoroethyl)-2,5-dihydro-4H-pyrazolo[4,3-c]quinolin-4-one;
compound 100: 5-ethyl-7-(pyrid-3-yloxy)-2,5-dihydro-4H-pyrazolo[4,3-c]quinolin-4-one;
compound 101: 7-(pyrid-3-ylamino)-5-(2,2,2-trifluoroethyl)-2,5-dihydro-4H-pyrazolo[4,3-c]quinolin-4-one;
compound 102: 5-(2,2-difluoroethyl)-7-pyrid-4-yl-1,5-dihydro-4H-pyrazolo[4,3-c]quinolin-4-one compound 103: 5-cyclopropylmethyl-7-pyrid-4-yl-1,5-dihydro-4H-pyrazolo[4,3-c]quinolin-4-one;
compound 104: 5-propyl-7-pyrid-4-yl-1,5-dihydro-4H-pyrazolo[4,3-c]quinolin-4-one;
compound 105: 5-(2,2-difluorocyclopropylmethyl)-7-pyrid-4-yl-1,5-dihydro-4H-pyrazolo[4,3-c]quinolin-4-one;
compound 106: 5-(2-fluoroethyl)-7-pyrid-4-yl-1,5-dihydro-4H-pyrazolo[4,3-c]quinolin-4-one;
compound 107: 5-isopropyl-7-pyrid-4-yl-1,5-dihydro-4H-pyrazolo[4,3-c]quinolin-4-one;
compound 108: 5-cyclopropyl-7-pyrid-4-yl-1,5-dihydro-4H-pyrazolo[4,3-c]quinolin-4-one;
compound 109: 8-fluoro-7-pyrid-2-yl-5-(2,2,2-trifluoroethyl)-1,5-dihydro-4H-pyrazolo[4,3-c]quinolin-4-one;
compound 110: 7-(2-chloropyrid-3-yl)-8-methyl-5-(2,2,2-trifluoroethyl)-1,5-dihydro-4H-pyrazolo[4,3-c]quinolin-4-one;
compound 111: 7-(2-chloropyrid-3-yl)-5-(2,2,2-trifluoroethyl)-1,5-dihydro-4H-pyrazolo[4,3-c]quinolin-4-one;
compound 112: 7-[2-(dimethylamino)phenyl]-5-(2,2,2-trifluoroethyl)-1,5-dihydro-4H-pyrazolo[4,3-c]quinolin-4-one;
compound 122: N-isopropyl-2-[4-oxo-5-(2,2,2-trifluoroethyl)-4,5-dihydro-1H-pyrazolo[4,3-c]quinolin-7-yl]benzamde;
compound 128: 7-(6-methoxypyrid-3-yl)-5-(2,2,2-trifluoroethyl)-1,5-dihydro-4H-pyrazolo[4,3-c]quinolin-4-one;
compound 129: 7-(5-chloro-2-fluoropyrid-3-yl)-5-(2,2,2-trifluoroethyl)-1,5-dihydro-4H-[4,3-c]quinolin-4-one;
compound 130: N-(5-methyl-3-[4-oxo-5-(2,2,2-trifluoroethyl)-4,5-dihydro-1H-pyrazolo[4,3-c]quinolin-7-yl]pyrid-2-ylacetamide;
compound 131: 7-[2-(2-hydroxy-ethyl)phenyl]-5-(2,2,2-trifluoroethyl)-1,5-dihydro-4H-pyrazolo[4,3-c]quinolin-4-one;
compound 132: 7-(2-amino-5-fluoropyrid-3-yl)-5-(2,2,2-trifluoroethyl)-1,5-dihydro-4H-pyrazolo[4,3-c]quinolin-4-one;
compound 133: 7-[2-(pyrrolidine-1-sulfonyl)phenyl]-5-(2,2,2-trifluoroethyl)-1,5-dihydro-4H-pyrazolo[4,3-c]quinolin-4-one;
compound 134: N-isopropyl-2-[4-oxo-5-(2,2,2-trifluoroethyl)-4,5-dihydro-1H-pyrazolo[4,3-c]quinolin-7-yl]benzenesulfonamide;
compound 135: 7-(2-fluoro-5-methylpyrid-3-yl)-5-(2,2,2-trifluoroethyl)-1,5-dihydro-4H-pyrazolo[4,3-c]quinolin-4-one;
compound 136: N,N-diethyl-2-[4-oxo-5-(2,2,2-trifluoroethyl)-4,5-dihydro-1H-pyrazolo[4,3-c]quinolin-7-yl]benzenesulfonamide;
compound 137: 7-(6-amino-4-methylpyrid-3-yl)-5-(2,2,2-trifluoroethyl)-1,5-dihydro-4H-pyrazolo[4,3-c]quinolin-4-one;
compound 138: 7-(6-methoxy-2-methylpyrid-3-yl)-5-(2,2,2-trifluoroethyl)-1,5-dihydro-4H-pyrazolo[4,3-c]quinolin-4-one;
compound 139: 7-(5-methyl-6-[1,2,4]triazol-4-ylpyrid-3-yl)-5-(2,2,2-trifluoroethyl)-1,5-dihydro-4H-pyrazolo[4,3-c]quinolin-4-one;
compound 140: 7-(4-methyl-6-[1,2,4]triazol-4-ylpyrid-3-yl)-5-(2,2,2-trifluoroethyl)-1,5-dihydro-4H-pyrazolo[4,3-c]quinolin-4-one;
compound 141: 7-[6-(morpholine-4-carbonyl)pyrid-3-yl]-5-(2,2,2-trifluoroethyl)-1,5-dihydro-4H-pyrazolo[4,3-c]quinolin-4-one;
compound 142: 7-(6-amino-2-methylpyrid-3-yl)-5-(2,2,2-trifluoroethyl)-1,5-dihydro-4H-pyrazolo[4,3-c]quinolin-4-one;
compound 143: 7-(4-ethylpyrimidin-5-yl)-5-(2,2,2-trifluoroethyl)-1,5-dihydro-4H-pyrazolo[4,3-c]quinolin-4-one;
compound 144: methyl {2-[4-oxo-5-(2,2,2-trifluoroethyl)-4,5-dihydro-1H-pyrazolo[4,3-c]quinolin-7-yl]phenyl}acetate;
compound 145: 7-(4-methoxypyrid-2-yl)-5-(2,2,2-trifluoroethyl)-1,5-dihydro-4H-pyrazolo[4,3-c]quinolin-4-one;
compound 146: 7-(4-propylpyrimidin-5-yl)-5-(2,2,2-trifluoroethyl)-1,5-dihydro-4H-pyrazolo[4,3-c]quinolin-4-one;
compound 147: N-{6-methyl-5-[4-oxo-5-(2,2,2-trifluoroethyl)-4,5-dihydro-1H-pyrazolo[4,3-c]quinolin-7-yl]pyrid-2-yl}propionamide;
compound 148: 7-(2-oxazol-5-ylphenyl)-5-(2,2,2-trifluoroethyl)-1,5-dihydro-4H-pyrazolo[4,3-c]quinolin-4-one;
compound 149: 7-(4-dimethylamino-2-methoxypyrimidin-5-yl)-5-(2,2,2-trifluoroethyl)-1,5-dihydro-4H-pyrazolo[4,3-c]quinolin-4-one;
compound 150: 7-[2-(5-ethyl-[1,2,4]oxadiazol-3-yl)phenyl]-5-(2,2,2-trifluoroethyl)-1,5-dihydro-4H-pyrazolo[4,3-c]quinolin-4-one;
compound 151: N-{2-[4-oxo-5-(2,2,2-trifluoroethyl)-4,5-dihydro-1H-pyrazolo[4,3-c]quinolin-7-yl]benzyl}acetamide;
compound 152: 7-[5-(hydroxyphenylmethyl)pyrid-2-yl]-5-(2,2,2-trifluoroethyl)-1,5-dihydro-4H-pyrazolo[4,3-c]quinolin-4-one;
compound 153: 6-[4-oxo-5-(2,2,2-trifluoroethyl)-4,5-dihydro-1H-pyrazolo[4,3-c]quinolin-7-yl]pyridine-2-carbonitrile;
compound 154: 7-(6-hydroxymethylpyrid-2-yl)-5-(2,2,2-trifluoroethyl)-1,5-dihydro-4H-pyrazolo[4,3-c]quinolin-4-one;
compound 155: 7-[3-(2-dimethylaminoethoxy)phenyl]-5-(2,2,2-trifluoroethyl)-1,5-dihydro-4H-pyrazolo[4,3-c]quinolin-4-one;
compound 156: methyl 2-[4-oxo-5-(2,2,2-trifluoroethyl)-4,5-dihydro-1H-pyrazolo[4,3-c]quinolin-7-yl]benzoate;
compound 157: 7-(5-hydroxymethylpyrid-2-yl)-5-(2,2,2-trifluoroethyl)-1,5-dihydro-4H-pyrazolo[4,3-c]quinolin-4-one;
compound 158: 7-(2-methoxypyrid-4-yl)-5-(2,2,2-trifluoroethyl)-1,5-dihydro-4H-pyrazolo[4,3-c]quinolin-4-one;
compound 159: 7-(2-[1,2,4]triazol-1-ylmethylphenyl)-5-(2,2,2-trifluoroethyl)-1,5-dihydro-4H-pyrazolo[4,3-c]quinolin-4-one;
compound 160: 7-(4-phenylpyrimidin-5-yl)-5-(2,2,2-trifluoroethyl)-1,5-dihydro-4H-pyrazolo[4,3-c]quinolin-4-one;
compound 161: 7-(6-methoxy-4-methylpyrid-3-yl)-5-(2,2,2-trifluoroethyl)-1,5-dihydro-4H-pyrazolo[4,3-c]quinolin-4-one;
compound 162: 7-(4-isopropylpyrimidin-5-yl)-5-(2,2,2-trifluoroethyl)-1,5-dihydro-4H-pyrazolo[4,3-c]quinolin-4-one;
compound 163: 7-(6-fluoropyrid-2-yl)-5-(2,2,2-trifluoroethyl)-1,5-dihydro-4H-pyrazolo[4,3-c]quinolin-4-one;
compound 164: methyl 6-[4-oxo-5-(2,2,2-trifluoroethyl)-4,5-dihydro-1H-pyrazolo[4,3-c]quinolin-7-yl]pyridine-2-carboxylate;
compound 165: 7-(5-fluoropyrid-2-yl)-5-(2,2,2-trifluoroethyl)-1,5-dihydro-4H-pyrazolo[4,3-c]quinolin-4-one;
compound 166: 7-[2-(4-methylpiperazin-1-yl)pyrid-3-yl]-5-(2,2,2-trifluoroethyl)-1,5-dihydro-4H-pyrazolo[4,3-c]quinolin-4-one;

compound 167: 7-(3-aminopyrid-4-yl)-5-(2,2,2-trifluoroethyl)-1,5-dihydro-4H-pyrazolo[4,3-c]quinolin-4-one;

compound 168: 7-(2,6-dimethylpyrid-4-yl)-5-(2,2,2-trifluoroethyl)-1,5-dihydro-4H-pyrazolo[4,3-c]quinolin-4-one;

compound 169: 7-(3-chloropyrid-2-yl)-5-(2,2,2-trifluoroethyl)-1,5-dihydro-4H-pyrazolo[4,3-c]quinolin-4-one;

compound 170: methyl 3-[4-oxo-5-(2,2,2-trifluoroethyl)-4,5-dihydro-1H-pyrazolo[4,3-c]quinolin-7-yl]pyridine-2-carboxylate;

compound 171: 7-(6-methylpyrid-2-yl)-5-(2,2,2-trifluoroethyl)-1,5-dihydro-4H-pyrazolo[4,3-c]quinolin-4-one;

compound 173: 5-(2,2,2-trifluoroethyl)-7-(2-trifluoromethylpyrid-3-yl)-1,5-dihydro-4H-pyrazolo[4,3-c]quinolin-4-one;

compound 175: 5-(2,2,2-trifluoroethyl)-7-(3-trifluoromethylpyrid-2-yl)-1,5-dihydro-4H-pyrazolo[4,3-c]quinolin-4-one;

compound 176: 3-[4-oxo-5-(2,2,2-trifluoroethyl)-4,5-dihydro-1H-pyrazolo[4,3-c]quinolin-7-yl]pyridine-2-carbonitrile;

compound 177: 2-[4-oxo-5-(2,2,2-trifluoroethyl)-4,5-dihydro-1H-pyrazolo[4,3-c]quinolin-7-yl]pyridine-3-carbonitrile;

compound 179: 7-(2-propoxypyrid-3-yl)-5-(2,2,2-trifluoroethyl)-1,5-dihydro-4H-pyrazolo[4,3-c]quinolin-4-one;

compound 180: 7-(3-hydroxypyrid-2-yl)-5-(2,2,2-trifluoroethyl)-1,5-dihydro-4H-pyrazolo[4,3-c]quinolin-4-one;

compound 182: 7-(2-methylaminophenyl)-5-(2,2,2-trifluoroethyl)-1,5-dihydro-4H-pyrazolo[4,3-c]quinolin-4-one;

compound 183: 7-(2-ethoxypyrid-3-yl)-5-(2,2,2-trifluoroethyl)-1,5-dihydro-4H-pyrazolo[4,3-c]quinolin-4-one;

compound 184: 7-(2-isopropoxypyrid-3-yl)-5-(2,2,2-trifluoroethyl)-1,5-dihydro-4H-pyrazolo[4,3-c]quinolin-4-one;

compound 185: 7-(5-chloro-2-methoxypyrid-3-yl)-5-(2,2,2-trifluoroethyl)-1,5-dihydro-4H-pyrazolo[4,3-c]quinolin-4-one;

compound 186: 7-(2-methylpyrid-4-yl)-5-(2,2,2-trifluoroethyl)-1,5-dihydro-4H-pyrazolo[4.3-c]quinolin-4-one;

compound 187: 7-(4-methylpyrid-2-yl)-5-(2,2,2-trifluoroethyl)-1,5-dihydro-4H-pyrazolo[4,3-c]quinolin-4-one;

compound 188: 7-(6-morpholin-4-ylpyrid-2-yl)-5-(2,2,2-trifluoroethyl)-1,5-dihydro-4H-pyrazolo[4,3-c]quinolin-4-one;

compound 189: 7-(4-methylaminophenyl)-5-(2,2,2-trifluoroethyl)-1,5-dihydro-4H-pyrazolo[4,3-c]quinolin-4-one;

compound 190: 5-(2,2,2-trifluoroethyl)-7-(6-trifluoromethylpyrid-3-yl)-1,5-dihydro-4H-pyrazolo[4,3-c]quinolin-4-one;

compound 191: 7-(6-methoxypyrid-2-yl)-5-(2,2,2-trifluoroethyl)-1,5-dihydro-4H-pyrazolo[4,3-c]quinolin-4-one;

compound 192: 7-[4-(2H-tetrazol-5-yl)phenyl]-5-(2,2,2-trifluoroethyl)-2,5-dihydro-4H-pyrazolo[4,3-c]quinolin-4-one;

compound 193: 7-(3,5-dichloropyrid-2-yl)-5-(2,2,2-trifluoroethyl)-1,5-dihydro-4H-pyrazolo[4,3-c]quinolin-4-one;

compound 194: 8-chloro-7-(pyrid-2-yl)-5-(2,2,2-trifluoroethyl)-1,5-dihydro-4H-pyrazolo[4,3-c]quinolin-4-one;

compound 195: 8-bromo-7-pyrid-2-yl-5-(2,2,2-trifluoroethyl)-1,5-dihydro-4H-pyrazolo[4,3-c]quinolin-4-one;

compound 197: 8-bromo-7-(pyrid-4-yl)-5-(2,2,2-trifluoroethyl)-2,5-dihydro-4H-pyrazolo[4,3-c]quinolin-4-one;

compound 198: 8-chloro-5-ethyl-7-pyrid-4-yl-1,5-dihydro-4H-pyrazolo[4,3-c]quinolin-4-one;

compound 199: 8-chloro-7-(2-chloropyrid-3-yl)-5-(2,2,2-trifluoroethyl)-1,5-dihydro-4H-pyrazolo[4,3-c]quinolin-4-one;

compound 200: 8-methyl-7-pyrid-2-yl-5-(2,2,2-trifluoroethyl)-1,5-dihydro-4H-pyrazolo[4,3-c]quinolin-4-one;

compound 201: 4-oxo-7-pyrid-4-yl-5-(2,2,2-trifluoroethyl)-4,5-dihydro-2H,4H-pyrazolo[4,3-c]quinoline-8-carbonitrile;

compound 202: 4-oxo-7-pyrid-4-yl-5-(2,2,2-trifluoroethyl)-4,5-dihydro-2H,4H-pyrazolo[4,3-c]quinoline-8-carboxylic acid;

compound 203: 3-[4-oxo-5-(2,2,2-trifluoroethyl)-4,5-dihydro-1H-pyrazolo[4,3-c]quinolin-7-yl]pyridine-2-carboxylic acid;

compound 204: 2-[4-oxo-5-(2,2,2-trifluoroethyl)-4,5-dihydro-1H-pyrazolo[4,3-c]quinolin-7-yl]benzoic acid;

compound 205: 4-oxo-7-(pyrid-4-yl)-5-(2,2,2-trifluoroethyl)-4,5-dihydro-2H-pyrazolo[4,3-c]quinoline-8-carboxamide;

compound 206: 7-[2-(morpholin-4-ylcarbonyl)pyrid-3-yl]-5-(2,2,2-trifluoroethyl)-1,5-dihydro-4H-pyrazolo[4,3-c]quinolin-4-one;

compound 207: N-[2-(dimethylamino)ethyl]-N-methyl-2-[4-oxo-5-(2,2,2-trifluoroethyl)-4,5-dihydro-1H-pyrazolo[4,3-c]quinolin-7-yl]benzamide;

compound 208: N-(2-dimethyaminoethyl)-N-ethyl-2-[4-oxo-5-(2,2,2-trifluoroethyl)-4,5-dihydro-1H-pyrazolo[4,3-c]quinolin-7-yl]benzamide;

compound 211: N-(3-carbamoylphenyl)-2-[4-oxo-5-(2,2,2-trifluoroethyl)-4,5-dihydro-1H-pyrazolo[4,3-c]quinolin-7-yl]benzamide;

compound 213: N,N-dimethyl-3-[4-oxo-5-(2,2,2-trifluoroethyl)-4,5-dihydro-1H-pyrazolo[4,3-c]quinolin-7-yl]pyridine-2-carboxamide;

compound 215: N-[2-(dimethylamino)ethyl]-N-methyl-3-[4-oxo-5-(2,2,2-trifluoroethyl)-4,5-dihydro-1H-pyrazolo[4,3-c]quinolin-7-yl]pyridine-2-carboxamide;

compound 216: 7-[2-(1,4-oxazepan-4-ylcarbonyl)pyrid-3-yl]-5-(2,2,2-trifluoroethyl)-1,5-dihydro-4H-pyrazolo[4,3-c]quinolin-4-one;

compound 217: N-methyl-3-[4-oxo-5-(2,2,2-trifluoroethyl)-4,5-dihydro-1H-pyrazolo[4,3-c]quinolin-7-yl]pyridine-2-carboxamide;

compound 220: 3-[4-oxo-5-(2,2,2-trifluoroethyl)-4,5-dihydro-1H-pyrazolo[4,3-c]quinolin-7-yl]pyridine-2-carboxamide;

compound 221: N-[2-(dimethylamino)ethyl]-N-ethyl-3-[4-oxo-5-(2,2,2-trifluoroethyl)-4,5-dihydro-1H-pyrazolo[4,3-c]quinolin-7-yl]pyridine-2-carboxamide;

compound 222: 7-[2-((2S,6R)-2,6-dimethylmorpholine-4-carbonyl)pyrid-3-yl]-5-(2,2,2-trifluoroethyl)-1,5-dihydro-4H-pyrazolo[4,3-c]quinolin-4-one;

compound 226: N-{-4-[4-oxo-5-(2,2,2-trifluoroethyl)-4,5-dihydro-1H-pyrazolo[4,3-c]quinolin-7-yl]pyrid-3-yl}acetamide;

compound 227: N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 228: 2-methoxy-N-{-4-[4-oxo-5-(2,2,2-trifluoroethyl)-4,5-dihydro-1H-pyrazolo[4,3-c]quinolin-7-yl]pyrid-3-yl}-2-phenylacetamide;

compound 229: N-{-4-[4-oxo-5-(2,2,2-trifluoroethyl)-4,5-dihydro-1H-pyrazolo[4,3-c]quinolin-7-yl]pyrid-3-yl}-2-phenylpropionamide;

compound 238: 3-chloro-N-{4-[4-oxo-5-(2,2,2-trifluoroethyl)-4,5-dihydro-1H-pyrazolo[4,3-c]quinolin-7-yl]pyrid-3-yl}benzenesulfonamide;

compound 239: N-(4-methoxy-3-{4-[4-oxo-5-(2,2,2-trifluoroethyl)-4,5-dihydro-1H-pyrazolo[4,3-c]quinolin-7-yl]pyrid-3-ylsulfamoyl}benzyl)acetamide;

compound 241: N-methyl-N-{3-[4-oxo-5-(2,2,2-trifluoroethyl)-4,5-dihydro-1H-pyrazolo[4,3-c]quinolin-7-yl]pyrid-2-yl}acetamide;

compound 242: N-methyl-N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 243: 7-[2-(methylamino)pyrid-3-yl]-5-(2,2,2-trifluoroethyl)-1,5-dihydro-4H-pyrazolo[4,3-c]quinolin-4-one;

compound 244: 7-[2-(1,4-diazepan-1-yl)pyrid-3-yl]-5-(2,2,2-trifluoroethyl)-1,5-dihydro-4H-pyrazolo[4,3-c]quinolin-4-one;

compound 245: 7-(3,4,5,6-tetrahydro-2H-[1,2']bipyridinyl-3'-yl)-5-(2,2,2-trifluoroethyl)-2,5-dihydro-4H-pyrazolo[4,3-c]quinolin-4-one;

compound 246: 7-[2-(3-hydroxypyrrolidin-1-yl)pyrid-3-yl]-5-(2,2,2-trifluoroethyl)-1,5-dihydro-4H-pyrazolo[4,3-c]quinolin-4-one;

compound 247: 7-[2-(3,4-dihydroxypyrrolidin-1-yl)pyrid-3-yl]-5-(2,2,2-trifluoroethyl)-2,5-dihydro-4H-pyrazolo[4,3-c]quinolin-4-one;

compound 248: 7-[2-(dimethylamino)pyrid-3-yl]-5-(2,2,2-trifluoroethyl)-1,5-dihydro-4H-pyrazolo[4,3-c]quinolin-4-one;

compound 249: 7-{2-[ethyl(methyl)amino]pyrid-3-yl}-5-(2,2,2-trifluoroethyl)-1,5-dihydro-4H-pyrazolo[4,3-c]quinolin-4-one;

compound 250: 7-{2-[(2-hydroxyethyl)(methyl)amino]pyrid-3-yl}-5-(2,2,2-trifluoroethyl)-1,5-dihydro-4H-pyrazolo[4,3-c]quinolin-4-one;

compound 251: 7-[2-(pyrrolidin-1-yl)pyrid-3-yl]-5-(2,2,2-trifluoroethyl)-1,5-dihydro-4H-pyrazolo[4,3-c]quinolin-4-one;

compound 252: 7-[2-(1,4-oxazepan-4-yl)pyrid-3-yl]-5-(2,2,2-trifluoroethyl)-1,5-dihydro-4H-pyrazolo[4,3-c]quinolin-4-one;

compound 253: 7-[2-(3-oxopiperazin-1-yl)pyrid-3-yl]-5-(2,2,2-trifluoroethyl)-1,5-dihydro-4H-pyrazolo[4,3-c]quinolin-4-one;

compound 254: 7-[2-(azetidin-1-yl)pyrid-3-yl]-5-(2,2,2-trifluoroethyl)-1,5-dihydro-4H-pyrazolo[4,3-c]quinolin-4-one;

compound 255: 7-{2-[(2-methoxyethyl)methylamino]pyrid-3-yl}-5-(2,2,2-trifluoroethyl)-2,5-dihydro-4H-pyrazolo[4,3-c]quinolin-4-one;

compound 256: 7-[2-(4-acetylpiperazin-1-yl)pyrid-3-yl]-5-(2,2,2-trifluoroethyl)-2,5-dihydro-4H-pyrazolo[4,3-c]quinolin-4-one;

compound 257: 7-[2-(diethylamino)pyrid-3-yl]-5-(2,2,2-trifluoroethyl)-1,5-dihydro-4H-pyrazolo[4,3-c]quinolin-4-one;

compound 258: 7-[2-(cyclobutylamino)pyrid-3-yl]-5-(2,2,2-trifluoroethyl)-1,5-dihydro-4H-pyrazolo[4,3-c]quinolin-4-one;

compound 259: 7-[2-(2,6-dimethylmorpholin-4-yl)pyrid-3-yl]-5-(2,2,2-trifluoroethyl)-2,5-dihydro-4H-pyrazolo[4,3-c]quinolin-4-one;

compound 260: 7-[2-(4-cyclopropylpiperazin-1-yl)pyrid-4-yl]-5-(2,2,2-trifluoroethyl)-2,5-dihydro-4H-pyrazolo[4,3-c]quinolin-4-one;

compound 261: 7-(2-cyclohexylaminopyrid-3-yl)-5-(2,2,2-trifluoroethyl)-2,5-dihydro-4H-pyrazolo[4,3-c]quinolin-4-one;

compound 262: 7-[2-(isopropylmethylamino)pyrid-3-yl]-5-(2,2,2-trifluoroethyl)-2,5-dihydro-4H-pyrazolo[4,3-c]quinolin-4-one;

compound 263: 7-(2-cyclopentylaminopyrid-3-yl)-5-(2,2,2-trifluoroethyl)-2,5-dihydro-4H-pyrazolo[4,3-c]quinolin-4-one;

compound 264: 7-(6-pyrrolidin-1-ylpyrid-2-yl)-5-(2,2,2-trifluoroethyl)-2,5-dihydro-4H-pyrazolo[4,3-c]quinolin-4-one;

compound 265: 7-[6-(2,6-dimethylmorpholin-4-yl)pyrid-2-yl]-5-(2,2,2-trifluoroethyl)-2,5-dihydro-4H-pyrazolo[4,3-c]quinolin-4-one;

compound 266: 7-{2-[cyclohexyl(methyl)amino]pyrid-3-yl}-5-(2,2,2-trifluoroethyl)-1,5-dihydro-4H-pyrazolo[4,3-c]quinolin-4-one;

compound 267: 7-[2-(4-cyclopropylpiperazin-1-yl)pyrid-3-yl]-5-(2,2,2-trifluoroethyl)-2,5-dihydro-4H-pyrazolo[4,3-c]quinolin-4-one;

compound 268: 7-[3-(4-cyclopropylpiperazin-1-yl)phenyl]-5-(2,2,2-trifluoroethyl)-1,5-dihydro-4H-pyrazolo[4,3-c]quinolin-4-one;

compound 269: 7-[2-(4-acetyl-1,4-diazepan-1-yl)pyrid-3-yl]-5-(2,2,2-trifluoroethyl)-1,5-dihydro-4H-pyrazolo[4,3-c]quinolin-4-one;

compound 270: 7-[2-(4-methyl-1,4-diazepan-1-yl)pyrid-3-yl]-5-(2,2,2-trifluoroethyl)-1,5-dihydro-4H-pyrazolo[4,3-c]quinolin-4-one;

compound 271: 7-[2-(4-cyclopropyl-[1,4]diazepan-1-yl)pyrid-3-yl]-5-(2,2,2-trifluoroethyl)-2,5-dihydro-4H-pyrazolo[4,3-c]quinolin-4-one;

compound 272: 7-[2-(3-fluoropyrrolidin-1-yl)pyrid-3-yl]-5-(2,2,2-trifluoroethyl)-2,5-dihydro-4H-pyrazolo[4,3-c]quinolin-4-one;

compound 273: 7-[2-(4-fluoropiperidin-1-yl)pyrid-3-yl]-5-(2,2,2-trifluoroethyl)-1,5-dihydro-4H-pyrazolo[4,3-c]quinolin-4-one;

compound 274: 7-(2-hydroxypyrid-3-yl)-5-(2,2,2-trifluoroethyl)-1,5-dihydro-4H-pyrazolo[4,3-c]quinolin-4-one;

compound 275: 7-(1-oxypyrid-2-yl)-5-(2,2,2-trifluoroethyl)-1,5-dihydro-4H-pyrazolo[4,3-c]quinolin-4-one;

compound 276: 7-(1-oxypyrid-4-yl)-5-(2,2,2-trifluoroethyl)-1,5-dihydro-4H-pyrazolo[4,3-c]quinolin-4-one;

in the form of the base or of an acid-addition salt, and also in hydrate form.

Among the compounds of formula (I) that are subjects of the invention, mention may be made especially of the following compounds:

compound 1: 7-(pyrid-2-yl)-5-(2,2,2-trifluoroethyl)-1,5-dihydro-4H-pyrazolo[4,3-c]quinolin-4-one;

compound 2: 7-(2-aminopyrid-3-yl)-5-(2,2,2-trifluoroethyl)-1,5-dihydro-4H-pyrazolo[4,3-c]quinolin-4-one;

compound 6: 7-(pyrid-4-yl)-5-(2,2,2-trifluoroethyl)-1,5-dihydro-4H-pyrazolo[4,3-c]quinolin-4-one;

compound 19: 7-[4-(4-methylpiperazin-1-yl)phenyl]-5-(2,2,2-trifluoroethyl)-1,5-dihydro-4H-pyrazolo[4,3-c]quinolin-4-one;

compound 67: 5-ethyl-7-[6-(piperazin-1-yl)pyrid-3-yl]-1,5-dihydro-4H-pyrazolo[4,3-c]quinolin-4-one;

compound 68: 7-[2-(4-methylpiperazin-1-yl)pyrid-4-yl]-5-(2,2,2-trifluoroethyl)-1,5-dihydro-4H-pyrazolo[4,3-c]quinolin-4-one;

compound 69: 5-ethyl-7-[2-(4-methylpiperazin-1-yl)pyrid-4-yl]-1,5-dihydro-4H-pyrazolo[4,3-c]quinolin-4-one;

compound 72: 7-(2-methyl pyrid-3-yl)-5-(2,2,2-trifluoroethyl)-1,5-dihydro-4H-pyrazolo[4,3-c]quinolin-4-one;

compound 74: 7-(2-chloro-6-methylpyrid-3-yl)-5-ethyl-1,5-dihydro-4H-pyrazolo[4,3-c]quinolin-4-one;

compound 75: 7-(2-chloro-6-methylpyrid-3-yl)-5-(2,2,2-trifluoroethyl)-1,5-dihydro-4H-pyrazolo[4,3-c]quinolin-4-one;

compound 76: 7-(2-chloropyrid-4-yl)-5-(2,2,2-trifluoroethyl)-1,5-dihydro-4H-pyrazolo[4,3-c]quinolin-4-one;

compound 77: 7-(2-fluoropyrid-3-yl)-5-(2,2,2-trifluoroethyl)-1,5-dihydro-4H-pyrazolo[4,3-c]quinolin-4-one;

compound 79: 7-(6-chloro-2-methylpyrid-3-yl)-5-(2,2,2-trifluoroethyl)-1,5-dihydro-4H-pyrazolo[4,3-c]quinolin-4-one;

compound 83: 7-[6-(morpholin-4-yl)pyrid-3-yl]-5-(2,2,2-trifluoroethyl)-1,5-dihydro-4H-pyrazolo[4,3-c]quinolin-4-one;

compound 88: 7-(6-chloropyrid-3-yl)-5-(2,2,2-trifluoroethyl)-1,5-dihydro-4H-pyrazolo[4,3-c]quinolin-4-one;

compound 111: 7-(2-chloropyrid-3-yl)-5-(2,2,2-trifluoroethyl)-1,5-dihydro-4H-pyrazolo[4,3-c]quinolin-4-one;

compound 168: 7-(2,6-dimethylpyrid-4-yl)-5-(2,2,2-trifluoroethyl)-1,5-dihydro-4H-pyrazolo[4,3-c]quinolin-4-one;

compound 169: 7-(3-chloropyrid-2-yl)-5-(2,2,2-trifluoroethyl)-1,5-dihydro-4H-pyrazolo[4,3-c]quinolin-4-one;

compound 171: 7-(1-methylpyrid-2-yl)-5-(2,2,2-trifluoroethyl)-1,5-dihydro-4H-pyrazolo[4,3-c]quinolin-4-one;

compound 172: 7-[2-(morpholin-4-yl)pyrid-3-yl]-5-(2,2,2-trifluoroethyl)-1,5-dihydro-4H-pyrazolo[4,3-c]quinolin-4-one;

compound 176: 3-[4-oxo-5-(2,2,2-trifluoroethyl)-4,5-dihydro-1H-pyrazolo[4,3-c]quinolin-7-yl]pyridine-2-carbonitrile;

compound 186: 7-(2-methylpyrid-4-yl)-5-(2,2,2-trifluoroethyl)-1,5-dihydro-4H-pyrazolo[4,3-c]quinolin-4-one;

compound 196: 8-chloro-7-(pyrid-4-yl)-5-(2,2,2-trifluoroethyl)-1,5-dihydro-4H-pyrazolo[4,3-c]quinolin-4-one;

compound 199: 8-chloro-7-(2-chloropyrid-3-yl)-5-(2,2,2-trifluoroethyl)-1,5-dihydro-4H-pyrazolo[4,3-c]quinolin-4-one;

compound 209: 7-{2-[(4-methyl-1,4-diazepan-1-yl)carbonyl]phenyl}-5-(2,2,2-trifluoroethyl)-1,5-dihydro-4H-pyrazolo[4,3-c]quinolin-4-one;

compound 232: N-{2-[4-oxo-5-(2,2,2-trifluoroethyl)-4,5-dihydro-2H-pyrazolo[4,3-c]quinolin-7-yl]phenyl}methanesulfonamide;

compound 248: 7-[2-(dimethylamino)pyrid-3-yl]-5-(2,2,2-trifluoroethyl)-1,5-dihydro-4H-pyrazolo[4,3-c]quinolin-4-one;

compound 251: 7-[2-(pyrrolidin-1-yl)pyrid-3-yl]-5-(2,2,2-trifluoroethyl)-1,5-dihydro-4H-pyrazolo[4,3-c]quinolin-4-one;

compound 257: 7-[2-(diethylamino)pyrid-3-yl]-5-(2,2,2-trifluoroethyl)-1,5-dihydro-4H-pyrazolo[4,3-c]quinolin-4-one;

compound 273: 7-[2-(4-fluoropiperidin-1-yl)pyrid-3-yl]-5-(2,2,2-trifluoroethyl)-1,5-dihydro-4H-pyrazolo[4,3-c]quinolin-4-one; in the form of the base or of an acid-addition salt, and also in hydrate form.

Among the compounds of formula (I) that are subjects of the invention, mention may be made especially of the following compounds:

compound 1: 7-(pyrid-2-yl)-5-(2,2,2-trifluoroethyl)-1,5-dihydro-4H-pyrazolo[4,3-c]quinolin-4-one;

compound 6: 7-(pyrid-4-yl)-5-(2,2,2-trifluoroethyl)-1,5-dihydro-4H-pyrazolo[4,3-c]quinolin-4-one;

compound 67: 5-ethyl-7-[6-(piperazin-1-yl)pyrid-3-yl]-1,5-dihydro-4H-pyrazolo[4,3-c]quinolin-4-one;

compound 69: 5-ethyl-7-[2-(4-methylpiperazin-1-yl)pyrid-4-yl]-1,5-dihydro-4H-pyrazolo[4,3-c]quinolin-4-one;

compound 72: 7-(2-methylpyrid-3-yl)-5-(2,2,2-trifluoroethyl)-1,5-dihydro-4H-pyrazolo[4,3-c]quinolin-4-one;

compound 74: 7-(2-chloro-6-methylpyrid-3-yl)-5-ethyl-1,5-dihydro-4H-pyrazolo[4,3-c]quinolin-4-one;

compound 75: 7-(2-chloro-6-methylpyrid-3-yl)-5-(2,2,2-trifluoroethyl)-1,5-dihydro-4H-pyrazolo[4,3-c]quinolin-4-one;

compound 76: 7-(2-chloropyrid-4-yl)-5-(2,2,2-trifluoroethyl)-1,5-dihydro-4H-pyrazolo[4,3-c]quinolin-4-one;

compound 77: 7-(2-fluoropyrid-3-yl)-5-(2,2,2-trifluoroethyl)-1,5-dihydro-4H-pyrazolo[4,3-c]quinolin-4-one;

compound 79: 7-(6-chloro-2-methylpyrid-3-yl)-5-(2,2,2-trifluoroethyl)-1,5-dihydro-4H-pyrazolo[4,3-c]quinolin-4-one;

compound 88: 7-(6-chloropyrid-3-yl)-5-(2,2,2-trifluoroethyl)-1,5-dihydro-4H-pyrazolo[4,3-c]quinolin-4-one;

compound 111: 7-(2-chloropyrid-3-yl)-5-(2,2,2-trifluoroethyl)-1,5-dihydro-4H-pyrazolo[4,3-c]quinolin-4-one;

compound 168: 7-(2,6-dimethylpyrid-4-yl)-5-(2,2,2-trifluoroethyl)-1,5-dihydro-4H-pyrazolo[4,3-c]quinolin-4-one;

compound 169: 7-(3-chloropyrid-2-yl)-5-(2,2,2-trifluoroethyl)-1,5-dihydro-4H-pyrazolo[4,3-c]quinolin-4-one;

compound 171: 7-(6-methylpyrid-2-yl)-5-(2,2,2-trifluoroethyl)-1,5-dihydro-4H-pyrazolo[4,3-c]quinolin-4-one;

compound 176: 3-[4-oxo-5-(2,2,2-trifluoroethyl)-4,5-dihydro-1H-pyrazolo[4,3-c]quinolin-7-yl]pyridine-2-carbonitrile;

compound 186: 7-(2-methylpyrid-4-yl)-5-(2,2,2-trifluoroethyl)-1,5-dihydro-4H-pyrazolo[4,3-c]quinolin-4-one;

compound 199: 8-chloro-7-(2-chloropyrid-3-yl-5-(2,2,2-trifluoroethyl)-1,5-dihydro-4H-pyrazolo[4,3-c]quinolin-4-one;

compound 248: 7-[2-(dimethylamino)pyrid-3-yl]-5-(2,2,2-trifluoroethyl)-1,5-dihydro-4H-pyrazolo[4,3-c]quinolin-4-one;

compound 251: 7-[2-(pyrrolidin-1-yl)pyrid-3-yl]-5-(2,2,2-trifluoroethyl)-1,5-dihydro-4H-pyrazolo[4,3-c]quinolin-4-one;

compound 257: 7-[2-(diethylamino)pyrid-3-yl]-5-(2,2,2-trifluoroethyl)-1,5-dihydro-4H-pyrazolo[4,3-c]quinolin-4-one;

compound 273: 7-[2-(4-fluoropiperidin-1-yl)pyrid-3-yl]-5-(2,2,2-trifluoroethyl)-1,5-dihydro-4H-pyrazolo[4,3-c]quinolin-4-one;

in the form of the base or of an acid-addition salt, and also in hydrate form.

In the text hereinbelow, the term "protecting group PG" means a group that can, firstly, protect a reactive function such as a pendent hydroxyl or amine during a synthesis and, secondly, regenerate the intact reactive function at the end of the synthesis. Examples of protecting groups and of protection and deprotection methods are given in "Protective Groups in Organic Synthesis", Greene et al., 3$^{rd}$ Edition (John Wiley & Sons, Inc., New York).

In the text hereinbelow, the term "leaving group LG" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a mesyl, tosyl, triflate, acetyl, etc. Examples of leaving groups and references for preparing them are given in "Advanced Organic Chemistry", J. March, 3$^{rd}$ Edition, Wiley Interscience, pp. 310-316, In accordance with the invention, the compounds of general formula (I) may be prepared according to the processes that follow.

Unless otherwise mentioned, R1, R2 and R3 are as defined previously.

Unless otherwise mentioned, the group Hal represents a bromine, iodine or chlorine atom, more particularly a bromine or iodine atom.

Scheme 1: preparation of an intermediate 1,5 dihydro-4H-pyrazolo[4,3-c]quinolin-4-one of formula (VI)

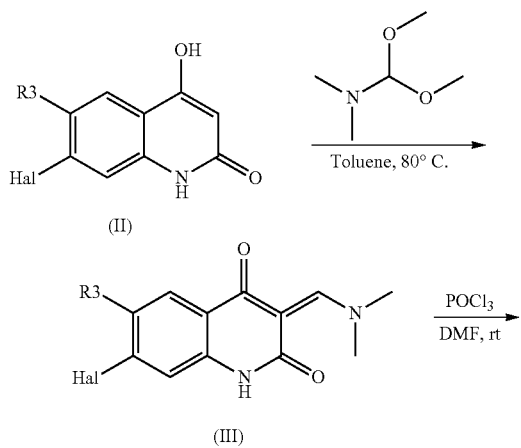

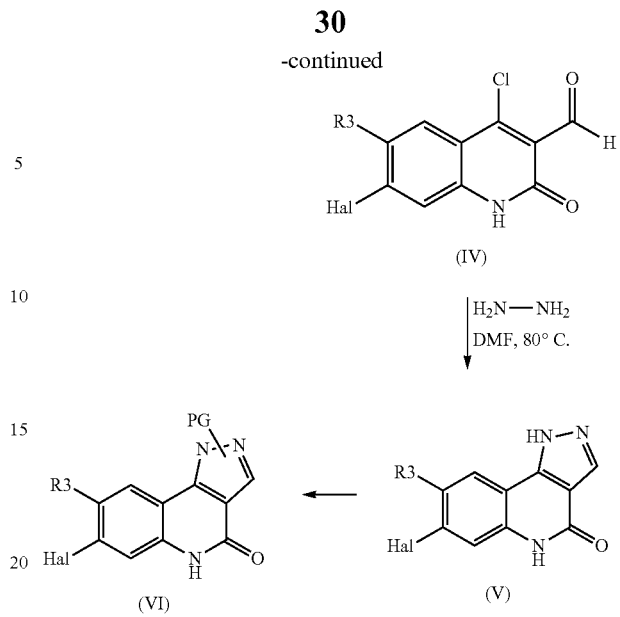

Scheme 1 illustrates the synthesis of the key intermediate of formula (VI). The reaction of a 4-hydroxyquinolin-2(1H)-one derivative of formula (II) [obtained according to or after adaptation of the processes described in *Bioorganic & Medicinal Chemistry*, 2005, 13(4), 1069-1081] with N,N-dimethylformamide dimethyl acetal (DMFDMA) gives the enamine of formula (III) [according to an adaptation of the process described in *Tetrahedron*, 2004, 60(39), 8633-8644]. Treatment of compound (III) with POCl$_3$ at room temperature in an inert solvent such as DMF gives the derivative 4-chloro-2-oxo-1,2-dihydroquinoline-3-carbaldehyde of formula (IV) after aqueous work-up. The term "room temperature" means a temperature of between 5 and 25° C. Condensation of hydrazine with the chloro-aldehyde of formula (IV) generates 1,5-dihydro-4H-pyrazolo[4,3-c]quinolin-4-one of formula (V) in a solvent such as DMF. THF or ethanol, working at a temperature between room temperature and 100° C. and preferably by heating to 80° C. The pyrazole may be selectively protected with a protecting group that is stable in basic medium such as SEM or THP to give the intermediate of formula (VI).

Scheme 2 (routes A & B): production of the compounds of formula (I) from the intermediate of formula (VI)

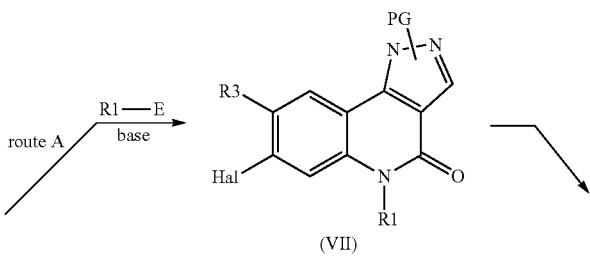

-continued

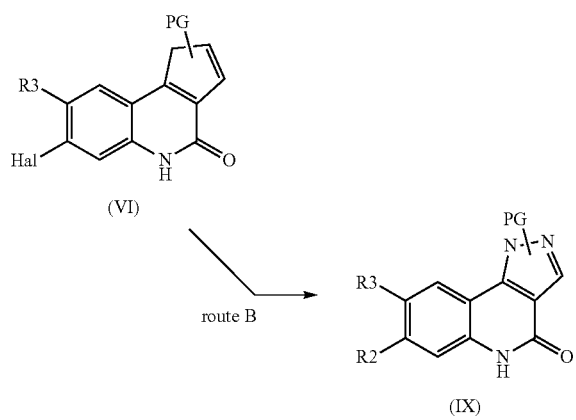

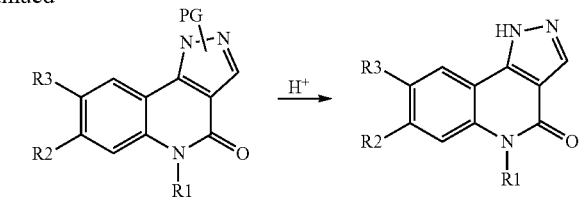

As indicated in Scheme 2, the compounds of formula (I) in which the group R2 is —O-pyridine or —NH-pyridine or -A-X as defined previously, and with the exception of the case where R3 represents CO₂H, may be obtained according to the following routes:

route A: 1,5-dihydro-4H-pyrazolo[4,3-c]quinolin-4-one of formula (VI) may be alkylated with an electrophile R1-E in which E is a good leaving group such as a halogen or a triflate, in the presence of a base such as sodium hydride, potassium tert-butoxide or sodium, potassium or caesium carbonate, in an inert solvent such as DMF or THF, at room temperature or by heating to 80° C. The N-alkyl compound of formula (VII) is predominant and its O-alkyl isomer is obtained in an amount of up to 30% depending on the electrophile and the base used.

The halogenated derivative of formula (VII) may be engaged:

either in an organometallic coupling reaction catalysed with palladium, for example PdCl₂(dppf), either with boronic acids or esters or with tin derivatives, in the presence or absence of a phosphine ligand and/or of a weak base in a solvent such as DMF, by heating to between 80 and 150° C., to give the compounds of formula (VIII) with R2 being a group -A-X—;

or in a coupling reaction with hydroxypyridine or aminopyridine derivatives catalysed with copper in the presence or absence of a ligand and/or of a weak base, to give the compounds of formula (VIII) with R2 being a group —O-pyridine or —NH-pyridine.

Finally, the compounds of formula (I) are obtained after deprotection of the pyrazole of the compounds of formula (VIII) under suitable conditions according to the protecting group PG. For example, when PG represents SEM or THP in the compounds of formula (VIII), a treatment in acidic medium, for example with TFA or anhydrous dilute HCl, makes it possible to obtain the compounds of formula (I).

route B: the halogenated derivative of formula (VI) may be engaged in an organometallic coupling reaction either with boronic acids or esters or tin derivatives, or with hydroxypyridine or aminopyridine derivatives with R2 being a group -A-X or —O-pyridine or —NH-pyridine, respectively, to give a compound of formula (IX), which may then be alkylated with an electrophile R1-E in the presence of a base as described in route A above.

Scheme 3 (route C): preparation of an intermediate 1,5-dihydro-4H-pyrazolo[4,3-c]quinolin-4-one of formula (XIV) and production of the compounds of formula (I)

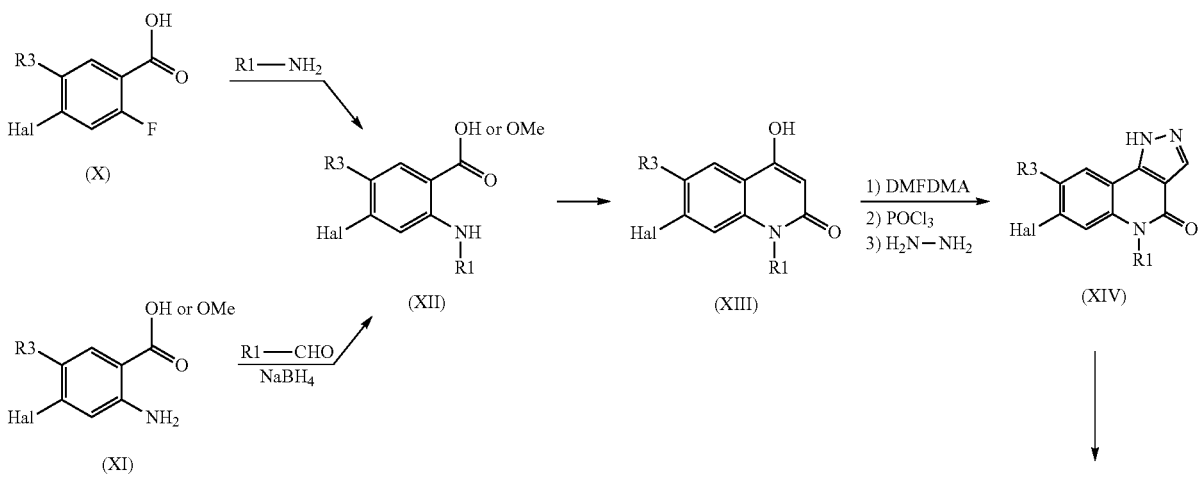

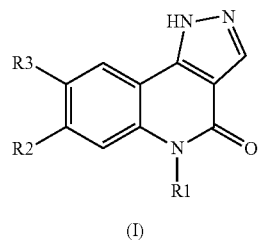

(I)

An alternative to the introduction of the substituent R1 by N-alkylation of the intermediates of formula (VI) or (IX) with an electrophile R1-E (see routes A and B above) consists in introducing the group R1 via substitution of the fluorine atom of the compounds of formula (X), with the exception of the cases where R3 represents a fluorine atom, via the amine R1-NH₂ as described in *J. Med. Chem.*, 2008, 51(6), 1925-1944, or by reductive amination with the aldehyde R1-CHO of the anilines of formula (XI), as indicated in Scheme 3. The compounds of formula (XII) obtained are converted into compounds of formula (XI(I) according to the processes described for preparing the compounds of formula (II). The processes for converting the compounds of formula (II) into compounds of formula (V) are used for converting the compounds of formula (XIII) into compounds of formula (XIV). The compounds of formula (I) are obtained directly from the compounds of formula (XIV) via:

- either an organometallic coupling reaction catalysed with palladium, for example with PdCl₂(dppf), either with boronic acids or esters or with tin derivatives in the presence of a phosphine ligand and/or a weak base in a solvent such as DMF with heating to between 80 and 150° C. The compounds of formula (I) are thus obtained with R2 being a group -A-X.

- or a coupling reaction with hydroxypyridine or aminopyridine derivatives catalysed with copper in the presence of a ligand and/or a weak base, to give the compounds of formula (I) with R2 being a group —O-pyridine or —NH-pyridine.

Scheme 4 (route D): preparation of an intermediate 1,5-dihydro-4H-pyrazolo [4,3-c]quinolin-4-one of formula (VII) via an intramolecular Heck reaction

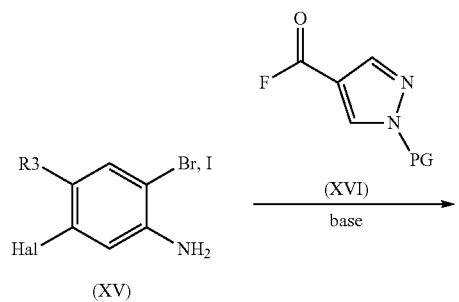

Scheme 4 illustrates an alternative route for the synthesis of the compound of formula (VII), which intermediate may be used as described in Scheme 2 for preparing the compounds of formula (I). The anilines of formula (XV) react with an acid chloride of formula (XVI) comprising a protecting group that is stable in basic medium such as SEM or THP in the presence of a base such as tBuOK or NaH in a solvent such as THF or DMF, at room temperature, to give the amide of formula (XVII). The amide of formula (XVII) may be alkylated with an electrophilic group R1-E in which E is a good leaving group such as a halogen or a triflate, in the presence of a base such as sodium hydride, potassium tert-butoxide or sodium, potassium or caesium carbonate, in an inert solvent such as DMF or THF, at room temperature or by heating up to 80° C. The N-alkyl compound of formula (XVIII) predominantly obtained versus its O-alkyl isomer is then engaged in an intramolecular Heck reaction catalysed with palladium, for example with Pd(PPh₃)₄, in the presence of a weak base such as triethylamine or potassium acetate, in a solvent such as DMF, while heating to between 60 and 120° C. to give the protected 1,5-dihydro-4H-pyrazolo[4,3-c]quinolin-4-one of formula (VII).

Scheme 5 (route E): alternative to the preparation of the compounds of formula (I) via the intermediates of formulae (VII) and (XIV)

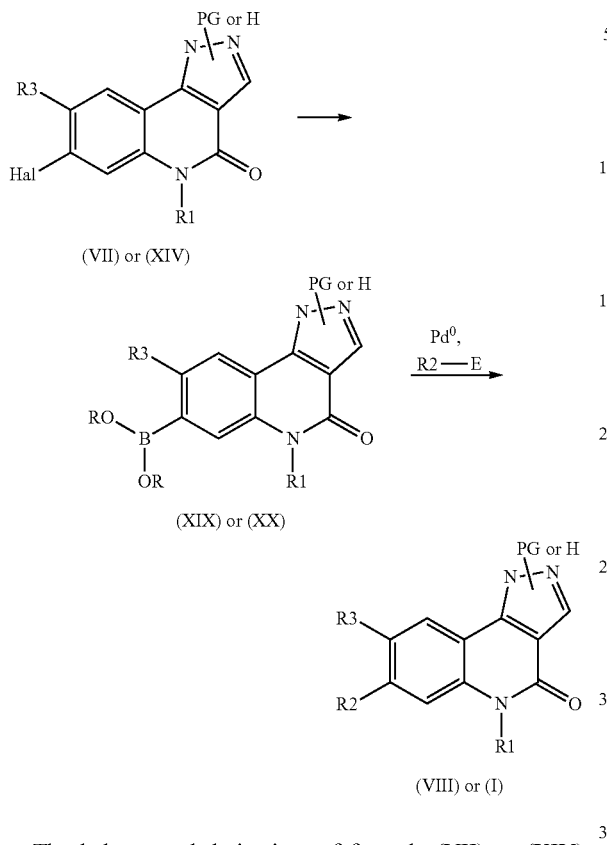

(VII) or (XIV)

(XIX) or (XX)

(VIII) or (I)

The halogenated derivatives of formula (VII) or (XIV) obtained according to the processes described in Schemes 2, 3 and 4 may be converted into the boronic acid or ester of formula (XIX) or (XX), respectively, via a palladium-catalysed coupling reaction with a diborane derivative, for example pinacol diborane. The boronic acid or ester of formula (XIX) or (XX) for which R represents a hydrogen atom or the two groups R are carbon atoms bonded together and optionally substituted with one or more (C1-C4) alkyl groups may be engaged in a palladium-catalysed Suzuki coupling reaction with aromatic compounds R2-E bearing a leaving group E such as a halogen, for instance chlorine, bromine or iodine, or a triflate group, to give, respectively, the compounds of formula (VIII) that allow preparation of the compounds of formula (I) as described previously, or directly the compound of formula (I).

Scheme 6 (route F): functionalization in position 8 of the 1,5-dihydro-4H-pyrazolo[4,3-c]quinolin-4-ones with R3 representing a halogen

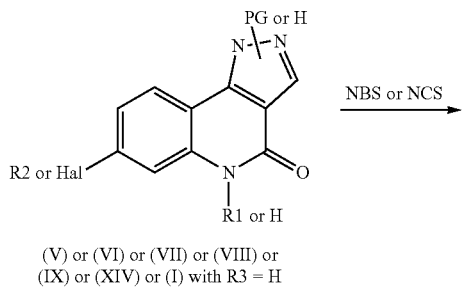

(V) or (VI) or (VII) or (VIII) or (IX) or (XIV) or (I) with R3 = H

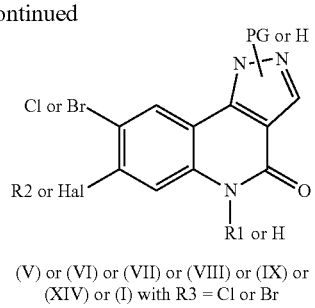

(V) or (VI) or (VII) or (VIII) or (IX) or (XIV) or (I) with R3 = Cl or Br

As indicated in Scheme 6, the regioselective introduction of a halogen atom into position 8 of the 1,5-dihydro-4H-pyrazolo[4,3-c]quinolin-4-one compounds of formula (V) or (VI) or (VII) or (VIII) or (IX) or (XIV) or (I) when R3 is a hydrogen, may be performed via an aromatic electrophilic substitution reaction with reagents such as, for example, NBS or NCS in the presence or absence of a catalyst such as palladium, for example Pd(OAc)$_2$, in the presence or absence of an acid such as dry acetic acid, with heating from 60 to 120° C.

Scheme 7 (route G): functionalization in position 8 of the 1,5-dihydro-4H-pyrazolo[4,3-c]quinolin-4-ones with R3 representing —Me or —CN

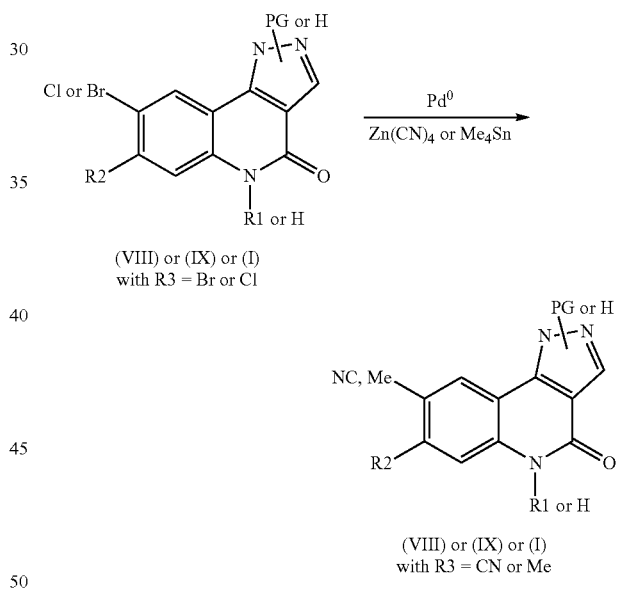

(VIII) or (IX) or (I) with R3 = Br or Cl (VIII) or (IX) or (I) with R3 = CN or Me When R3 is a chlorine or bromine atom, the halogenated derivative of formula (VIII) or (IX) or (I) may be engaged in a palladium-catalysed coupling reaction with tetramethyltin to give the compound of formula (VIII) or (IX) or (I) with R3 being a methyl group, or alternatively with zinc cyanide to give the compound of formula (VIII) or (IX) or (I) with R3 being a nitrile group.

When X and/or R3 contains or represents a cyano group, it may be hydrolysed to a group —COORa with Ra being H or a primary amide, according to processes that are well known to those skilled in the art (route H).

When X contains or represents a group —COORa with Ra other than H, it may be converted by saponification into a group —COORa with Ra being H (route I).

When X and/or R3 contains or represents a group —COORa with Ra being H, it may be coupled, after activation, to an amine or to ammonium bicarbonate or to a heterocycle or to a heteroaryl comprising an —NH function, to give a group —CONRaRb with Ra=Rb=H for R3 and/or a group —CONRaRb, —C(O)—NRa—(CH2)n-O—Rb, —C(O)—NRa-aryl-C(O)—NRaRb, —C(O)—NRa—(CH2)n-NRaRb, —C(O)—NRa—(CH2)n-heteroaryl, —CO-heterocycle or —CO-heteroaryl for X (route J).

When X contains or represents a group —NRaRb with Rb being H, it may be coupled with an activated carboxylic acid derivative in the presence of a weak base, to give a group —NRaC(O)—(C1-C6)alkyl, —NRa—C(O)—(CH2)n-NRaRb, —NRa—C(O)-aryl, —NRa—C(O)—(C1-C6)alkyl-aryl or —NRa—C(O)—(CH2)n-O—Rb (route K).

When X contains or represents a group —NRaRb with Rb being H, it may react with a sulfonyl chloride in the presence of a weak base to give a group —NRa—SO2-(CH2)n-aryl, —NRa—SO2-(CH2)n-NRaRb, —NRa—SO2-Rb, —NRa—SO2-aryl-O-aryl or —NRa—SO2-aryl (CH2)n-NRa—C(O)—Rb (route L).

When X contains or represents a group —NRaC(O)—(C1-C6)alkyl, —NRa—C(O)—(CH2)n —NRaRb, —NRa—C(O)-aryl, —NRa—C(O)—(C1-C6)alkyl-aryl, —NRa—C(O)—(CH2)n-O—Rb, —NRa—SO2-(CH2)n-aryl, —NRa—SO2-(CH2)n-NRaRb, —NRa—SO2-Rb, —NRa—SO2-aryl-O-aryl or -NRa—SO2-aryl-(CH2)n-NRb—C(O)—Rb with Ra being a hydrogen, it may react with an electrophile of formula (C1-C6)alkyl-LG (LG being a leaving group) in the presence of a base to give a group —NRaC(O)—(C1-C6)alkyl, —NRa—C(O)—(CH2)n-NRaRb, —NRa—C(O)-aryl, —NRa—C(O)—(C1-C6)alkyl-aryl, —NRa—C(O)—(CH2)n-O—Rb, —NRa—SO2-(CH2)n-aryl, —NRa—SO2-(CH2)n-NRaRb, —NRa—SO2-Rb, —NRa—SO2-aryl-O-aryl or —NRa—SO2-aryl-(CH2)n-NRb—C(O)—Rb in which Ra represents (C1-C6)alkyl (route M).

When X is a halogen, it may be substituted with an amine in the presence or absence of a palladium(0) or copper(I) catalyst, in the presence or absence of a base, to give the compounds in which X represents a group NRaRb, —NRa—(CH2)n-O—Rb, —NRa-heterocycle or —NRa-aryl (route N).

When X contains a primary or secondary amine function, it may be engaged in a reductive amination reaction with an aldehyde in the presence of a reducing agent of hydride type, to give the corresponding amine (route O).

When X contains a hydroxyl function, it may be engaged in a fluorination reaction (route P).

When X represents a group —(C1-C6)alkoxy, it may be engaged in a hydrolysis reaction to give a group —O—Ra with Ra being H (route Q).

When A represents a heteroaryl, for instance a pyridine, it may be oxidized to give the N-oxide analogue of the heteroaryl (route R).

In Schemes 1-7, the starting compounds and the reagents, when their preparation method is not described, are commercially available or described in the literature, or else may be prepared according to methods that are described therein or that are known to those skilled in the art.

According to another of its aspects, a subject of the invention is also compounds of formulae (II) to (XX). These compounds are useful as intermediates for synthesizing compounds of formula (I), and more particularly the intermediates (III), (IV), (V), (VI), (VII), (VIII), (IX), (XIII), (XIV), (XVII), (XVIII), (XIX), and (XX).

The examples that follow describe the preparation of certain compounds in accordance with the invention. The examples are not limiting, but serve merely to illustrate the present invention. The table hereinbelow illustrates the chemical structures and physical properties of a number of compounds according to the invention.

The following abbreviations and empirical formulae are used:
EtOAc ethyl acetate
CuI copper iodide
DCM dichloromethane
DCE dichloroethane
DHP dihydropyranyl
DMF N,N-dimethylformamide
DMSO dimethyl sulfoxide
EtOH ethanol
HCl hydrogen chloride
HPLC high-performance liquid chromatography
LCMS liquid chromatography/mass spectrometry
MeOH methanol
MeTHF 2-methyltetrahydrofuran
MHz MegaHertz
NaH sodium hydride
NaCl sodium chloride
$NaBH_4$ sodium borohydride
$NaHCO_3$ sodium hydrogen carbonate
$Na_2SO_4$ sodium sulfate
NBS N-bromosuccinimide
NCS N-chlorosuccinimide
NMP N-methyl-2-pyrrolidone
$PdCl_2$(dppf) [1,1'-bis(diphenylphosphino)ferrocene]dichloropalladium(II)
$Pd(PPh_3)_4$ tetrakis(triphenylphosphine)palladium(0)
$Pd(\mu\text{-Br})(tBu_3P)]_2$ di-µ-bromobis(tri-tert-butylphosphine)dipalladium(I)
$Pd(OAc)_2$ palladium(II) acetate
$POCl_3$ phosphoryl chloride
tBuOK potassium tert-butoxide
TFA trifluoroacetic acid
THF tetrahydrofuran
THP tetrahydropyranyl
SEM 2-(trimethylsilyl)ethoxy]methyl
$Zn(CN)_4$ zinc cyanide
° C. degrees Celsius
min minute(s)
mL milliliter(s)
mmol millimole(s)
ppm parts per million
In the text hereinbelow:
  the proton magnetic resonance spectra ($^1$H NMR), as described below, are recorded at 400 MHz or 500 MHz in DMSO-$d_6$, using the DMSO-$d_6$ peak as reference. The chemical shifts δ are expressed in parts per million (ppm). The signals observed are expressed as follows: s=singlet; d=doublet; t=triplet; m=multiplet or br. s.=broad singlet;
  the LCMS characteristics, as described below, successively indicated the high-performance liquid chromatography analytical method used and detailed below (A to I), the MH$^+$ peak identified by mass spectrometry and the retention time of the compound, expressed in minutes.
* Method A
  Instrument: HPLC line of the type 1100 (Agilent) or Alliance (Waters); simple quadrupole mass spectrometer of the type MSD (Agilent) or ZQ (Waters)
  Column: Symmetry C18 3.5 µm (2.1×50 mm) Waters
  Solvent A: $H_2O$+0.005% TFA; Solvent B: $CH_3CN$+0.005% TFA
  Flow rate: 0.4 mL/min Gradient A/B: 100/0 (t0 min) to 0/100 (t10 min) to 0/100 (t15 min)
Detection: UV 220 nm
Ionization: electrospray positive mode ESI+
* Method B: Method A with change of gradient A/B
Gradient A/B: 100/0 (t0 min) to 0/100 (t30 min) to 0/100 (t35 min)
* Method C
Instrument: HPLC line of the type 1100 (Agilent) or Alliance (Waters); simple quadrupole mass spectrometer of the type MSD (Agilent) or ZQ (Waters)
Column: X Terra C18 3.5 µm (2.1×50 mm) Waters
Solvent A: $H_2O+NH_4OAc$ 10 mM pH 7; Solvent B; $CH_3CN$
Flow rate: 0.4 mL/min
Gradient A/B: 100/0 (t0 min) to 10/90 (t10 min) to 10/90 (t15 min)
Detection: UV 220 nm
Ionization; electrospray positive mode ESI+
* Method D
Instrument: UPLC Acquity line (Waters); SQD mass spectrometer (Waters)
Column: BEH-C18 (2.1×50 mm) 1.7 µm (Waters); column temp.: 55° C.
Solvent A: $H_2O+0.02\%$ HCOOH; Solvent B: $CH_3CN+0.02\%$ HCOOH
Flow rate: 1 mL/min
Gradient A/B: 98/2 (t0 min) to 2/98 (t4 min) to 2/98 (t4.5 min)
Detection: UV 220 nm
Ionization: electrospray positive mode ESI+
* Method E
Instrument: HPLC line of the type 1100 (Agilent) or Alliance (Waters); simple quadrupole mass spectrometer of the type MSD (Agilent) or ZQ (Waters)
Column: Luna C18(2)-HST Phenomenex (30×2 mm) 2.5 µm; column temp.: 50° C.
Solvent A: $H_2O+0.05\%$ TFA; Solvent B: $CH_3CN+0.035\%$ TFA
Flow rate: 1 mL/min
Gradient A/B: 100/0 (t0 min) to 0/100 (t2.5 min) to 0/100 (t3.5 min)
Detection: UV 220 nm
Ionization: electrospray positive mode ESI+
* Method F
Instrument: HPLC line of the type 1100 (Agilent) or Alliance (Waters); simple quadrupole mass spectrometer of the type MSD (Agilent) or ZQ (Waters)
Column: Symmetry C18 (50×2.1 mm) 3.5 µm (Waters); column temp.: 40° C.
Solvent A: $H_2O+0.05\%$ TFA; Solvent B: $CH_3CN+0.035\%$ TFA
Flow rate: 0.5 mL/min
Gradient A/B: 100/0 (t0 min) to 0/100 (t7 min)
Detection: UV 220 nm
Ionization: electrospray positive mode ESI+
* Method G
Instrument: UPLC Acquity line (Waters), SQD mass spectrometer (Waters)
Column: BEH C18 (50×2.1 mm) 17 µm (Waters); column temp.: 55° C.
Solvent A: $H_2O+0.05\%$ TFA; Solvent B: $CH_3CN+0.035\%$ TFA
Flow rate: 0.8 mL/min Gradient A/B: 98/2 (t0 min) to 0/100 (t2.4 min) to 0/100 (t3 min)
Detection: UV 220 nm
Ionization: electrospray positive mode ESI+
* Method H
Instrument: Waters UPLC
Column: BEH C18 (2.1×50 mm) 1.7 µm
Solvent A: $H_2O+0.05\%$ $HCO_2H$; Solvent B: $CH_3CN+0.035\%$ $HCO_2H$
Flow rate: 0.9 mL/min
Gradient A/B: 95/5 (t0 min) to 5/95 (t1.1 min) to 5/95 (0.7 min)
Detection: 220 nM
Ionization: electrospray positive mode ESI+
* Method H': Method H with Change of Eluents
Solvent A: $H_2O+0.1\%$ $HCO_2H$; Solvent B: $CH_3CN+0.08\%$ $HCO_2H$
Gradient A/B: 95/5 (t0 min) to 5/95 (t1.1 min) to 5/95 (t1.7 min)
* Method I
Instrument: Waters UPLC
Column: Waters XBridge C18 (4.6×50 mm) 2.5 µm
Solvent A: $H_2O+0.1\%$ $HCO_2H$; Solvent B: $CH_3CN+0.08\%$ $HCO_2H$
Gradient A/B: 97/3 (t0 min) to 40/60 (t3.5 min) to 2/98 (t4 min) to 2/98 (t5 min)
Detection: 220 nM
Ionization: electrospray positive mode ESI+
* Method I': Method H with Change of Eluents
Solvent A: $H_2O+0.05\%$ TFA; Solvent B: $CH_3CN+0.05\%$ TFA
Gradient A/B: 95/5 (t0 min) to 95/5 (t0.3 min) to 5/95 (t3.5 min) to 5/95 (t4 min)
* Method J
Instrument: Waters UPLC
Column: Jsphere (33×2.1 mm) 4 µm
Solvent A: $H_2O+0.05\%$ TFA; Solvent B: $CH_3CN+0.05\%$ TFA
Gradient A/B: 98/2 (t0 min) to 98/2 (t1 min) to 5/95 (t5 min) to 5/95 (t6.25 min)
Detection: 220 nM
Ionization: electrospray positive mode ESI+

EXAMPLE 1

7-(pyrid-2-yl)-5-(2,2,2-trifluoroethyl)-1,5-dihydro-4H-pyrazolo[4,3-c]quinolin-4-one hydrochloride (Compound 1)

Step 1.1. (3E,Z)-7-bromo-3-[(dimethylamino)methylidene]quinoline-2,4(1H,3H)-dione In a three-necked flask, N,N-dimethylformamide dimethyl acetal (103 mL, 0.77 mol) is added to a suspension of 7-bromo-4-hydroxyquinolin-2(1H)-one/12.3 g, 51.2 mmol) in 250 mL of toluene. The reaction mixture is stirred for 24 hours at 80° C., and then cooled to room temperature and filtered. The solid obtained is washed with toluene and dried under vacuum to give 13.5 g of (3E,Z)-7-bromo-3-[(dimethylamino)methylidene]quinoline-2,4(1H,3H)-dione in the form of a beige-coloured solid (yield: 89%).
LCMS (Method C): $MH^+=295.0$, RT=5.86 min Step 1.2. 7-bromo-4-chloro-2-oxo-1,2-dihydroquinoline-3-carbaldehyde Phosphoryl chloride (1.9 mL, 20.3 mmol) is added dropwise to a suspension of (3E,Z)-7-bromo-3-[(dimethylamino)methylidene]quinoline-2,4(1H,3H)-dione (5 g, 16.9 mmol) in 50 mL of DMF at 0° C. The reaction mixture is stirred for

Step 1.3. 7-bromo-1,5-dihydro-4H-pyrazolo[4,3-c]quinolin-4-one

To a solution of 7-bromo-4-chloro-2-oxo-1,2-dihydroquinoline-3-carbaldehyde (8.0 g, 27.9 mmol) in 150 mL of DMF at 80° C. is added hydrazine hydrate (2 mL, 33.5 mmol) at 80° C. The reaction medium is stirred for 24 hours at 80° C. and then cooled to room temperature and filtered. The solid obtained is washed with diisopropyl ether and dried to give 5.3 g of 7-bromo-1,5-dihydro-4H-pyrazolo[4,3-c]quinolin-4-one in the form of a pale yellow powder (yield: 72%).

LCMS (Method A): MH$^+$=264.1, RT=5,27 min

Step 1.4. 7-bromo-1-(tetrahydro-2H-pyran-2-yl)-1,5-dihydro-4H-pyrazolo[4,3-c]quinolin-4-one and 7-bromo-2-(tetrahydro-2H-pyran-2-yl)-1,5-dihydro-4H-pyrazolo[4,3-c]quinolin-4-one To a solution of 7-bromo-1,5-dihydro-4H-pyrazolo[4,3-c]quinolin-4-one (17.95 g 67.97 mmol) in 1L of DMF are added 3,4-dihydro-2H-pyran (18.6 mL, 204 mmol) and para-toluenesulfonic acid (1.29 g, 6.80 mmol) at room temperature. The reaction medium is stirred at room temperature for 72 hours and then poured into saturated NaHCO$_3$ and extracted with EtOAc. The organic phase is washed with saturated NaCl solution and dried over Na$_2$SO$_4$, filtered and concentrated to dryness to give a brown solid. The solid is taken up in diisopropyl ether and, after filtering off, 18.8 g of an orange-coloured powder (yield: 71%) are obtained.

LCMS (Method A): MH$^+$=350.1, RT=5.28 min

Step 1.5. 7-bromo-1-(tetrahydro-2H-pyran-2-yl)-5-(2,2,2-trifluoroethyl)-1,5-dihydro-4H-pyrazolo[4,3-c]quinolin-4-one and of 7-bromo-2-(tetrahydro-2H-pyran-2-yl)-5-(2,2,2-trifluoroethyl)-1,5-dihydro-4/1-pyrazolo[4,3-c]quinolin-4-one To a suspension of 7-bromo-1-(tetrahydro-2H-pyran-2-yl)-1,5-dihydro-4H-pyrazolo[4,3-c]quinolin-4-one and 7-bromo-2-(tetrahydro-2H-pyran-2-yl)-1,5-dihydro-4H-pyrazolo[4,3-c]quinolin-4-one (17.3 g, 49.7 mmol) in 170 mL of anhydrous MeTHF at 70° C. is added t-BuOK (11.2 g, 99.4 mmol) portionwise. After stirring for 15 minutes at 70° C., 2,2,2-trifluoroethyl trifluoromethanesulfonate (14.4 mL, 99.4 mmol) is added dropwise. The reaction medium is stirred for 2 hours at 70° C. after addition of 180 mL of anhydrous MeTHF. After 2 hours, a further portion of t-BuOK/11.14 g, 49.7 mmol) and of 2,2,2-trifluoroethyl trifluoromethanesulfonate (7.2 mL, 49.7 mmol) is added at 70° C. The reaction medium is stirred for 2 hours 30 minutes at 70° C. The reaction medium is concentrated and the residue is taken up in DCM. The solution is washed with water and then with saturated NaCl solution, dried over Na$_2$SO$_4$, filtered and concentrated to dryness to give a brown solid, which is taken up in a diisopropyl ether/acetone mixture (2/1) and stirred for 16 hours to give 12.1 g of a white powder (yield: 57%).

LCMS (Method E): MH$^+$=347.9, RT=5.27 min

Step 1.6. 7-(pyrid-2-yl)-1-(tetrahydro-2H-pyran-2-yl)-5-(2,2,2-trifluoroethyl)-2,5-dihydro-4H-pyrazolo[4,3-c]quinolin-4-one and 7-(pyrid-2-yl)-2-(tetrahydro-2H-pyran-2-yl)-5-(2,2,2-trifluoroethyl)-2,5-dihydro-4H-pyrazolo[4,3-c]quinolin-4-one To a suspension of 7-bromo-1-(tetrahydro-2H-pyran-2-yl)-5-(2,2,2-trifluoroethyl)-1,5-dihydro-4H-pyrazolo[4,3-c]quinolin-4-one and 7-bromo-2-(tetrahydro-2H-pyran-2-yl)-5-(2,2,2-trifluoroethyl)-1,5-dihydro-4H-pyrazolo[4,3-c]quinolin-4-one (1.0 g, 2.32 mmol) in 20 mL of anhydrous DMF contained in a microwave reactor under nitrogen are added 2-pyridyltri-n-butylstannane (1.21 mL, 3.02 mmol) and the catalyst Pd(t-Bu$_3$P)$_2$ (356 mg, 0.7 mmol). The reactor is sealed and the reaction medium is stirred for 10 minutes at 120° C. under microwave irradiation. The mixture is concentrated to dryness and taken up in EtOAc. The solution is washed with saturated NaHCO$_3$ solution, saturated aqueous NaCl solution, dried over Na$_2$SO$_4$, filtered and concentrated to dryness to give a beige-coloured solid. After purification by flash chromatography on silica (DCM/EtOH: 95/5 to 85/15), 0.38 g of a white powder is obtained (yield: 38%).

LCMS (Method A): MH$^+$=429,2, RT=8.14 min

Step 1.7. 7-(pyrid-2-yl)-5-(2,2,2-trifluoroethyl)-1,5-dihydro-4H-pyrazolo[4,3-c]quinolin-4-one hydrochloride To a solution of 7-(pyrid-2-yl)-1-(tetrahydro-2H-pyran-2-yl)-5-(2,2,2-trifluoroethyl)-2,5-dihydro-4H-pyrazolo[4,3-c]quinolin-4-one and 7-(pyrid-2-yl)-2-(tetrahydro-2H-pyran-2-yl)-5-(2,2,2-trifluoroethyl)-2,5-dihydro-4H-pyrazolo[4,3-c]quinolin-4-one (60 mg, 0.14 mmol) in 1 mL of DCM is added a 4M solution of anhydrous hydrogen chloride in dioxane (350 µL, 1.40 mmol). After stirring for 1 hour at room temperature, the suspension is filtered and the solid is dried under vacuum to give 59 mg of 7-(pyrid-2-yl)-5-(2,2,2-trifluoroethyl)-1,5-dihydro-4H-pyrazolo[4,3-c]quinolin-4-one in the form of a beige-coloured powder (hydrochloride, 0.88 H$_2$O; quantitative yield).

LCMS (Method A): MH$^+$=345.0, RT=6.63 min
$^1$H NMR (400 MHz, DMSO-d$_6$): δ ppm 8.79 (dd, 1 H) 8.47 (br. s., 1 H) 8.39 (s, 1 H) 8.35 (d, 1 H) 8.26 (d, 1 H) 8.14 (dd, 1 H) 8.10 (t, 1 H) 7.51-7.58 (m, 1 H) 5.47 (d, 1 H) 5.42 (d, 1 H)

EXAMPLE 2

7-(2-aminopyrid-3-yl)-5-(2,2,2-trifluoroethyl)-1,5-dihydro-4H-pyrazolo[4,3-c]quinolin-4-one hydrochloride (Compound 2)

Step 2.1. 7-(3-aminopyrid-4-yl)-1-(tetrahydro-2H-pyran-2-yl)-5-(2,2,2-trifluoroethyl)-1 5-dihydro-4H-pyrazolo[4,3-c]quinolin-4-one 7-Bromo-1-(tetrahydro-2H-pyran-2-yl)-5-(2,2,2-trifluoroethyl)-1,5-dihydro-4H-pyrazolo[4,3-c]quinolin-4-one and 7-bromo-2-(tetrahydro-2H-pyran-2-yl)-5-(2,2,2-trifluoroethyl)-1,5-dihydro-4H-pyrazolo[4,3-c]quinolin-4-one (9.7 g, 19.4 mmol), potassium carbonate (5.3 g, 38.4 mmol), 3-(4,4,5,5-tetramethyl-1,3,2-dioxaborolan-2-yl)pyrid-2-amine (4.82 g, 21.9 mmol), 14 mL of anhydrous DMF, 1.8 mL of degassed water, and the catalyst PdCl$_2$(dppf) (0.79 g, 0.96 mmol) are successively introduced into a microwave reactor under argon. The reactor is sealed and the mixture is stirred for 10 minutes at 130° C. under microwave irradiation. The mixture is diluted with EtOAc, poured into saturated aqueous NaHCO₃ solution and stirred for 30 minutes. The precipitate is filtered off and washed with water and then taken up in isopropanol. After filtering off and drying, 7.58 g of a grey powder are obtained (yield: 88%).

LCMS (Method D): MH$^+$=444.2, RT=0.87 min

Step 2,2. 7-(2-aminopyrid-3-yl)-5-(2,2,2-trifluoroethyl)-1,5-dihydro-4H-pyrazolo[4,3-c]quinolin-4-one hydrochloride The product is obtained according to the procedure described in Step 1.7. by treating 7-(3-aminopyrid-4-yl)-1-(tetrahydro-2H-pyran-2-yl)-5-(2,2,2-trifluoroethyl)-1,5-dihydro-4H-pyrazolo[4,3-c]quinolin-4-one with anhydrous HCl in dioxane (4 M), in the form of a beige-coloured powder (hydrochloride, 2 H₂O; yield 89%).

LCMS (Method A): MH$^+$=360.1, RT=4.83 min $^1$H NMR (400 MHz, DMSO-d₆): δ ppm 14.22 (br. s., 1 H) 8.20-8.60 (m, 2 H) 8.11 (dd, 1 H) 7.95 (dd, 1 H) 7.87 (s, 1 H) 7.80 (br. s., 2 H) 7.50 (d, 1 H) 7.06 (dd, 1 H) 5.35 (d, 1 H) 5.31 (d, 1 H)

EXAMPLE 3

7-(pyrid-3-yloxy)-5-(2,2,2-trifluoroethyl)-2,5-dihydro-4H-pyrazolo[4,3-c]quinolin-4-one hydrochloride (Compound 99)

Step 3.1. 7-bromo-1-{[2-(trimethylsilyl)ethoxy]methyl}-1,5-dihydro-4H-pyrazolo[4,3-c]quinolin-4-one and 7-bromo-2-{[2-(trimethylsilyl)ethoxy]methyl}-1,5-dihydro-4H-pyrazolo[4,3-c]quinolin-4-one To a suspension of 7-bromo-1,5-dihydro-4H-pyrazolo[4,3-c]quinolin-4-one [described in Step 1.3.] (1.49 g, 5.64 mmol) in 30 mL of anhydrous DMF is added caesium carbonate (2.0 g, 6.21 mmol) and [2-(chloromethoxy)ethyl](trimethyl)silane (10 mL, 56.4 mmol) dropwise. The reaction mixture is stirred at room temperature for 16 hours under nitrogen and then poured into water and extracted with a THF/EtOAc mixture (50/50). The organic phase is washed with saturated aqueous NaCl solution, dried over Na₂SO₄, filtered and concentrated to dryness. The residue obtained is purified by flash chromatography on silica (DCM/MeOH: 100/0 to 98/2) to give 1.45 g of a yellow solid (yield: 61%).

LCMS (Method A): MH$^+$=396.1, RT=8.77 min

Step 3.2. 7-bromo-5-(2,2,2-trifluoroethyl)-1-{[2-(trimethylsilyl)ethoxy]methyl}-1,5-dihydro-4H-pyrazolo[4,3-c]quinolin-4-one and 7-bromo-5-(2,2,2-trifluoroethyl)-2-{[2-(trimethylsilyl)ethoxy]methyl}-1,5-dihydro-4H-pyrazolo[4,3-c]quinolin-4-one To a suspension of 7-bromo-1-{[2-(trimethylsilyl)ethoxy]methyl}-1,5-dihydro-4H-pyrazolo[4,3-c]quinolin-4-one, 7-bromo-2-{[2-(trimethylsilyl)ethoxy]methyl}-1,5-dihydro-4H-pyrazolo[4,3-c]quinolin-4-one (10.0 g, 25.4 mmol) and caesium carbonate (24.8 g, 76.1 mmol) in 130 mL of MeTHF heated to 60° C. is added 2,2,2-trifluoroethyl trifluoromethanesulfonate (5.5 mL, 38.0 mmol) dropwise. The mixture is stirred at 60° C. for 3 hours. The reaction medium is cooled and concentrated to dryness. The residue obtained is taken up in water, filtered and dried. After purification by flash chromatography (cyclohexene/EtOAc: 90/10 to 50/50), 6.67 g of a white powder are obtained (yield: 55%).

LCMS (Method A): MH$^+$=476.3, RT=10.64 min

Step 3.3. 7-(pyrid-3-yloxy)-5-(2,2,2-trifluoroethyl)-1-{[2-(trimethylsilyl)ethoxy]-methyl}-1,5-dihydro-4H-pyrazolo[4,3-c]quinolin-4-one and 7-(pyrid-3-yloxy)-5-(2,2,2-trifluoroethyl)-2-{[2-(trimethylsilyl)ethoxy]methyl}-1,5-dihydro-4H-pyrazolo[4,3-c]quinolin-4-one 7-Bromo-1-[2-(trimethylsilyl)ethoxy]-1,5-dihydro-4H-pyrazolo[4,3-c]quinolin-4-one and 7-bromo-2-[2-(trimethylsilyl)ethoxy]-1,5-dihydro-4H-pyrazolo[4,3-c]quinolin-4-one (0.2 g, 0.42 mmol), 3-hydroxypyridine (0.12 g, 1.26 mmol), the catalyst CuI (80 mg, 0.42 mmol), the ligand 1,1,1-tris(hydroxymethyl)ethane (50 mg, 0.42 mmol), caesium carbonate (0.55 g, 1.68 mmol), 0.4 mL of anhydrous DMF and 1.5 mL of dioxane are successively introduced into a reactor under argon. The reactor is sealed and the mixture is stirred vigorously for 17 hours at 110° C. After cooling, the mixture is filtered off through { }elite and washed with EtOAc. The solution is washed with water and with saturated aqueous NaCl solution, dried over Na₂SO₄ and concentrated to dryness to give 195 mg of a brown gum, which is used in the next step.

LCMS (Method E): MH$^+$=491.4, RT=2.36 min

Step 3.4. 7-(pyrid-3-yloxy)-5-(2,2,2-trifluoroethyl)-2,5-dihydro-4H-pyrazolo[4,3-c]quinolin-4-one hydrochloride A suspension of 7-(pyrid-3-yloxy)-5-(2,2,2-trifluoroethyl)-1-{[2-(trimethylsilyl)ethoxy]-methyl}-1,5-dihydro-4H-pyrazolo[4,3-c]quinolin-4-one and (2,2,2-trifluoroethyl)-2-{[2-(trimethylsilyl)ethoxy]methyl}-1,5-dihydro-4H-pyrazolo[4,3-c]quinolin-4-one (0.19 g, 0.39 mmol) in 10 mL of anhydrous hydrogen chloride dissolved in dioxane (4M) is stirred at room temperature for 18 hours. The suspension is filtered and the solid is washed with DCM and then purified by flash chromatography on a C18 reverse phase (H₂O/MeCN: 100/0 to 0/100). The gum obtained is dissolved in molar hydrochloric acid solution and then concentrated to dryness to give 78 mg of a white powder (1.2 hydrochloride, 1.15 H₂O; yield: 58%).

LCMS (Method A): MH$^+$=361.2, RT=6.65 min $^1$H NMR (400 MHz, DMSO-d₆): δ ppm 8.66 (d, 1 H) 8.56 (d, 1 H) 8.41 (s, 1 H) 8.30 (d, 1 H) 7.84 (d, 1 H) 7.73 (dd, 1 H) 7.62 (s, 1 H) 7.19 (dd, 1 H) 5.27 (d, 1 H) 5.23 (d, 1 H)

EXAMPLE 4

5-(2,2-difluoroethyl)-7-(pyrid-4-yl)-1,5-dihydro-4H-pyrazolo[4,3-c]quinolin-4-one hydrochloride (Compound 102)

Step 4.1. 7-(pyrid-4-yl)-1-{[2-(trimethylsilyl)ethoxy]methyl}-1,5-dihydro-4H-pyrazolo[4,3-c]quinolin-4-one and 7-(pyrid-4-yl)-2-{[2-(trimethylsilyl)ethoxy]methyl}-1,5-dihydro-4H-pyrazolo[4,3-c]quinolin-4-one To a solution of 7-bromo-1-{[2-(trimethylsilyl)ethoxy]methyl}-1,5-dihydro-4H-pyrazolo[4,3-c]quinolin-4-one and 7-bromo-2-{[2-(trimethylsilyl)ethoxy]methyl}-1,5-dihydro-4H-pyrazolo[4,3-c]quinolin-4-one [described in Step 3.1] (18.2 g, 46.2 mmol) in 150 mL of DMF placed in a microwave reactor are successively added 4-(4,4,5,5-tetramethyl-1,3,2-dioxaborolan-2-yl)pyridine (11.4 g, 55.4 mmol), aqueous 2M K₃PO₄ solution (47 mL, 92.4 mmol) and the catalyst PdCl₂ (dppf) (1.88 g, 2.31 mmol) under nitrogen. The reactor is sealed and the reaction mixture is stirred for 20 minutes at 150° C. under microwave irradiation. After concentrating the reaction mixture, purification by flash chromatography on silica (DCM/MeOH: 0/100 to 95/5) gives 12.4 g of 7-(pyrid-4-yl)-1-[2-(trimethylsilyl)ethoxy]-1,5-dihydro-4H-pyrazolo[4,3-c]quinolin-4-one and 7-(pyrid-4-yl)-2-[2-(trimethylsilyl)ethoxy]-1,5-dihydro-4H-pyrazolo[4,3-c]quinolin-4-one in the form of a white solid (yield: 54%).

LCMS (Method A) MH$^+$=393.2, RT=6.60 and 6.74 min (isomers of pyrazole protected with the SEM group)

Step 4.2. 5-(2,2-difluoroethyl)-7-(pyrid-4-yl)-1-{[2-(trimethylsilyl)ethoxy]methyl}-1,5-dihydro-4H-pyrazolo[4,3-c]quinolin-4-one and 5-(2,2-difluoroethyl)-7-(pyrid-4-yl)-2-{[2-(trimethylsilyl)ethoxy]methyl}-1,5-dihydro-4H-pyrazolo[4,3-c]quinolin-4-one To a solution of 7-(pyrid-4-yl)-1-{[2-(trimethylsilyl)ethoxy]methyl}-1,5-dihydro-4H-pyrazolo[4,3-c]quinolin-4-one and 7-(pyrid-4-yl)-2-{[2-(trimethylsilyl)ethoxy]methyl}-1,5-dihydro-4H-pyrazolo[4,3-c]quinolin-4-one (0.40 g, 1.0 mmol) in 8 mL of DMF is added caesium carbonate (0.66 g, 2.04 mmol) and 2,2-difluoroethyl trifluoromethanesulfonate (0.33 mL, 2.55 mmol). The mixture is stirred for 24 hours at room temperature, and then poured into water and extracted with EtOAc. The organic phase is washed with saturated aqueous NaCl solution, dried over Na$_2$SO$_4$, filtered and concentrated to dryness. After purification on silica by flash chromatography (DCM/EtOH: 100/0 to 95/5), 108 mg of an orange-coloured solid are obtained (yield: 23%).

LCMS (Method A) MH$^+$=457.3, RT=6.94 min

Step 4.3. 5-(2,2-difluoroethyl)-7-(pyrid-4-yl)-1,5-dihydro-4H-pyrazolo[4,3-c]quinolin-4-one hydrochloride To a solution of 5-(2,2-difluoroethyl)-7-(pyrid-4-yl)-1-{[2-(trimethylsilyl)ethoxy]methyl}-1,5-dihydro-4H-pyrazolo[4,3-c]quinolin-4-one and 5-(2,2-difluoroethyl)-7-(pyrid-4-yl)-2-{[2-(trimethylsilyl)ethoxy]methyl}-1,5-dihydro-4H-pyrazolo[4,3-c]quinolin-4-one (100 mg, 0.22 mmol) in 2 mL of DCM is added a 4M solution of anhydrous hydrogen chloride in dioxane (1.10 mL, 4.38 mmol) at room temperature. After stirring at room temperature for 24 hours, the mixture is filtered. The solid obtained is taken up in isopropanol, filtered off and dried under vacuum to give 74 mg of a white powder (hydrochloride, yield: 94%).

LCMS (Method A): MH$^+$=327.0, RT=4.86
$^1$H NMR (400 MHz, DMSO-d$_6$): δ ppm 8.96-9.03 (m, 2 H) 8.37-8.56 (m, 4 H) 8.19 (s, 1 H) 7.98 (d, 1 H) 6.43 (tt, 1 H) 5.04 (td, 2 H)

EXAMPLE 5

5-(propan-2-yl)-7-(pyrid-4-yl)-1,5-dihydro-4H-pyrazolo[4,3-c]quinolin-4-one hydrochloride (Compound 107)

Step 5.1. 4-bromo-2=(propan-2-ylamino)benzoic acid

Isopropylamine (134.9 g, 2,28 mol), 10 mL of t-butanol and 4-bromo-2-fluorobenzoic acid (10 g, 45.7 mmol), added portionwise, are mixed together in a microwave reactor. The reactor is sealed and the mixture is stirred for 45 minutes at 150° C. under microwave irradiation. The colourless solution is cooled and poured into ice-water, and glacial acetic acid is then added. The white precipitate formed is filtered off, washed with water and dried under vacuum. 7.9 g of a white solid are obtained (yield: 67%), LCMS (Method A) MH$^+$=257.1, RT=8.11 min Step 5.2. 4-bromo-2-[(3-ethoxy-3-oxopropanoyl)(propan-2-yl)amino]benzoic acid To a solution of 4-bromo-2-(propan-2-ylamino)benzoic acid (6.8 g, 26.64 mmol) in 260 mL of DCM is added triethylamine (4 mL, 31.6 mmol), followed by dropwise addition of ethyl malonate chloride (4.0 mL, 31. mmol). The mixture is stirred for 2 hours at room temperature, and then poured into molar hydrochloric acid solution and extracted with EtOAc. The organic phase is washed with water and with saturated aqueous NaCl solution, dried over Na$_2$SO$_4$ and concentrated to dryness. 7.15 g of a pale yellow solid are obtained (yield: 72%).

LCMS (Method A): MH$^+$=372.1, RT=7,42 min

Step 5.3. ethyl 7-bromo-2,4-dioxo-1-(propan-2-yl)-1,2,3,4-tetrahydroquinoline-3-carboxylate To a solution of 4-bromo-2-[(3-ethoxy-3-oxopropanoyl)(propan-2-yl)amino]benzoic acid (6.2 g, 16.7 mmol) in 170 mL of DCE is added triethylamine (3.5 mL, 25.1 mmol), followed by addition of thionyl chloride (1.45 mL, 20.6 mmol) at 0° C. After stirring at room temperature for 3 hours, the reaction medium is diluted with DCM and washed with aqueous HCl solution (1M). The organic phase is washed with saturated aqueous NaHCO$_3$ solution and saturated aqueous NaCl solution, dried over Na$_2$SO$_4$ and concentrated to dryness. The oil obtained is purified by flash chromatography (toluene/EtOAc: 100/0 to 90/10) to give 2,23 g of a white solid (yield: 52%).

LCMS (Method A) MH$^+$=354,2, RT=9.58 min

Step 5.4. 7-bromo-4-hydroxy-1-(propan-2-yl)quinolin-2(1H)-one

A suspension of ethyl 7-bromo-2,4-dioxo-1-(propan-2-yl)-1,2,3,4-tetrahydroquinoline-3-carboxylate (1.5 g, 4.23 mmol) in sodium hydroxide (2M solution, 32 mL, 64 mmol) is heated to reflux. The reaction medium becomes homogeneous and, after 3 hours, a suspension is once again observed. 6 mL of NMP are added to homogenize, and the resulting mixture is than refluxed for 12 hours. The solution cooled to room temperature is poured into 6M hydrochloric acid solution to give a white precipitate, which is filtered off. After rinsing with water and drying the precipitate under vacuum, 1.1 g of a white solid are obtained (yield: 91%).

LCMS (Method A) MH$^+$=284.1 RT=6.99 min

Step 5.5. (3E,Z)-7-bromo-3-[(dimethylamino)methylidene]-1-(propan-2-yl)quinoline-2,4(1H,3H)-dione As described in Step 1.1., to a solution of 7-bromo-4-hydroxy-1-(propan-2-yl)quinolin-2(1H)-one (1.2 g, 4.25 mmol) in 43 mL of toluene is added N,N-dimethylformamide dimethyl acetal (8.8 mL, 63.8 mmol). The solution is heated at 80° C. for 8 hours. The resulting mixture is concentrated to dryness to give a pale yellow solid, which is taken up in diisopropyl ether. After filtering off, 321 mg of a white solid are obtained (yield: 92%), LCMS (Method A) MH$^+$=338.1, RT=8.39 min

Step 5.6. 7-bromo-4-chloro-2-oxo-1-(propan-2-yl)-1,2-dihydroquinoline-3-carbaldehyde As described in Step 1.2., to a solution of (3E,Z)-7-bromo-3-[(dimethylamino)methyl-idene]-1-(propan-2-yl)quinoline-2,4(1H,3H)-dione (1.32 g, 3.9 mmol) in 10 mL of DMF is added dropwise $POCl_3$ (0.44 mL, 4.70 mmol) at 0° C. The solution is stirred for 3 hours at room temperature and then poured into ice-water to give a precipitate. After filtering off and drying the precipitate under vacuum, 1.2 g of a yellow solid are obtained (yield: 93%).

LCMS (Method A) $MH^+$=327.1, RT=7.29 min

Step 5.7. 7-bromo-5-(propan-2-yl)-1,5-dihydro-4H-pyrazolo[4,3-c]quinolin-4-one As described in Step 1.3., to a solution of 7-bromo-4-chloro-2-oxo-1-(propan-2-yl)-1,2-dihydroquinoline-3-carbaldehyde (1.0 g, 3.08 mmol) in 30 mL of DMF at 0° C. is added hydrazine hydrate (0.19 mL, 3.70 mmol). After stirring for 8 hours at room temperature, the reaction mixture is poured into water. The orange-coloured precipitate formed is filtered off and washed with water and then dried under vacuum to give 859 mg of an orange-coloured solid (yield: 73%).

LCMS (Method A) $MH^+$=306.1, RT=6.88 min

Step 5.8. 5-(propan-2-yl)-7-(pyrid-4-yl)-1,5-dihydro-4H-pyrazolo[4,3-c]quinolin-4-one To a solution of 7-bromo-5-(propan-2-yl)-1,5-dihydro-4H-pyrazolo[4,3-c]quinolin-4-one (0.25 g, 0.82 mmol) in 8 mL of DMF placed in a microwave reactor are added caesium carbonate (0.8 g 2.5 mmol), 4-(4,4,5,5-tetramethyl-1,3,2-dioxaborolan-2-yl)pyridine (0.25 g 1.22 mmol) and the catalyst $PdCl_2(dppf)$ (60 mg, 0.08 mmol). The reactor is sealed and the mixture is stirred for 20 minutes at 150° C. under microwave irradiation. The reaction medium is diluted with an EtOAc/THF mixture (50/50) and washed with water and then with saturated aqueous NaCl solution. The organic phase is dried over $Na_2SO_4$ and concentrated to dryness. After purification by flash chromatography (DCM/MeOH: 100/0 to 90/10), 45 mg of a white solid are obtained (yield: 19%).

LCMS (Method A): $MH^+$=305.2, RT=4.98 min $^1H$ NMR (400 MHz, DMSO-$d_6$): δ ppm 8.92 (d, 2 H) 8.23-8.44 (m, 4 H) 8.11 (s, 1 H) 7.90 (d, 1 H) 5.48 (br. s., 1 H) 1.64 (d, 6 H)

EXAMPLE 6

8-fluoro-7-(pyrid-2-yl)-5-(2,2,2-trifluoroethyl)-1,5-dihydro-4H-pyrazolo[4,3-c]quinolin-4-one hydrochloride (Compound 109)

Step 6.1, 1-(tetrahydro-2H-pyran-2-yl)-1H-pyrazole-4-carboxylic acid

To a suspension of 1H-pyrazole-4-carboxylic acid (50 g, 446 mmol) in 500 mL of DMF are added para-toluenesulfonic acid (8.48 g, 44 mmol) and DHP (132 mL, 1561 mmol). The reaction medium turns yellow and then black after stirring at room temperature for 20 hours. The reaction mixture is poured into saturated aqueous $NaHCO_3$ solution and extracted with EtOAc. The aqueous phase is acidified to pH 3 by adding 6M hydrochloric acid solution. The precipitate formed is filtered off and washed with water and then dried under vacuum at 50° C. to give 61.2 g of a white powder (yield: 70%).

LCMS (Method D): $MH^+$=197.1, RT=0.60 min

Step 6.2. 1-(tetrahydro-2H-pyran-2-yl)-1H-pyrazole-4-carboxylic acid fluoride To a solution of 1-(tetrahydro-2H-pyran-2-yl)-1H-pyrazole-4-carboxylic acid (31.7 g, 61 mmol) in 650 mL of DCM at 0° C. are added pyridine (77 mL, 0.97 mol) and cyanogen fluoride (41 mL, 0.48 mmol) dropwise. The reaction medium is stirred for 4 hours at room temperature, poured into saturated aqueous $NaHCO_3$ solution and extracted with DCM. The organic phase is washed with water and then with saturated aqueous NaCl solution, dried over $Na_2SO_4$, filtered and concentrated to dryness to give 29.1 g of a brown oil (yield: 91%).

LCMS (Method D): $[M+NR_4]^+$=216.6, RT=0.95 min

Step 6.3. N-(5-chloro-4-fluoro-2-iodophenyl)-1-(tetrahydro-2H-pyran-2-yl)-1H-pyrazole-4-carboxamide Potassium t-butoxide (12.52 g, 111.6 mmol) is added at room temperature to a solution of 5-chloro-4-fluoro-2-iodoaniline (5.0 g, 22.3 mmol) in 250 mL of anhydrous THF under nitrogen. After stirring for 15 minutes, a solution of 1-(tetrahydro-2H-pyran-2-yl)-1H-pyrazole-4-carboxylic acid fluoride (5.67 g, 24.6 mmol) in 30 mL of anhydrous THF is added dropwise. The reaction mixture is stirred for 4 hours at room temperature and then poured into saturated aqueous $NaHCO_3$ solution and extracted with EtOAc. The organic phase is washed with saturated aqueous NaCl solution, dried over $Na_2SO_4$ and concentrated to dryness. After purification by flash chromatography on silica (cyclohexene/EtOAc: 95/5 to 80/20), a red solid is obtained, which is purified by flash chromatography on amine phase (DCM) to give 2.84 g of a white solid (yield: 31%).

LCMS (Method E): $MH^+$=404.0, RT=2,29 min

Step 6.4. N-(5-chloro-4-fluoro-2-iodophenyl)-1-(tetrahydro-2H-pyran-2-yl)-N-(2,2,2-trifluoroethyl)-1H-pyrazole-4-carboxamide To a solution of N-(5-chloro-4-fluoro-2-iodophenyl)-1-(tetrahydro-2H-pyran-2-yl)-1H-pyrazole-4-carboxamide (1.26 g, 3.13 mmol) in 55 mL of anhydrous MeTHF heated to 65° C. are added potassium t-butoxide (421 mg, 3.76 mmol) and 2,2,2-trifluoroethyl trifluoromethanesulfonate (0.54 mL, 3.76 mmol). The reaction mixture is stirred for 2 hours at 65° C., and then cooled, poured into saturated aqueous $NaHCO_3$ solution and extracted with EtOAc. The organic phase is washed with saturated aqueous NaCl solution, dried over $Na_2SO_4$ and concentrated to dryness. After purification by flash chromatography on silica (DCM/EtOAc: 100/0 to 95/5), 2.32 g of an orange-coloured solid are obtained (yield: 73%).

LCMS (Method G): $MH^+$=404.0, RT=1.82 min

Step 6.5. 7-chloro-8-fluoro-2-(tetrahydro-2H-pyran-2-yl)-5-(2,2,2-trifluoroethyl)-1,5-dihydro-4H-pyrazolo[4,3-c]quinolin-4-one The catalyst $Pd(PPh_3)_4$ (630 mg, 0.55 mmol) and potassium acetate (890 mg, 9.0 mmol) are added to a solution of N-(5-chloro-4-fluoro-2-iodophenyl)-1-(tetrahydro-2H-pyran-2-yl)-N-(2,2,2-trifluoroethyl)-1H-pyrazole-4-carboxamide (2,2 g, 4.5 mmol) in 10 mL of anhydrous DMF placed in a microwave reactor under nitrogen. The reactor is sealed and the reaction mixture is stirred for 15 minutes at 90° C. under microwave irradiation. A further amount of catalyst Pd(PPh$_3$)$_4$ (630 mg, 0.55 mmol) and of potassium acetate (890 mg, 9.0 mmol) are added to the reaction medium, which is stirred for 15 minutes at 110° C. under microwave irradiation. The mixture is cooled, poured into water and extracted with EtOAc. The organic phase is washed with saturated aqueous NaCl solution, dried over Na$_2$SO$_4$ and concentrated to dryness. After purification by flash chromatography on silica (DCM/EtOAc: 100/0 to 95/5) and then (cyclohexene/EA: 90/10) and DCM (100%), 260 mg of a white solid are obtained (yield: 57%).

LCMS (Method G): MH$^+$=403.9, RT=2.59 min

Step 6.6. 8-fluoro-7-(pyrid-2-yl)-2-(tetrahydro-2H-pyran-2-yl)-5-(2,2,2-trifluoroethyl)-1,5-dihydro-4H-pyrazolo[4,3-d]quinolin-4-one According to the process described in Step 1.6., 2-pyridyl-tri-n-butylstannane (4.40 mL, 11.5 mmol) and the catalyst Pd(tBu$_3$P)$_2$ (199 mg, 0.39 mmol) are added to a solution of 7-chloro-8-fluoro-2-(tetrahydro-2H-pyran-2-yl)-5-(2,2,2-trifluoroethyl)-1,5-dihydro-4H-pyrazolo[4,3-c]quinolin-4-one (526 mg, 1.30 mmol) in 10 mL of anhydrous DMF under nitrogen placed in a microwave reactor. The reactor is sealed and the reaction mixture is stirred for 20 minutes at 130° C. under microwave irradiation. The mixture is poured into saturated aqueous NaHCO$_3$ solution and extracted with EtOAc. The organic phase is washed with water, with saturated aqueous NaCl solution, dried over Na$_2$SO$_4$ and concentrated to dryness. After purification by flash chromatography on silica (cyclohexene/EtOAc: 90/10 to 70/30 and then DCM/acetone: 98/2 to 90/10), 72 mg of a white powder are obtained (yield: 12%).

LCMS (Method E): MH$^+$=447.0, RT=2.44 min

Step 6.7. 8-fluoro-7-(pyrid-2-yl)-5-(2,2,2-trifluoroethyl)-1,5-dihydro-4H-pyrazolo[4,3-c]quinolin-4-one hydrochloride The product is obtained according to the procedure described in Step 1.7. by treating 8-fluoro-7-(pyrid-2-yl)-2-(tetrahydro-2H-pyran-2-yl)-5-(2,2,2-trifluoroethyl)-1,5-dihydro-4H-pyrazolo[4,3-c]quinolin-4-one with HCl in dioxane (4M). It is in the form of a white powder (hydrochloride; yield 75%).

LCMS (Method D): MH$^+$=363.1, RT=1.69 min
$^1$H NMR (500 MHz, DMSO-d$_6$): δ ppm 8.81-8.83 (m, 1 H) 8.52 (br. s. 1 H) 8.21 (d, 1 H) 8.13 (d, 1 H) 8.03 (td, 1 H) 7.90 7.93 (m, 1 H) 7,52 (ddd, 1 H) 5.35 (d, 1 H) 5.32 (d, 1 H)

EXAMPLE 7

7-(2-chloropyrid-3-yl)-5-(2,2,2-trifluoroethyl)-1,5-dihydro-4H-pyrazolo[4,3-c]quinolin-4-one (Compound 111)

Step 7.1. 1-(tetrahydro-2H-pyran-2-yl-7-(4,4,5,5-tetramethyl-1,3,2-dioxaborolan-2-yl)-5-(2,2,2-trifluoroethyl)-1,5-dihydro-4H-pyrazolo[4,3-c]quinolin-4-one and 2-(tetrahydro-2H-pyran-2-yl)-7-(4,4,5,5-tetramethyl-1,3,2-dioxaborolan-2-yl)-5-(2,2,2-trifluoroethyl)-1,5-dihydro-4H-pyrazolo[4,3-c]quinolin-4-one To a suspension of 7-bromo-1-(tetrahydro-2H-pyran-2-yl)-5-(2,2,2-trifluoroethyl)-1,5-dihydro-4H-pyrazolo[4,3-c]quinolin-4-one and 7-bromo-2-(tetrahydro-2H-pyran-2-yl)-5-(2,2,2-trifluoroethyl)-1,5-dihydro-4H-pyrazolo[4,3-c]quinolin-4-one [described in Step 1.5.] (8.0 g, 18.6 mmol) in 200 mL of DMF is added pinacol diborane (18.9 g, 74.4 mmol). The mixture is heated to 60° C. under nitrogen, followed by addition of potassium acetate (4.6 g, 46.5 mmol) and the catalyst PdCl$_2$(dppf) (3.04 g, 3.72 mmol). The solution is heated for 3 hours at 60° C., and then cooled to room temperature and poured into saturated aqueous NaHCO$_3$ solution. After extraction with EtOAc, the organic phase is washed with saturated aqueous NaCl solution, dried over Na$_2$SO$_4$ and concentrated to dryness. A black oil is obtained, to which is added diisopropyl ether, leading to the formation of a black solid. After filtering and concentrating the filtrate, a yellow oil is obtained, which is taken up in a petroleum ether (40-65° C.)/diisopropyl ether mixture, leading to precipitation of a pale yellow solid. After filtering off and drying the precipitate under vacuum, 5.10 g of a pale yellow solid are obtained (first crop).

The filtrate is concentrated. Saturated aqueous NaHCO$_3$ solution and 10% THF are added to the yellow oil obtained. The mixture is stirred vigorously at room temperature for 12 hours and then acidified with molar hydrochloric acid solution, and extracted with EtOAc. The organic phase is washed with saturated aqueous NaCl solution, dried over Na$_2$SO$_4$ and concentrated to dryness to give a yellow solid, which is taken up in petroleum ether. After filtering off and drying under vacuum, 1.44 g of a white solid are obtained (second crop).

The two crops are combined and taken up in diisopropyl ether. After filtering off and drying, 6.54 g of a white powder are obtained (yield: 74%).

LCMS (Method F): MH$^+$=478.0, RT=2.80 min

Step 7.2. 7-(2-chloropyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-chloropyrid-3-yl)-2-(tetrahydro-2H-pyran-2-yl)-5-(2,2,2-trifluoroethyl)-1,5-dihydro-4H-pyrazolo[4,3-c]quinolin-4-one To a solution of 1-(tetrahydro-2H-pyran-2-yl)-7-(4,4,5,5-tetramethyl-1,3,2-dioxaborolan-2-yl)-5-(2,2,2-trifluoroethyl)-1,5-dihydro-4H-pyrazolo[4,3-c]quinolin-4-one and 2-(tetrahydro-2H-pyran-2-yl)-7-(4,4,5,5-tetramethyl-1,3,2-dioxaborolan-2-yl)-5-(2,2,2-trifluoroethyl)-1,5-dihydro-4H-pyrazolo[4,3-c]quinolin-4-one (100 mg, 0.1 mmol) in 3 mL of DMF under nitrogen at 95° C. are added the catalyst PdCl$_2$(dppf) (17 mg, 0.02 mmol), caesium carbonate (136 mg, 0.42 mmol), 0.5 mL of degassed water and 3-bromo-2-chloropyridine (40 mg, 0.21 mmol). The reaction mixture is stirred for 1.5 hours 95° C. under nitrogen, cooled to room temperature, concentrated and taken up in EtOAc. The solution is washed with water and than with saturated aqueous NaCl solution, dried over Na$_2$SO$_4$, filtered and concentrated to dryness to give a black wax. After purification by flash chromatography on silica (DCM/EtOH: 100/0 to 95/5), 38 mg of a yellow solid are obtained (yield=79%).

LCMS (Method G): MH$^+$=463.3, RT=1.66 min

Step 7.3. 7-(2-chloropyrid-3-yl)-5-(2,2,2-trifluoroethyl)-1,5-dihydro-4H-pyrazolo[4,3-c]quinolin-4-one To a solution of 7-(2-chloropyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-chloropyrid-3-yl)-2-(tetrahydro-2H-pyran-2-yl)-5-(2,2,2-trifluoroethyl)-1,5-dihydro-4H-pyrazolo[4,3-c]quinolin-4-one (1.6 g, 3.46 mmol) in 34 mL of DCM, is added a 4M solution of hydrogen chloride in dioxane (8.5 mL, 34.6 mmol). The mixture is stirred for 3 hours at room temperature and concentrated to dryness. After purification by flash chromatography on amine phase (DCM/EtOH: 100/0 to 90/10), 189 mg of a white solid are obtained (yield=15%).

LCMS (Method A): MH$^+$=379.2, RT=6.91 min $^1$H NMR (400 MHz, DMSO-d$_6$): δ ppm 8.51 (dd, 1 H) 8.47 (br. s., 1 H) 8.29 (d, 1 H) 7.95(dd, 1 H)7.90(s, 1 H)7.61(dd, 1 H)7.53(d, 1 H)5.36(d, 1 H)5.31(dd, 1 H)

EXAMPLE 8

8-chloro-7-(pyrid-2-yl)-5-(2,2,2-trifluoroethyl)-1,5-dihydro-4H-pyrazolo[4,3-c]quinolin-4-one hydrochloride (Compound 194)

Step 8.1. 8-chloro-7-(pyrid-2-yl)-5-(2,2,2-trifluoroethyl)-1,5-dihydro-4H-pyrazolo[4,3-c]quinolin-4-one To a suspension of 7-(pyrid-2-yl)-1-(tetrahydro-2H-pyran-2-yl)-5-(2,2,2-trifluoroethyl)-2,5-dihydro-4H-pyrazolo[4,3-c]quinolin-4-one and 7-(pyrid-2-yl)-2-(tetrahydro-2H-pyran-2-yl)-5-(2,2,2-trifluoroethyl)-2,5-dihydro-4H-pyrazolo[4,3-c]quinolin-4-one [described in Step 1.5] (1.6 g, 3.73 mmol) in 32 mL of acetic acid is added N-chlorosuccinimide (2.49 g, 18.67 mmol). The reaction mixture is stirred for 3 hours at 80° C., cooled to room temperature and concentrated to dryness to give a yellow solid, which is dissolved in DCM. The solution is washed with saturated aqueous NaHCO$_3$ solution and then with saturated aqueous NaCl solution, dried over Na$_2$SO$_4$, filtered and concentrated to give a yellow solid. The solid is taken up in DCM. After filtering off and drying, 542 mg of a white solid are obtained (yield: 35%).

LCMS (Method A): MH$^+$=379.2, RT=6.93 min

Step 8.2. 8-chloro-7-(pyrid-2-yl)-5-(2,2,2-trifluoroethyl)-1,5-dihydro-4H-pyrazolo[4,3-c]quinolin-4-one hydrochloride To a solution of 8-chloro-7-(pyrid-2-yl)-5-(2,2,2-trifluoroethyl)-1,5-dihydro-4H-pyrazolo[4,3-c]quinolin-4-one (532 mg, 1.40 mmol) in a DCM/MeOH mixture (50/50) is added a 4M solution of hydrogen chloride in dioxane (3.5 mL, 14.1 mmol). The suspension is stirred at room temperature and then filtered and dried under vacuum to give 420 mg of a white powder (hydrochloride, 0.06 H$_2$O; yield: 72%)

LCMS (Method A): MH$^+$=379.2, RT=6.91 min $^1$H NMR (400 MHz, DMSO-d$_6$): δ ppm 8.77-8.83 (m, 1 H) 8.52 (br. s., 1 H) 8.40 (s, 1 H) 8.06 (td, 1 H) 7.96 (s, 1 H) 7.77 (d, 1 H) 7.54-7.59 (m, 1 H) 5.35 (d, 1 H) 5.30 (d, 1 H)

EXAMPLE 9

8-bromo-7-(pyrid-2-yl)-5-(2,2,2-trifluoroethyl)-1,5-dihydro-4H-pyrazolo[4,3-c]quinolin-4-one hydrochloride (Compound 195)

Step 9.1. 8-bromo-7-(pyrid-2-yl)-1-(tetrahydro-2H-pyran-2-yl)-5-(2,2,2-trifluoroethyl)-1,5-dihydro-4H-pyrazolo[4,3-c]quinolin-4-one and 8-bromo-7-(pyrid-2-yl)-2-(tetrahydro-2H-pyran-2-yl)-5-(2,2,2-trifluoroethyl)-1,5-dihydro-4H-pyrazolo[4,3-c]quinolin-4-one To a solution of 7-(pyrid-2-yl)-1-(tetrahydro-2H-pyran-2-yl)-5-(2,2,2-trifluoroethyl)-2,5-dihydro-4H-pyrazolo[4,3-c]quinolin-4-one and 7-(pyrid-2-yl)-2-(tetrahydro-2H-pyran-2-yl)-5-(2,2,2-trifluoroethyl)-2,5-dihydro-4H-pyrazolo[4,3-c]quinolin-4-one [described in Step 1.5] (100 mg, 0.23 mmol) in 2 mL of acetonitrile placed in a microwave reactor under nitrogen are added N-bromosuccinimide (50 mg, 0.28 mmol) and the catalyst Pd(OAc)$_2$ (2.6 mg, 0.01 mmol). The reactor is sealed and the reaction mixture is stirred for 15 minutes at 100° C. under microwave irradiation under nitrogen. Since the reaction is incomplete, further N-bromosuccinimide (17 mg, 0.1 mmol) and catalyst Pd(OAc)$_2$ (2.6 mg, 0.01 mmol) are added to the reaction mixture, which is stirred for a further 10 minutes at 100° C. under microwave irradiation. The mixture is diluted in EtOAc, and the solution is washed with water and than with saturated aqueous NaCl solution, dried over Na$_2$SO$_4$, filtered and concentrated to dryness. After purification by flash chromatography on silica (DCM/EtOAc: 90/10 to 80/20), 72 mg of a yellow solid are obtained (yield: 43%).

LCMS (Method A): MH$^+$=507.0, RT=8.88 min

Step 9.2. 8-bromo-7-(pyrid-2-yl)-5-(2,2,2-trifluoroethyl)-1,5-dihydro-4H-pyrazolo[4,3-c]quinolin-4-one hydrochloride The product is obtained according to the procedure described in Step 1.7. by treating 8-bromo-7-(pyrid-2-yl-1-(tetrahydro-2H-pyran-2-yl)-5-(2,2,2-trifluoroethyl)-1,5-dihydro-4H-pyrazolo[4,3-c]quinolin-4-one and 8-bromo-7-(pyrid-2-yl)-2-(tetrahydro-2H-pyran-2-yl)-5-(2,2,2-trifluoroethyl)-1,5-dihydro-4H-pyrazolo[4,3-c]quinolin-4-one with 4M HCl in dioxane, in the form of a white powder (hydrochloride, 0.4 H$_2$O; yield 94%).

LCMS (Method A): MH$^+$=425.2, RT=7.00 min $^1$H NMR (400 MHz, DMSO-d$_6$): δ ppm 8.77-8.84 (m, 1 H) 8.58 (s, 1 H) 8.51 (br. s., 1 H) 8.04-8.17 (m, 1 H) 7.93 (s, 1 H) 7.75 (dd, 1 H) 7.56-7.65 (m, 1 H) 5.33 (d, 1 H) 5.29 (d, 1 H)

EXAMPLE 10

4-oxo-7-(pyrid-4-yl)-5-(2,2,2-trifluoroethyl)-4,5-dihydro-2H-pyrazolo[4,3-c]quinoline-8-carbonitrile hydrochloride (Compound 201)

Step 10.1. 4-oxo-7-(pyrid-4-yl)-5-(2,2,2-trifluoroethyl)-1-{[2-(trimethylsilyl)ethoxy]-methyl}-4,5-dihydro-2H-pyrazolo[4,3-c]quinoline-8-carbonitrile and 4-oxo-7-(pyrid-4-yl)-5-(2,2,2-trifluoroethyl)-2-{[2-(trimethylsilyl)ethoxy]methyl}4,5-dihydro-2H-pyrazolo[4,3-c]quinoline-8-carbonitrile 8-Bromo-7-(pyrid-4-yl)-5-(2,2,2-trifluoroethyl)-2-{[2-(trimethylsilyl)ethoxy]methyl}-2,5-dihydro-4H-pyrazolo[4,3-c]quinolin-4-one [obtained according to the protocols described in Step 4.2. with 2,2,2-trifluoroethyl trifluoromethanesulfonate and Step 9.1.] (1.0 g, 1.88 mmol), zinc cyanide (0.66 g, 5.64 mmol), the catalyst Pd(PPh$_3$)$_4$ (390 mg, 0.34 mmol) and 16 mL of anhydrous DMF are successively introduced into a microwave reactor under nitrogen. The reactor is sealed and the mixture is stirred vigorously for 10 minutes at 180° C. under microwave irradiation. After cooling, the mixture is poured into saturated aqueous NaHCO$_3$ solution. After extraction with EtOAc, the organic phase is washed with saturated aqueous NaCl solution, dried over Na$_2$SO$_4$ and concentrated to dryness. After purification by flash chromatography on silica (diisopropyl ether/EtOAc: 90/10 to 20/80 and then diisopropyl ether/EtOAc: 50/50), 342 mg of a white powder are obtained (yield: 36%).

LCMS (Method A): MH$^+$=500.0, RT=8.59 min

Step 10.2. 4-oxo-7-(pyrid-4-yl)-5-(2,2,2-trifluoroethyl)-4,5-dihydro-2H-pyrazolo[4,3-c]quinoline-8-carbonitrile hydrochloride The product is obtained according to the procedure described in Step 4.3. starting with 4-oxo-7-(pyrid-4-yl)-5-(2,2,2-trifluoroethyl)-1-{[2-(trimethylsilyl)ethoxy]methyl}-4,5-dihydro-2H-pyrazolo[4,3-c]quinoline-8-carbonitrile and 4-oxo-7-(pyrid-4-yl)-5-(2,2,2-trifluoroethyl)-2-{[2-(trimethylsilyl)ethoxy]methyl}-4,5-dihydro-2H-pyrazolo[4,3-c]quinoline-8-carbonitrile, in the form of a white powder (1.8 hydrochloride; yield 15%).

LCMS (Method C): MH$^+$=369.9, RT=6.82 min
$^1$H NMR (400 MHz, DMSO-d$_6$): δ ppm 8.92 (d, 2 H) 8.80 (s, 1 H) 8.61 (br. s, 1 H) 8.08 (s, 1 H) 7.90 (d, 2 H) 5.47 (d, 1 H) 5.43 (d, 1 H)

EXAMPLE 11

4-oxo-7-(pyrid-4-yl)-5-(2,2,2-trifluoroethyl)-4,5-dihydro-2H-pyrazolo[4,3-c]quinoline-8-carboxylic acid hydrochloride (Compound 202)

A solution of 4-oxo-7-(pyrid-4-yl)-5-(2,2,2-trifluoroethyl)-1-{[2-(trimethylsilyl)ethoxy]-methyl}-4,5-dihydro-2H-pyrazolo[4,3-c]quinoline-8-carbonitrile and 4-oxo-7-(pyrid-4-yl)-5-(2,2,2-trifluoroethyl)-2-{[2-(trimethylsilyl)ethoxy]methyl}-4,5-dihydro-2H-pyrazolo[4,3-c]quinoline-8-carbonitrile [described in Step 10.1] (0.23 g, 0.46 mmol) in a mixture of 5 mL of acetic acid and 5 mL of concentrated hydrochloric acid is stirred for 80 minutes at 160° C. The mixture is concentrated to dryness. The brown residue obtained is taken up in MeOH and precipitated from ethyl ether. After filtering off and drying under vacuum, 182 mg of a beige-coloured powder are obtained (hydrochloride, 2.8 H$_2$O; yield: 93%).

LCMS (Method A): MH$^+$=389.0, RT=4.37 min
$^1$H NMR (400 MHz, DMSO-d$_6$): δ ppm 13.33 (br. s., 1 H) 8.88-8.97 (m, 3 H) 8.55 (br. s., 1 H) 7.96 (d, 2 H) 7.81 (s, 1 H) 5.40 (d, 1 H) 5.36 (d, 1 H)

EXAMPLE 12

3-[4-oxo-5-(2,2,2-trifluoroethyl)-4,5-dihydro-1H-pyrazolo[4,3-c]quinolin-7-yl]pyridine-2-carboxylic acid hydrochloride (Compound 203)

Step 12.1. 3-[4-oxo-1-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid and 3-[4-oxo-2-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid Sodium hydroxide (1M) (3.1 mL, 3.1 mmol) is added to a solution of methyl 3-[4-oxo-1-(tetrahydro-2H-pyran-2-yl)-5-(2,2,2-trifluoroethyl)-4,5-dihydro-1H-pyrazolo[4,3-c]quinolin-7-yl]pyridine-2-carboxylate [obtained via the process described in Step 7.2.] (1.0 g, 2.06 mmol) in 15 mL of DMSO at 40° C. The reaction mixture is stirred for 15 minutes at 40° C. and then poured into water and acidified with 30 mL of 0.1M hydrochloric acid solution to reach pH=3-4. After extraction with EtOAc, the organic phase is washed with saturated NaCl solution, dried over Na$_2$SO$_4$ and concentrated to dryness to give 890 mg of a white solid (yield: 92%).

LCMS (Method A): MH$^+$=473.1, RT=6.73 min

Step 12,2. 3-[4-oxo-5-(2,2,2-trifluoroethyl)-4,5-dihydro-1H-pyrazolo[4,3-c]quinolin-7-yl]pyridine-2-carboxylic acid hydrochloride To a solution of 3-[4-oxo-1-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid and 3-[4-oxo-2-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid (50 mg, 0.11 mmol) in 1 mL of DCM is added a 4M solution of hydrogen chloride in dioxane (0.26 mL, 1.06 mmol). After stirring at room temperature for 1 hour, the reaction mixture is filtered. The solid is washed with DCM and dried under vacuum to give 42 mg of a white powder (hydrochloride; yield: 93%).

LCMS (Method E); MH$^+$=389.0, RT=1.58 min
$^1$H NMR (400 MHz, DMSO-d$_6$): δ ppm 8.68 (dd, 1 H) 8.46 (s, 1 H) 8.26 (d, 1 H) 7.99 (dd, 1 H) 781 (s, 1 H) 7.70 (dd, 1 H) 7,42 (dd, 1 H) 5.35 (d, 1 H) 5.30 (d, 1 H)

EXAMPLE 13

4-oxo-7-(pyrid-4-yl)-5-(2,2,2-trifluoroethyl)-4,5-dihydro-2H-pyrazolo[4,3-c]quinoline-8-carboxamide (Compound 205)

A mixture of 4-oxo-7-(pyrid-4-yl)-5-(2,2,2-trifluoroethyl)-4,5-dihydro-2H-pyrazolo[4,3-c]quinoline-8-carboxylic acid [Example 11] (38 mg, 010 mmol), ammonium bicarbonate (46 mg, 0.59 mmol) and di-tert-butyl dicarbonate (47 mg, 0.22 mmol) in 1 mL of pyridine/EtOAc (1/1) is stirred at room temperature under nitrogen for 16 hours and then concentrated to dryness. After purification by preparative HPLC on a C18 reverse phase [eluent A: H$_2$O/0.1M CH$_3$COONH$_4$ (90/10); eluent B: CH$_3$CN/0.1M CH$_3$COONH$_4$ (90/10); gradient A/B: 95/5 to 50/50], 3 mg of a white powder are obtained (8%).

LCMS (Method C); MH$^+$=388.0, RT=5.78 min
$^1$H NMR (500 MHz, DMSO-d$_6$): δ ppm 14.37 (br. s., 1 H) 8.65-8.68 (m, 2 H) 8.47 (br. s., 1 H) 8.36 (s, 1 H) 7.99 (s, 1 H) 7.77 (s, 1 H) 7.53 (br. s., 1 H) 7.48-7.50 (m, 2 H) 5.43 (d, 1 H) 5.39 (d, 1 H)

EXAMPLE 14

7-[2-(morpholin-4-ylcarbonyl)pyrid-3-yl]-5-(2,2,2-trifluoroethyl)-1,5-dihydro-4H-pyrazolo[4,3-c]quinolin-4-one hydrochloride (Compound 206)

Step 14.1. 7-[2-(morpholin-4-ylcarbonyl)pyrid-3-yl]-1-(tetrahydro-2H-pyran-2-yl-5-(2,2,2-trifluoroethyl)-1,5-dihydro-4H-pyrazolo[4,3-c]quinolin-4-one and 7-[2-(morpholin-4-ylcarbonyl)pyrid-3-yl]-2-(tetrahydro-2H-pyran-2-yl)-5-(2,2,2-trifluoroethyl)-1,5-dihydro-4H-pyrazolo[4,3-c]quinolin-4-one To a solution of 3-[4-oxo-1-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid and 3-[4-oxo-2-(tetrahydro-2H-pyran-2-yl)-5-(2,2,2-trifluoroethyl)-4,5-dihydro-1H-pyrazolo[4,3-c]quinolin-7-yl]pyridine-2-carboxylic acid [described in Step 12.1.] (100 mg, 0.21 mmol) in 5 mL of anhydrous THF at room temperature under nitrogen are successively added triethylamine (60 μL, 0.53 mmol), PyBOP® (132 mg, 0.25 mmol) and, after stirring for 10 minutes, morpholine (22 to μL, 22 mg, 0.25 mmol). The solution is stirred for 3 hours, poured into saturated aqueous NaHCO₃ solution and extracted with EtOAc. The organic phase is washed with saturated aqueous NaCl solution, dried over Na₂SO₄, and concentrated to dryness. After purification by flash chromatography (DCM/EtOH: 100/0 to 95/5), 46 mg of a white solid are obtained (yield: 36%).

LCMS (Method A): MH⁺=542.1, RT=7.18 min

Step 14.2. 7-[2-(morpholin-4-ylcarbonyl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(morpholin-4-ylcarbonyl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(morpholin-4-ylcarbonyl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (hydrochloride, 0.7 H₂O; yield 78%).

LCMS (Method A): MH⁺=458.1, RT=5.95 min

¹H NMR (400 MHz, DMSO-d₆): δ ppm 8.68 (dd, 1 H) 8.49 (br. s., 1 H) 8.28 (d, 1 H) 8.03 (dd, 1 H) 7.81 (s, 1 H) 7.66 (dd, 1 H) 7.46 (dd, 1 H) 5.33 (d, 1 H) 5.29 (d, 1 H) 3.45-3.52 (m, 2 H) 3.33-3.41 (m, 2 H) 3.05-3.11 (m, 2 H) 2.98-3.04 (m, 2 H)

EXAMPLE 15

N-{3-[4-oxo-5-(2,2,2-trifluoroethyl)-4,5-dihydro-1H-pyrazolo[4,3-c]quinolin-7-yl]pyrid-2-yl}acetamide hydrochloride (Compound 223)

Step 15.1 N-{3-[4-oxo-1-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide and N-{3-[4-oxo-2-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide Acetic anhydride (1.28 mL, 13.5 mmol) is added to a solution of 7-(2-aminopyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-aminopyrid-3-yl)-2-(tetrahydro-2H-pyran-2-yl)-5-(2,2,2-trifluoroethyl)-1,5-dihydro-4H-pyrazolo[4,3-c]quinolin-4-one [described in Step 2.1.] (3.0 g, 6.77 mmol) in 34 mL of pyridine heated to 80° C. After stirring at 80° C. for 2.5 hours, the reaction medium is cooled and concentrated to dryness. After purification by flash chromatography on silica (DCM/EtOAc: 100/0 to 70/30), 2.1 g of a white powder are obtained (yield 63%), LCMS (Method A): MH⁺=486.2, RT=6.69 min

Step 15.2. N-{4-[4-oxo-5-(2,2,2-trifluoroethyl)-4,5-dihydro-1H-pyrazolo[4,3-c]quinolin-7-yl]pyrid-3-yl}acetamide hydrochloride The product is obtained according to the procedure described in Step 3.4. starting with N-{3-[4-oxo-1-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide and N-{3-[4-oxo-2-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide, in the form of a white powder (hydrochloride, 1.5 H₂O; yield 66%).

LCMS (Method A); MH⁺=402.0, RT=5.56 min

¹H NMR (400 MHz, DMSO-d₆): δ ppm 10.34 (s, 1 H) 8.52 (dd, 1 H) 8.44 (s, 1 H) 8.28 (d, 1 H) 8.05 (dd, 1 H) 7.82 (s, 1 H) 7.54 (dd, 1 H) 7.48 (dd, 1 H) 5.33 (d, 1 H) 5.29 (d, 1 H) 1.91 (s, 3 H)

EXAMPLE 16

N-{2-[4-oxo-5-(2,2,2-trifluoroethyl)-4,5-dihydro-2H-pyrazolo[4,3-c]quinolin-7-yl]phenyl}methanesulfonamide (Compound 232)

Step 16.1. N-{2-[4-oxo-5-(2,2,2-trifluoroethyl)-1-{[2-(trimethylsilyl)ethoxy]methyl}-4,5-dihydro-2H-pyrazolo[4,3-c]quinolin-7-yl]phenyl}methanesulfonamide and N-{2-[4-oxo-5-(2,2,2-trifluoroethyl)-2-{[2-(trimethylsilyl)ethoxy]methyl}-4,5-dihydro-2H-pyrazolo[[4,3-c]quinolin-7-yl]phenyl}methanesulfonamide Methanesulfonyl chloride (33 µL, 0.41 mmol) is added to a solution of 7-(2-aminophenyl)-5-(2,2,2-trifluoroethyl)-1-{[2-(trimethylsilyl)ethoxy]methyl}-2,5-dihydro-4H-pyrazolo[4,3-c]quinolin-4-one and 7-(2-aminophenyl)-5-(2,2,2-trifluoroethyl)-2-{[2-(trimethylsilyl)-ethoxy]methyl}-2,5-dihydro-4H-pyrazolo[4,3-c]quinolin-4-one [obtained according to the process described in Step 7.2. starting with 2-chloroaniline and 7-(4,4,5,5-tetramethyl-1,3,2-dioxaborolan-2-yl)-5-(2,2,2-trifluoroethyl)-2-{[2-(trimethylsilyl)ethoxy]methyl}-2,5-dihydro-4H-pyrazolo[4,3-c]quinolin-4-one obtained according to the process described in Step 7.1. starting with 7-bromo-1-{[2-(trimethylsilyl)ethoxy]methyl}-1,5-dihydro-4H-pyrazolo[4,3-c]quinolin-4-one and 7-bromo-2-{[2-(trimethylsilyl)ethoxy]methyl}-1,5-dihydro-4H-pyrazolo[4,3-c]quinolin-4-one described in Step 3.1.] (0.20 g, 0.41 mmol) in 2 mL of pyridine at room temperature. After stirring for 1 hour, the reaction medium is poured into molar hydrochloric acid solution and extracted with EtOAc. The organic phase is washed with water, dried over Na₂SO₄ and concentrated to dryness. After purification by flash chromatography on silica (cyclohexene/EtOAc: 100/0 to 50/50), 195 mg of a white powder are obtained (yield: 84%).

LCMS (Method A): MH⁺=567.0, RT=9.70 min

Step 16.2. N-{2-[4-oxo-5-(2,2,2-trifluoroethyl)-4,5-dihydro-2H-pyrazolo[4,3-c]quinolin-7-yl]phenyl}methanesulfonamide The product is obtained according to the procedure described in Step 4.3. starting with N-{2-[4-oxo-5-(2,2,2-trifluoroethyl)-1-{[2-(trimethylsilyl)ethoxy]methyl}-4,5-dihydro-2H-pyrazolo[4,3-c]quinolin-7-yl]phenyl}methanesulfonamide and N-{2-[4-oxo-5-(2,2,2-trifluoroethyl)-2-{[2-(trimethylsilyl)ethoxy]methyl}-4,5-dihydro-2H-pyrazolo[4,3-c]quinolin-7-yl]phenyl}methanesulfonamide, in the form of a white powder (yield 74%).

LCMS (Method B): MH⁺=437.1, RT=13.31 min

¹H NMR (400 MHz, DMSO-d₆): δ ppm 14.29 (br. s., 1 H) 9.08 (br. s., 1 H) 8.39 (br. s, 1 H) 8.24 (d, 1 H) 7.79 (s, 1 H) 7.37-7.56 (m, 5 H) 5.35 (d, 1 H) 5.33 (d, 1 H) 2.74 (s, 3 H)

EXAMPLE 17

N-methyl-N-{3-[4-oxo-5-(2,2,2-trifluoroethyl)-4,5-dihydro-1H-pyrazolo[4,3-c]quinolin-7-yl]pyrid-2-yl}acetamide hydrochloride (Compound 241)

Step 17.1. N-methyl-N-{3-[4-oxo-1-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide and N-methyl-N-{3-[4-oxo-2-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide N-{3-[4-oxo-1-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide and N-{3-[4-oxo-2-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide [described in Step 15.1] (0.69 g, 1.43 mmol) and methyl iodide (0.27 mL, 4.33 mmol) are successively added to sodium hydride (60% suspension in oil, 0.17 g, 4.33 mmol) in 16 mL of anhydrous DMF under nitrogen at room temperature. After stirring for 15 minutes, the reaction mixture is poured into molar potassium hydrogen sulfate solution and extracted with EtOAc. The organic phase is washed with water and with saturated aqueous NaCl solution, dried over $Na_2SO_4$ and concentrated to dryness. After purification by flash chromatography on silica (DCM/EtOAc: 100/0 to 50/50), 0.57 g of a white powder is obtained (yield: 80%).

LCMS (Method A): $MH^+$=500.3, RT=1.16 min

Step 17.2. N-methyl-N-{3-[4-oxo-5-(2,2,2-trifluoroethyl)-4,5-dihydro-1H-pyrazolo[4,3-c]quinolin-7-yl]pyrid-2-yl}acetamide hydrochloride The product is obtained according to the procedure described in Step 1.7. starting with N-methyl-N-{3-[4-oxo-1-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide and N-methyl-N-{3-[4-oxo-2-(tetrahydro-2H-pyran-2-yl)-5-(2,2,2-trifluoroethyl)-4,5-dihydro-1H-pyrazolo[4,3-c]quinolin-7-yl]pyrid-2-yl}acetamide, in the form of a white powder (hydrochloride, 1 $H_2O$; yield 58%).

LCMS (Method A): $MH^+$=416.1, RT=6.15 min $^1$H NMR (400 MHz, DMSO-$d_6$): δ ppm 8.62 (d, 1 H) 8.46 (br. s., 1 H) 8.26 (d, 1 H) 8.03 (d, 1 H) 7.82 (s, 1 H) 7.63 (dd, 1 H) 7.38 (d, 1 H) 5.27-5.41 (m, 2 H) 2.97 (s, 3 H) 1.70 (s, 3 H)

EXAMPLE 18

7-[2-(1,4-diazepan-1-yl)pyrid-3-yl]-5-(2,2,2-trifluoroethyl)-1,5-dihydro-4H-pyrazolo[4,3-c]quinolin-4-one hydrochloride (Compound 244)

Step 18.1. 7-[2-(1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one A solution of 7-(2-fluoropyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-fluoropyrid-3-yl)-2-(tetrahydro-2H-pyran-2-yl)-5-(2,2,2-trifluoroethyl)-1,5-dihydro-4H-pyrazolo[4,3-c]quinolin-4-one (1.0 g, 2.16 mmol) in 11 mL of homopiperazine is heated for 4 hours at 180° C. under microwave irradiation in a sealed reactor. The solution is cooled to room temperature and poured into water. The white precipitate formed is filtered off and purified by flash chromatography on silica (DCM/EtOH: 100/0 to 70/30). 745 mg of a white solid are obtained (yield: 66%).

LCMS (Method A): $MH^+$=527.4, RT=5.90 min

Step 18.2. 7-[2-(1,4-diazepan-1-yl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (hydrochloride, 1 $H_2O$; yield 75%).

LCMS (Method A): $MH^+$=443.2, RT=5.13 min $^1$H NMR (400 MHz, DMSO-$d_6$): δ ppm 8.90 (br. s., 2 H) 8.44 (br. s., 1 H) 8.28 (d, 1 H) 8.24 (dd, 1 H) 7.80 (s, 1 H) 7.68 (d, 1 H) 7.47 (dd, 1 H) 7.05 (dd, 1 H) 5.35 (d, 1 H) 5.31 (d, 1 H) 3.58-3.62 (m, 2 H) 3.13-3.24 (m, 4 H) 2.98 3.06 (m, 2 H) 1.80-1.89 (m, 2 H)

EXAMPLE 19

7-[2-(piperidin-1-yl)pyrid-3-yl]-5-(2,2,2-trifluoroethyl)-1,5-dihydro-4H-pyrazolo[4,3-c]quinolin-4-one hydrochloride (Compound 245)

Step 19.1. 7-[2-(piperidin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(piperidin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one A solution of 7-(2-fluoropyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-fluoropyrid-3-yl)-2-(tetrahydro-2H-pyran-2-yl)-5-(2,2,2-trifluoroethyl)-1,5-dihydro-4H-pyrazolo[4,3-c]quinolin-4-one (0.4 g, 0.896 mmol) and cyclohexylamine (0.76 g, 8.96 mmol) in 5 mL of NMP is heated for 2 hours at 185° C. in a sealed reactor under microwave irradiation. The reaction mixture is poured into water and extracted with EtOAc. The organic phase is washed with saturated aqueous NaCl solution, dried over $Na_2SO_4$ and concentrated to dryness. After purification by flash chromatography on silica (DCM/EtOH: 100/0 to 90/10), 232 mg of product are obtained in the form of a solid (yield: 51%).

LCMS (Method E): $MH^+$=512.1, RT=2.01 min

Step 19.2. 7-[2-(piperidin-1-yl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(piperidin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(piperidin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (hydrochloride, 1.3 $H_2O$; yield 86%).

LCMS (Method A): MH+=428.2, RT=6.13 min

¹H NMR (250 MHz, DMSO-d₆): δ ppm 8.46 (s, 1 H) 8.31 (d, 1 H) 8.23 (dd, 1 H) 7.83-7.98 (m, 2 H) 7.62 (d, 1 H) 7.23 (dd, 1 H) 5.35 (d, 1 H) 5.30 (d, 1 H) 3.15 (br. s., 4 H) 1.46 (br. s., 6 H)

EXAMPLE 20

7-[2-(4-cyclopropylpiperazin-1-yl)pyrid-3-yl]-5-(2,2,2-trifluoroethyl)-1,5-dihydro-4H-pyrazolo[4,3-c]quinolin-4-one hydrochloride (Compound 267)

Step 20.1. 7-[2-(4-cyclopropylpiperazin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(4-cyclopropyl piperazin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one 7-(2-Chloropyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-chloropyrid-3-yl)-2-(tetrahydro-2H-pyran-2-yl)-5-(2,2,2-trifluoroethyl)-1,5-dihydro-4H-pyrazolo[4,3-c]quinolin-4-one [described in Step 7.2.] (0.4 g, 0.86 mmol), sodium tert-butoxide (0.83 g, 8.64 mmol), 1-cyclopropylpiperazine (0.69 g, 3.46 mmol), 9 mL of anhydrous DMF and the catalyst [Pd(µ-Br)(tBu₃P)]₂ (0.14 g, 0.18 mmol) are successively introduced into a microwave reactor under argon. The reactor is sealed and the mixture is stirred for 30 minutes at 100° C. under microwave irradiation. The mixture is cooled and adsorbed onto silica. After purification by flash chromatography on silica (DCM/EtOAc: 100/0 to 50/50), 75 mg of a yellow powder are obtained (yield: 16%).

LCMS (Method E): MH+=553.0, RT=1.92 min

Step 20.2. 7-[2-(4-cyclopropylpiperazin-1-yl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(4-cyclopropylpiperazin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(4-cyclopropyl-piperazin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (3 hydrochloride, 3H₂O; yield 70%).

LCMS (Method A): MH+=469.2, RT=5.32 min

¹H NMR (250 MHz, DMSO-d₆): δ ppm 10,57 (br. s., 1 H) 8.46 (br. s., 1 H) 8.28-8.33 (m, 2 H) 7.88 (s, 1 H) 7.71 7.75 (m, 2 H) 7.19 (dd, 1 H) 5.38 (d, 1 H) 5.34 (d, 1 H) 3.53 (d, 2 H) 3.38 (d, 2 H) 3.03-3.24 (m, 4 H) 2.85 (br. s., 1 H) 1.04 (br. s., 2 H) 0.70 0.78 (m, 2 H)

EXAMPLE 21

7-[2-(4-methyl-1,4-diazepan-1-yl)pyrid-3-yl]-5-(2,2,2-trifluoroethyl)-1,5-dihydro-4H-pyrazolo[4,3-c]quinolin-4-one hydrochloride (Compound 270)

Step 21.1. 7-[2-(4-methyl-1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(4-methyl-1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one To a solution of 7-[2-(1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one [described in Step 18.1] (0.2 g, 0.38 mmol) in 17 mL of MeOH is added formaldehyde (0.356 mL, 3.80 mmol) and the solution is stirred at room temperature for 1 hour. NaBH₄ (72 mg, 1.90 mmol) is added portionwise at 0° C., and evolution of gas is observed. The reaction mixture is stirred at room temperature for 3 hours and then poured into water and extracted with EtOAc. The organic phase is washed with saturated aqueous NaCl solution, dried over Na₂SO₄ and concentrated to dryness. The white solid obtained is taken up in diisopropyl ether and, after filtering off, 142 mg of product are obtained in the form of a white powder (yield: 70%).

LCMS (Method C): MH+=541.2, RT=7.68 min

Step 21.2. 7-[2-(4-methyl-1,4-diazepan-1-yl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(4-methyl-1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(4-methyl-1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (2 hydrochloride, 5.5 H₂O; yield: 28%).

LCMS (Method A): MH+=457.2, RT=5.21 min

¹H NMR (250 MHz, DMSO-d₆): δ ppm 9.61 (br. s., 1 H) 8.40 (br. s., 1 H) 8.18-8.29 (m, 2 H) 7.76 (s, 1 H) 7.64 (dd, 1 H) 7.45 (d, 1 H) 7.01 (dd, 1 H) 5.26-5.42 (m, 2 H) 2.91-4.04 (m, 8 H) 2.73-2.80 (m, 3 H) 1.90 (br. s., 2 H)

EXAMPLE 22

7-[2-(4-cyclopropyl-1,4-diazepan-1-yl)pyrid-3-yl]-5-(2,2,2-trifluoroethyl)-1,5-dihydro-4H-pyrazolo[4,3-c]quinolin-4-one hydrochloride (Compound 271)

Step 22.1. 7-[2-(4-cyclopropyl-1,4-diazepan-1-yl)pyrid-3-yl]-1-(tetrahydro-2H-pyran-2-yl)-5-(2,2,2-trifluoroethyl)-1,5-dihydro-4-Hpyrazolo[4,3-c]quinolin-4-one and 7-[2-(4-cyclopropyl-1,4-diazepan-1-yl)pyrid-3-yl]-2-(tetrahydro-2H-pyran-2-yl-5-(2,2,2-trifluoroethyl)-1,5-dihydro-4H-pyrazolo[4,3-c]quinolin-4-one To a solution of 7-[2-(1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one [described in Step 18.1] (0.1 g, 0.19 mmol) dissolved in 8 mL of MeOH is added (1-methoxycyclopropoxy)trimethylsilane (36.5 mg, 0.23 mmol). The mixture is stirred for 30 minutes at room temperature, followed by addition of NaBH₃CN (24 mg, 0.38 mmol). Evolution of gas is observed, and the mixture is stirred for 72 hours. The resulting mixture is poured into aqueous solution, extracted with EtOAc, washed with saturated aqueous NaCl solution, dried over anhydrous Na₂SO₄, filtered and concentrated to dryness. 85 mg of a white solid are obtained (yield: 78%).

LCMS (Method A): MH+=567.1, RT=6.11 min

Step 22,2. 7-[2-(4-cyclopropyl-1,4-diazepan-1-yl) pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(4-cyclopropyl-1,4-diazepan-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(4-cyclopropyl-1,4-diazepan-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (hydrochloride, 3.6 $H_2O$; yield 57%).

LCMS (Method A): $MH^+$=483.2, RT=5.36 min $^1$H NMR (250 MHz, DMSO-$d_6$): δ ppm 9.95 (br. s., 1 H) 8.44 (br. s., 1 H) 8.19-8.29 (m, 2 H) 7.77 (s, 1 H) 7.66 (dd, 1 H) 7.46 (d, 1 H) 7.02 (dd, 1 H) 5.33 (q, 2 H) 3.54 (br. s., 2 H) 3.12-3.47 (m, 4 H) 3.06 (br. s., 2 H) 2.88 (br. s., 1 H) 1.96 (br. s., 2 H) 1.08-1.06 (m, 2 H) 0.72-0.84 (m, 2 H)

EXAMPLE 23

7-[2-(3-fluoropyrrolidin-1-yl)pyrid-3-yl]-5-(2,2,2-trifluoroethyl)-1,5-dihydro-4H-pyrazolo[4,3-c]quinolin-4-one (Compound 272)

Step 23.1. 7-[2-(3-fluoropyrrolidin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(3-fluoropyrrolidin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one To a solution of diethylaminosulfur trifluoride (32 mg, 0.20 mmol) in 4 mL of DCM cooled to −70° C. is added 7-[2-(3-hydroxypyrrolidin-1-yl)pyrid-3-yl]-1-(tetrahydro-2H-pyran-2-yl)-5-(2,2,2-trifluoroethyl)-1,5-dihydro-4H-pyrazolo[4,3-c]quinolin-4-one and 7-[2-(3-hydroxypyrrolidin-1-yl)pyrid-3-yl]-2-(tetrahydro-2H-pyran-2-yl)-5-(2,2,2-trifluoroethyl)-1,5-dihydro)-4H-pyrazolo[4,3-c]quinolin-4-one [obtained according to the process described in Step 18.1. starting with pyrrolidin-3-ol] (85 mg, 0.17 mmol) dissolved in 3 mL of DCM. The mixture is stirred for 2 hours at room temperature, saturated aqueous $NaHCO_3$ solution is then added and the resulting mixture is extracted with DOM. The organic phase is washed with saturated aqueous NaCl solution, dried over $Na_2SO_4$ and concentrated to dryness. After purification by flash chromatography on silica (DCM/EtOH: 100/0 to 90/10), 38 mg of a white solid are obtained (yield: 43%).

LCMS (Method E); $MH^+$=516.1, RT=1.89 min

Step 23.2. 7-[2-(3-fluoropyrrolidin-1-yl)pyrid-3-yl]-5-(2,2,2-trifluoroethyl)-1,5-dihydro-4H-pyrazolo[4,3-c]quinolin-4-one hydrochloride The product is obtained according to the procedure described in Step 1.7. starting with 7-[2-(3-fluoropyrrolidin-1-yl)pyrid-3-yl]-1-(tetrahydro-2H-pyran-2-yl-5-(2,2,2-trifluoroethyl)-1,5-dihydro-4H-pyrazolo[4,3-c]quinolin-4-one and 7-[2-(3-fluoropyrrolidin-1-yl)pyrid-3-yl]-2-(tetrahydro-2H-pyran-2-yl)-5-(2,2,2-trifluoroethyl)-1,5-dihydro-4H-pyrazolo[4,3-c]quinolin-4-one, in the form of a white powder (hydrochloride. $H_2O$; yield 47%).

LCMS (Method A): $MH^+$=432.1, RT=5.50 min $^1$H NMR (250 MHz, DMSO-$d_6$): δ ppm 8.45 (br. s., 1 H) 8.26 (d, 1 H) 8.17 (dd, 1 H) 7.82 (s, 1 H) 7.76 (br. s., 1 H) 7.41 (d, 1 H) 7.02 (br. s., 1 H) 5.15-5.39 (m, 3 H) 3.18-3.48 (m, 4 H) 1.83-2,22 (m, 2 H)

EXAMPLE 24

7-(2-hydroxypyrid-3-yl)-5-(2,2,2-trifluoroethyl)-1,5-dihydro-4H-pyrazolo[4,3-c]quinolin-4-one (Compound 274)

Step 24.1. 7-(2-methoxypyrid-3-yl)-1-(tetrahydro-2H-pyran-2-yl)-5-(2,2,2-trifluoroethyl)-1,5-dihydro-4H-pyrazolo[4,3-c]quinolin-4-one and 7-(2-methoxypyrid-3-yl)-2-(tetrahydro-2H-pyran-2-yl)-5-(2,2,2-trifluoroethyl)-1,5-dihydro-4H-pyrazolo[4,3-c]quinolin-4-one To a solution of 7-bromo-1-(tetrahydro-2H-pyran-2-yl)-1,5-dihydro-4H-pyrazolo[4,3-c]quinolin-4-one and 7-bromo-3-(tetrahydro-2H-pyran-2-yl)-1,5-dihydro-4H-pyrazolo[4,3-c]quinolin-4-one [described in Step 1.4.] (0.40 g, 0.93 mmol) dissolved in 10 mL of DMF placed in a microwave reactor are added 2-methoxy-3-pyridineboronic acid (0.284 g, 1.86 mmol), $Cs_2CO_3$ (1.2 g, 3.72 mmol), 1 mL of degassed water and the catalyst $PdCl_2$(dppf) (0.159 mg, 0.2 mmol). The reactor is sealed and the mixture is stirred at 110° C. under microwave irradiation for 10 minutes under nitrogen. The reaction mixture is cooled, poured into water and extracted with EtOAc. The organic phase is washed with saturated aqueous NaCl solution, dried over $Na_2SO_4$ and concentrated to dryness. After purification by flash chromatography on silica (DCM/EtOH: 100/0 to 90/10), 103 mg of a yellow solid are obtained (yield: 24%).

LCMS (Method A): $MH^+$=459.2, RT=9.04 min

Step 24.2. 7-(2-hydroxypyrid-3-yl)-5-(2,2,2-trifluoroethyl)-1,5-dihydro-4H-pyrazolo[4,3-c]quinolin-4-one To a solution of 7-(2-methoxypyrid-3-1)-1-(tetrahydro-2H-pyran-2-1)-5-(2,2,2-trifluoroethyl)-1,5-dihydro-4H-pyrazolo[4,3-c]quinolin-4-one and 7-(2-methoxypyrid-3-yl)-2-(tetrahydro-2H-pyran-2-yl)-5-(2,2,2-trifluoroethyl)-1,5-dihydro-4H-pyrazolo[4,3-c]quinolin-4-one (90 mg, 0.20 mmol) in a DCM/MeOH mixture (50/50) is added a 4M solution of hydrogen chloride in anhydrous dioxane (2 mL, 2.45 mmol). The solution is stirred at room temperature for 10 days and then poured into diisopropyl ether. The precipitate formed is filtered off and washed with EtOH. 52 mg of a white solid are obtained (yield: 65%).

LCMS (Method A): $MH^+$=361.0, RT=5.91 min $^1$H NMR (250 MHz, DMSO-$d_6$): δ ppm 14.30 (br. s., 1 H) 11.92 (br. s., 1 H) 8.20-8.80 (m, 1 H) 8.17 (d, 1 H) 8.08 (br. s., 1 H) 7.85 (d, 2 H) 7.48 (d, 1 H) 6.38 (t, 1 H) 5.31 (q, 2 H)

EXAMPLE 25

7-(1-oxidopyrid-2-yl)-5-(2,2,2-trifluoroethyl)-1,5-dihydro-4H-pyrazolo[4,3-c]quinolin-4-one hydrochloride (Compound 275)

Step 25.1. 7-(1-oxidopyrid-2-yl)-1-(tetrahydro-2H-pyran-2-yl)-5-(2,2,2-trifluoroethyl)-1,5-dihydro-4H-pyrazolo[4,3-c]quinolin-4-one and 7-(1-oxidopyrid-2-yl-2-(tetrahydro-2H-pyran-2-yl)-5-(2,2,2-trifluoroethyl)-1,5-dihydro-4H-pyrazolo[4,3-c]quinolin-4-one meta-Chloroperbenzoic acid (585 mg, 2.62 mmol) is added at 0° C. to a suspension of 7-(pyrid-2-yl)-1-(tetrahydro-2H- pyran-2-yl)-5-(2,2,2-trifluoroethyl)-2,5-dihydro-4H-pyrazolo[4,3-c]quinolin-4-one and 7-(pyrid-2-yl)-2-(tetrahydro-2H-pyran-2-yl)-5-(2,2,2-trifluoroethyl)-2,5-dihydro-4H-pyrazolo[4,3-c]quinolin-4-one (280 mg, 0.65 mmol) in 5 mL of DCM. The mixture is stirred for 3 hours at room temperature. After purification by flash chromatography on amine phase (DCM/EtOAc: 95/5 to 80/20 and then DCM/EtOH: 95/5), 120 mg of a white powder are obtained (yield: 43%).

LCMS (Method A): MH$^+$=445.2, RT=6.69 min

Step 25.2. 7-(1-oxidopyrid-2-yl)-5-(2,2,2-trifluoroethyl)-1,5-dihydro-4H-pyrazolo[4,3-c]quinolin-4-one hydrochloride The product is obtained according to the procedure described in Step 1.7. by treating 7-(1-oxidopyrid-2-yl)-1-(tetrahydro-2H-pyran-2-yl)-5-(2,2,2-trifluoroethyl)-1,5-dihydro-4H-pyrazolo[4,3-c]quinolin-4-one and 7-(1-oxidopyridin-2-yl)-2-(tetrahydro-2H-pyran-2-yl)-5-(2,2,2-trifluoroethyl)-1,5-dihydro-4H-pyrazolo[4,3-c]quinolin-4-one with 4M HCl in dioxane, in the form of a white powder (hydrochloride, 1 H$_2$O; yield 99%).

LCMS (Method A): MH$^+$=361.2, RT=5.53 min $^1$H NMR (250 MHz, DMSO-d$_6$): δ ppm 8.48 (br. s., 1 H) 8.39-8.43 (m, 1 H) 8.27 (d, 1 H) 8.15 (s, 1 H) 7.92 (d, 1 H) 7.70-7.76 (m, 1 H) 7.46-7.52 (m, 2 H) 5.36 (d, 1 H) 5.31 (d, 1 H)

The table that follows illustrates the chemical structures and the physical properties of a number of compounds according to the invention. In this table:

Me, Et, Pr, c-Pr and i-Pr represent, respectively, methyl, ethyl, propyl, cyclopropyl and isopropyl groups;

in the "salt" column "l" represents a compound in free base form, whereas "HCl" represents a compound in hydrochloride form and "TFA" represents a compound in the form of the trifluoroacetic acid salt.

TABLE

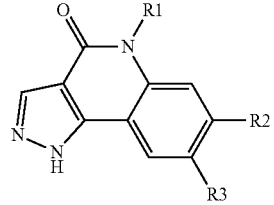

(I)

| Compound No. | R1 | R2 | R3 | Synthetic route | MH+ | RT (min) | LCMS method | Salt |
|---|---|---|---|---|---|---|---|---|
| 1 (Ex. 1) | CH2CF3 | 2-Pyridyl | H | A | 345.0 | 6.63 | A | HCl |
| 2 (Ex. 2) | CH2CF3 | 3-(2-aminopyridyl) | H | A | 360.1 | 4.83 | A | HCl |
| 3 | CH2CF3 | 2-fluorophenyl | H | A | 362.1 | 1.12 | H | / |
| 4 | Et | 2-Pyridyl | H | A | 291.2 | 2.17 | J | TFA |
| 5 | Et | 4-fluorophenyl | H | A | 308.3 | 7.16 | A | / |
| 6 | CH2CF3 | 4-Pyridyl | H | A | 345.0 | 5.25 | A | HCl |
| 7 | Et | 4-Pyridyl | H | A | 291.1 | 2.02 | J | HCl |
| 8 | Et | 2-(dimethylamino)phenyl | H | A | 333.2 | 2.97 | J | TFA |

TABLE-continued (I)

| Compound No. | R1 | R2 | R3 | Synthetic route | MH+ | RT (min) | LCMS method | Salt |
|---|---|---|---|---|---|---|---|---|
| 9 | Et | 4-(C(O)NH-CH2CH2CH2-N(CH3)2)-phenyl | H | A | 418.3 | 2.27 | J | TFA |
| 10 | Et | 4-(piperazin-1-yl)phenyl | H | A | 374 | 2.29 | J | TFA |
| 11 | Et | 4-(4-methylpiperazin-1-yl)phenyl | H | A | 388 | 2.34 | J | TFA |
| 12 | CH2CF3 | 2-(morpholine-4-carbonyl)phenyl | H | A | 457.2 | 6.73 | A | / |
| 13 | Et | 4-(C(O)NH-CH2CH2-N(CH3)2)-phenyl | H | A | 404.3 | 2.25 | J | TFA |
| 14 | CH2CF3 | 2-(morpholin-4-yl)phenyl | H | A | 429.1 | 8.12 | A | HCl |

TABLE-continued (I)

| Compound No. | R1 | R2 | R3 | Synthetic route | MH+ | RT (min) | LCMS method | Salt |
|---|---|---|---|---|---|---|---|---|
| 15 | Et | 4-(1-(dimethylamino)ethyl)phenyl | H | A | 361.3 | 2.30 | J | TFA |
| 16 | CH2CF3 | 2-(morpholinomethyl)phenyl | H | A | 443.0 | 5.33 | A | HCl |
| 17 | Et | 2-(morpholinomethyl)phenyl | H | A | 389.2 | 2.19 | I' | TFA |
| 18 | Et | 4-(piperazine-1-carbonyl)phenyl | H | A | 402 | 2.08 | I' | TFA |
| 19 | CH2CF3 | 3-(4-methylpiperazin-1-yl)phenyl | H | A | 442.0 | 5.26 | A | HCl |
| 20 | Et | 2-(piperazin-1-yl)pyrimidin-5-yl | H | A | 376.3 | 2.65 | I' | TFA |
| 21 | Et | 4-(4-methylpiperazine-1-carbonyl)phenyl | H | A | 416.3 | 2.18 | J | TFA |

TABLE-continued
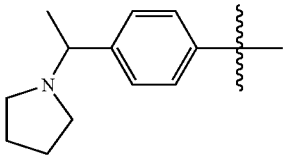 [SMILES: *c1ccc(C(C)N2CCCC2)cc1]
(I)
| Compound No. | R1 | R2 | R3 | Synthetic route | MH+ | RT (min) | LCMS method | Salt |
|---|---|---|---|---|---|---|---|---|
| 22 | Et | 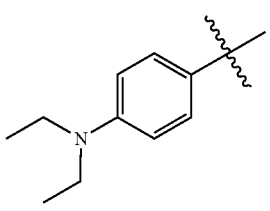 [SMILES: *c1ccc(N(CC)CC)cc1] | H | A | 387.3 | 2.22 | I' | TFA |
| 23 | CH2CF3 | 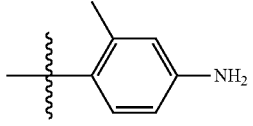 [SMILES: *c1ccc(N)cc1C] | H | A | 415.0 | 6.81 | A | HCl |
| 24 | Et | 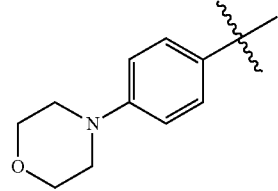 [SMILES: *c1ccc(N2CCOCC2)cc1] | H | A | 319 | 2.63 | I | TFA |
| 25 | CH2CF3 | 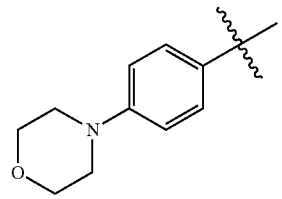 [SMILES: *c1ccc(N2CCOCC2)cc1] | H | A | 429.1 | 7.64 | A | HCl |
| 26 | Et | 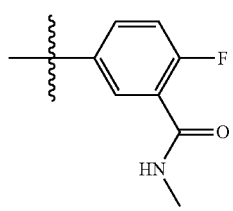 [SMILES: *c1ccc(F)c(C(=O)NC)c1] | H | A | 375.2 | 2.59 | I' | TFA |
| 27 | Et | 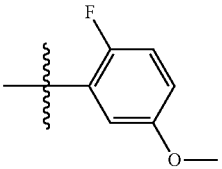 [SMILES: *c1cc(OC)ccc1F] | H | A | 365 | 2.44 | I' | / |
| 28 | Et |  | H | A | 338 | 3.20 | J | / |

TABLE-continued
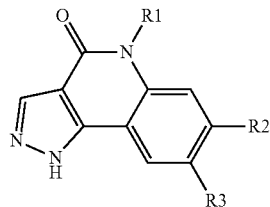
(I)
| Compound No. | R1 | R2 | R3 | Synthetic route | MH+ | RT (min) | LCMS method | Salt |
|---|---|---|---|---|---|---|---|---|
| 29 | Et | 2-chloro-4-(morpholine-4-carbonyl)phenyl | H | A | 437.2 | 2.79 | J | / |
| 30 | CH2CF3 | 4-(piperazin-1-yl)phenyl | H | A | 428.1 | 5.22 | A | HCl |
| 31 | Et | 2-(4-methylpiperazin-1-yl)pyrimidin-5-yl | H | A | 390 | 2.08 | I' | TFA |
| 32 | CH2CF3 | 4-(dimethylamino)phenyl | H | A | 387.0 | 7.62 | A | HCl |
| 33 | Et | 3-chloro-4-carbamoylphenyl | H | A | 367.2 | 2.54 | J | / |
| 34 | Et | 1H-indazol-5-yl | H | A | 330.2 | 2.39 | I' | / |
| 35 | Et | 3-(ethylcarbamoyl)phenyl | H | A | 361.2 | 3.49 | J | / |

TABLE-continued (I)

| Compound No. | R1 | R2 | R3 | Synthetic route | MH+ | RT (min) | LCMS method | Salt |
|---|---|---|---|---|---|---|---|---|
| 36 | Et | 5-linked, 2-F, 3-C(O)NH2 phenyl | H | A | 351.2 | 2.32 | I' | / |
| 37 | Et | 3-[C(O)NH-CH2CH2-N(Me)2] phenyl | H | A | 404.2 | 2.29 | J | TFA |
| 38 | Et | 4-(CH2-NH-C(O)-CH3) phenyl | H | A | 361.1 | 2.31 | I' | / |
| 39 | Et | 3-[C(O)NH-CH2CH2-OMe] phenyl | H | A | 391.2 | 3.43 | J | / |
| 40 | CH2CF3 | 3-hydroxyphenyl | H | A | 360.1 | 1.01 | H | / |
| 41 | CH2CF3 | 2-chloro-3-fluoro-pyridin-4-yl | H | A | 397.0 | 1.09 | H | / |

TABLE-continued
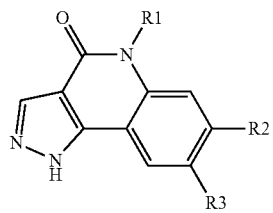
(I)
| Compound No. | R1 | R2 | R3 | Synthetic route | MH+ | RT (min) | LCMS method | Salt |
|---|---|---|---|---|---|---|---|---|
| 42 | CH2CF3 | ![furan-phenyl-NHiPr] | H | A | 481.2 | 5.93 | A | HCl |
| 43 | Et | ![2-(NHSO2Me)phenyl] | H | A | 383.2 | 2.74 | J | / |
| 44 | Et | ![2-aminophenyl] | H | A | 305.2 | 2.45 | J | TFA |
| 45 | Et | ![3-morpholinophenyl] | H | A | 375.2 | 2.84 | J | TFA |
| 46 | Et | ![2-(NHAc)phenyl] | H | A | 347.2 | 2.55 | J | / |
| 47 | Et | ![2-hydroxyphenyl] | H | A | 306.2 | 2.84 | J | / |

TABLE-continued
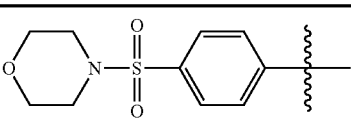
(I)
| Compound No. | R1 | R2 | R3 | Synthetic route | MH+ | RT (min) | LCMS method | Salt |
|---|---|---|---|---|---|---|---|---|
| 48 | Et |  | H | A | 439.2 | 2.92 | J | / |
| 49 | CH2CF3 | 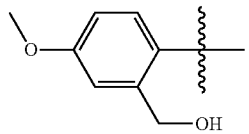 [SMILES: *c1ccc(OC)cc1CO] | H | A | 404.1 | 1.02 | H | / |
| 50 | Et |  | H | A | 56.2 | 3.14 | J | TFA |
| 51 | Et | 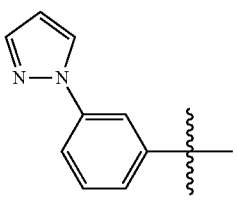 [SMILES: *c1cccc(-n2cccn2)c1] | H | A | 329 | 2.99 | J | TFA |
| 52 | Et |  | H | A | 321.1 | 3.05 | J | / |
| 53 | CH2CF3 | 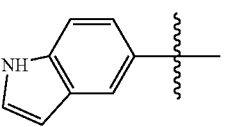 | H | A | 394.1 | 1.1 | H | / |
| 54 | Et |  | H | A | 336.1 | 2.7 | I' | / |
| 55 | CH2CF3 | 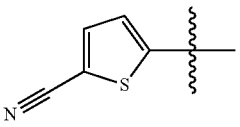 [SMILES: *c1ccc(C#N)s1] | H | A | 417.1 | 1.05 | H | / |
| 56 | Et |  | H | A | 361.1 | 4.09 | I' | TFA |

TABLE-continued (I)

| Compound No. | R1 | R2 | R3 | Synthetic route | MH+ | RT (min) | LCMS method | Salt |
|---|---|---|---|---|---|---|---|---|
| 57 | CH2CF3 | 2,5-dichloropyridin-3-yl | H | A | 411.0 | 1.12 | H | / |
| 58 | Et | 4-chloro-2-methoxyphenyl... | H | A | 354.1 | 3.07 | I' | / |
| 59 | Et | 3-(3-(dimethylamino)propylcarbamoyl)phenyl | H | A | 418.2 | 2.17 | I' | TFA |
| 60 | Et | 4-fluoro-2-hydroxyphenyl | H | A | 324.1 | 2.69 | I' | / |
| 61 | Et | 2-fluoro-4-methoxyphenyl | H | A | 338.1 | 3.27 | J | / |
| 62 | Et | 4-(aminomethyl)phenyl | H | A | 319.2 | 2.65 | J | TFA |
| 63 | Et | 2-fluoro-3-methoxyphenyl | H | A | 338.1 | 2.98 | I' | / |

TABLE-continued
(I)
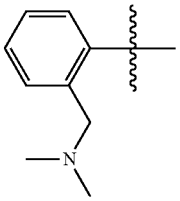 [SMILES: *c1ccccc1CN(C)C]
| Compound No. | R1 | R2 | R3 | Synthetic route | MH+ | RT (min) | LCMS method | Salt |
|---|---|---|---|---|---|---|---|---|
| 64 | Et | 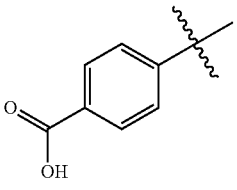 [SMILES: *c1ccc(C(=O)O)cc1] | H | A | 347.2 | 2.17 | I' | TFA |
| 65 | Et | 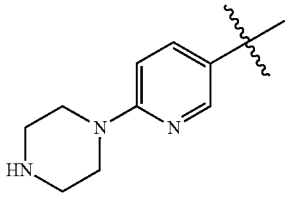 [SMILES: *c1ccc(N2CCNCC2)nc1] | H | A | 334.2 | 6.24 | A | HCl |
| 66 | CH2CF3 | 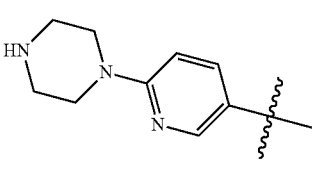 [SMILES: *c1ccc(N2CCNCC2)nc1] | H | A | 429.1 | 4.99 | A | HCl |
| 67 | Et | 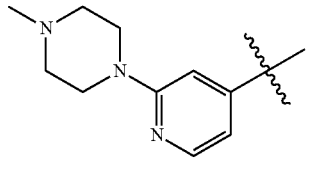 [SMILES: *c1ccnc(N2CCN(C)CC2)c1] | H | A | 375.3 | 2.05 | J | TFA |
| 68 | CH2CF3 | 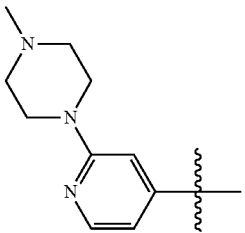 [SMILES: *c1ccnc(N2CCN(C)CC2)c1] | H | A | 443.2 | 6.51 | A | HCl |
| 69 | Et |  | H | A | 389 | 2.56 | J | TFA |

TABLE-continued
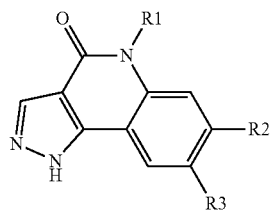
(I)
| Compound No. | R1 | R2 | R3 | Synthetic route | MH+ | RT (min) | LCMS method | Salt |
|---|---|---|---|---|---|---|---|---|
| 70 | CH2CF3 | 4-(piperazin-1-yl)pyridin-2-yl | H | A | 429.1 | 5.02 | A | / |
| 71 | Et | 4-(piperazin-1-yl)pyridin-2-yl | H | A | 375 | 2.45 | J | TFA |
| 72 | CH2CF3 | pyridin-3-yl | H | A | 359.2 | 5.05 | A | HCl |
| 73 | Et | 2-methylpyridin-3-yl | H | A | 305 | 1.99 | J | / |
| 74 | Et | 2-chloro-6-methylpyridin-3-yl | H | A | 339 | 2.84 | J | / |
| 75 | CH2CF3 | 3-chloro-6-methylpyridazin-4-yl | H | A | 393.1 | 1.06 | H | / |
| 76 | CH2CF3 | 2-chloropyridin-4-yl | H | A | 379.2 | 7.39 | A | HCl |
| 77 | CH2CF3 | 2-fluoropyridin-3-yl | H | A | 363.2 | 6.96 | A | HCl |

TABLE-continued
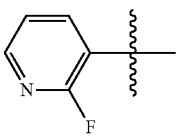 [SMILES: *c1cccnc1F]
(I)
| Compound No. | R1 | R2 | R3 | Synthetic route | MH+ | RT (min) | LCMS method | Salt |
|---|---|---|---|---|---|---|---|---|
| 78 | Et | 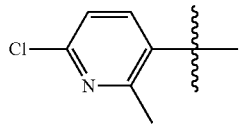 [SMILES: *c1ccc(Cl)nc1C] | H | A | 309.2 | 2.67 | J | / |
| 79 | CH2CF3 | 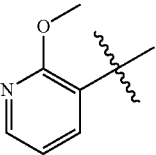 [SMILES: *c1cccnc1OC] | H | A | 393.1 | 1.09 | H | / |
| 80 | CH2CF3 | 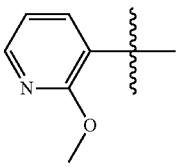 [SMILES: *c1cccnc1OC] | H | A | 375.2 | 7.34 | A | / |
| 81 | Et | 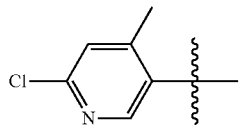 [SMILES: *c1cnc(Cl)cc1C] | H | A | 321.2 | 2.85 | J | / |
| 82 | CH2CF3 | 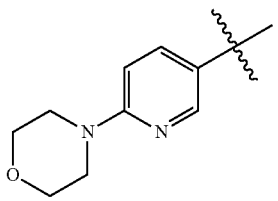 [SMILES: *c1ccc(N2CCOCC2)nc1] | H | A | 393.0 | 1.1 | H | / |
| 83 | CH2CF3 | 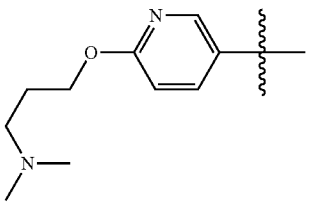 [SMILES: *c1ccc(OCCCN(C)C)nc1] | H | A | 430.0 | 6.28 | A | HCl |
| 84 | Et |  | H | A | 392 | 2.27 | J | TFA |

TABLE-continued (I)

| Compound No. | R1 | R2 | R3 | Synthetic route | MH+ | RT (min) | LCMS method | Salt |
|---|---|---|---|---|---|---|---|---|
| 85 | Et | quinolin-8-yl | H | A | 341.2 | 2.26 | I' | TFA |
| 86 | CH2CF3 | 6-chloropyridin-2-yl | H | A | 379.2 | 7.87 | A | HCl |
| 87 | Et | quinolin-6-yl | H | A | 341.1 | 2.3 | J | TFA |
| 88 | CH2CF3 | 6-chloropyridin-3-yl | H | A | 379.2 | 7.52 | A | HCl |
| 89 | CH2CF3 | 2-chloro-3-methylpyridin-5-yl | H | A | 393.1 | 1.11 | H | / |
| 90 | Et | 3-fluoropyridin-4-yl | H | A | 309.1 | 2.45 | J | / |
| 91 | Et | 3-chloropyridin-4-yl | H | A | 325.1 | 2.62 | J | / |
| 92 | Et | 2-fluoro-3-methylpyridin-5-yl | H | A | 323.2 | 2.82 | J | / |

TABLE-continued
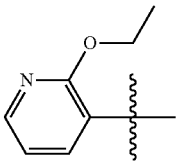 [SMILES: *c1cccnc1OCC]
(I)
| Compound No. | R1 | R2 | R3 | Synthetic route | MH+ | RT (min) | LCMS method | Salt |
|---|---|---|---|---|---|---|---|---|
| 93 | Et | 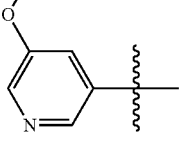 | H | A | 335.2 | 3.00 | J | / |
| 94 | Et | 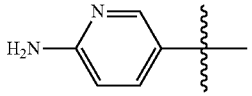 | H | A | 321.2 | 2.20 | J | / |
| 95 | Et | 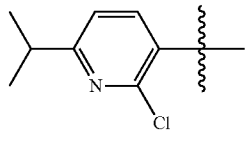 [SMILES: *c1ccc(C(C)C)nc1Cl] | H | A | 306.1 | 2.07 | J | TFA |
| 96 | Et | 3-Pyridinyl | H | A | 291.1 | 5.06 | A | HCl |
| 97 | CH2CF3 | 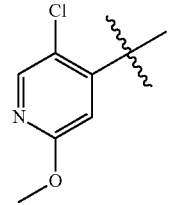 [SMILES: *c1cc(OC)ncc1Cl] | H | A | 421.1 | 1.17 | H | |
| 98 | CH2CF3 | 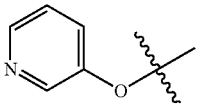 | H | A | 409.1 | 8.10 | A | |
| 99 (Ex. 3) | CH2CF3 | 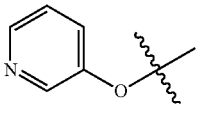 | H | A | 361.2 | 6.65 | A | |
| 100 | Et | 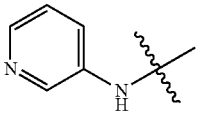 [SMILES: *Nc1cccnc1] | H | A | 307.2 | 5.72 | A | |
| 101 | CH2CF3 |  | H | A | 360.2 | 4.98 | A | |
| 102 (Ex. 4) | CH2CHF2 | 4-Pyridyl | H | B | 327.0 | 4.86 | A | |
| 103 | CH2cPr | 4-Pyridyl | H | B | 317.2 | 5.16 | A | |
| 104 | n-Pr | 4-Pyridyl | H | B | 305.0 | 5.04 | A | |

TABLE-continued (I)

| Compound No. | R1 | R2 | R3 | Synthetic route | MH+ | RT (min) | LCMS method | Salt |
|---|---|---|---|---|---|---|---|---|
| 105 | (2,2-difluorocyclopropyl)methyl | 4-Pyridyl | H | B | 353.2 | 4.63 | A | |
| 106 | CH2CH2F | 4-Pyridyl | H | B | 309.1 | 4.64 | A | |
| 107 (Ex. 5) | i-Pr | 4-Pyridyl | H | C | 305.1 | 4.98 | A | |
| 108 | c-Pr | 4-Pyridyl | H | C | 303.1 | 4.67 | A | |
| 109 (Ex. 6) | CH2CF3 | 2-Pyridyl | F | D | 363.1 | 1.69 | A | |
| 110 | CH2CF3 | 2-chloropyridin-3-yl | Me | D | 393.0 | 1.75 | D | |
| 111 (Ex. 7) | CH2CF3 | 2-chloropyridin-3-yl | H | E | 379.2 | 7.00 | A | |
| 112 | CH2CF3 | 2-(dimethylamino)phenyl | H | E | 387.2 | 7.37 | A | HCl |
| 113 | CH2CF3 | 2-(isopropoxycarbonyl)phenyl | H | E | 430.2 | 1.22 | H | / |
| 114 | CH2CF3 | 2-(cyclopropanecarboxamido)phenyl | H | E | 427.3 | 2.99 | J | / |

TABLE-continued
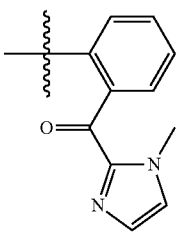 [SMILES: *c1ccccc1C(=O)c1nccn1C]
(I)
| Compound No. | R1 | R2 | R3 | Synthetic route | MH+ | RT (min) | LCMS method | Salt |
|---|---|---|---|---|---|---|---|---|
| 115 | CH2CF3 | 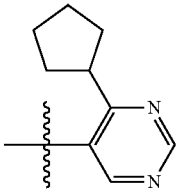 [SMILES: *c1cncnc1C1CCCC1] | H | E | 452.3 | 2.68 | J | / |
| 116 | CH2CF3 | 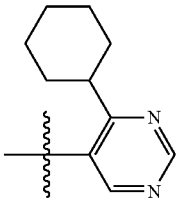 [SMILES: *c1cncnc1C1CCCCC1] | H | E | 414.2 | 3.17 | J | / |
| 117 | CH2CF3 | 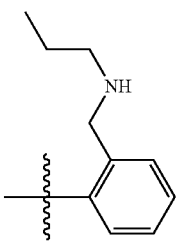 [SMILES: *c1ccccc1CNCCC] | H | E | 428.2 | 3.27 | J | / |
| 118 | CH2CF3 | 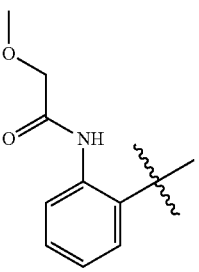 [SMILES: *c1ccccc1NC(=O)COC] | H | E | 415.3 | 2.50 | J | / |
| 119 | CH2CF3 |  | H | E | 431.3 | 2.93 | J | / |

TABLE-continued (I)

| Compound No. | R1 | R2 | R3 | Synthetic route | MH+ | RT (min) | LCMS method | Salt |
|---|---|---|---|---|---|---|---|---|
| 120 | CH2CF3 | 2-(isobutyrylamino)phenyl | H | E | 429.3 | 2.97 | J | / |
| 121 | CH2CF3 | 2-(propionylamino)-4-methylphenyl | H | E | 429.2 | 1.12 | H | / |
| 122 | CH2CF3 | 2-(isopropylcarbamoyl)phenyl | H | E | 429.3 | 2.89 | J | / |
| 123 | CH2CF3 | 2-(piperidin-4-yloxy)-5-methylphenyl | H | E | 457.3 | 1.01 | H | / |
| 124 | CH2CF3 | 2-((1,4-diazepan-1-yl)methyl)phenyl | H | E | 456.1 | 4.87 | A | HCl |

TABLE-continued
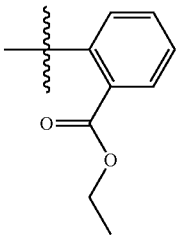 [SMILES: *c1ccccc1C(=O)OCC]
(I)
| Compound No. | R1 | R2 | R3 | Synthetic route | MH+ | RT (min) | LCMS method | Salt |
|---|---|---|---|---|---|---|---|---|
| 125 | CH2CF3 | 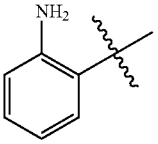 | H | E | 416.2 | 3.35 | J | / |
| 126 | CH2CF3 | 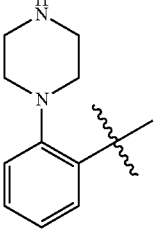 | H | E | 359.2 | 7.16 | A | HCl |
| 127 | CH2CF3 | 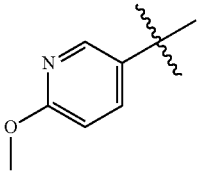 [SMILES: *c1ccc(OC)nc1] | H | E | 428.1 | 10.28 | B | HCl |
| 128 | CH2CF3 | 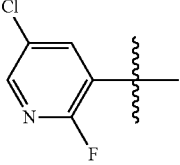 [SMILES: *c1cc(Cl)cnc1F] | H | E | 375 | 0.73 | H | / |
| 129 | CH2CF3 | 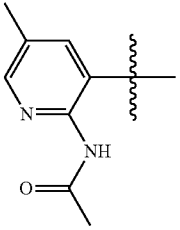 [SMILES: *c1cc(C)cnc1NC(C)=O] | H | E | 395.0 | 1.11 | H | / |
| 130 | CH2CF3 |  | H | E | 416.2 | 0.89 | H | / |

TABLE-continued (I)

| Compound No. | R1 | R2 | R3 | Synthetic route | MH+ | RT (min) | LCMS method | Salt |
|---|---|---|---|---|---|---|---|---|
| 131 | CH2CF3 | 2-(2-hydroxyethyl)phenyl | H | E | 388.1 | 1.04 | H | / |
| 132 | CH2CF3 | 2-amino-5-fluoropyridin-3-yl | H | E | 420.1 | 1.05 | H' | / |
| 133 | CH2CF3 | 2-(pyrrolidin-1-ylsulfonyl)phenyl | H | E | 475.1 | 1.1 | H | / |
| 134 | CH2CF3 | 2-(N-isopropylsulfamoyl)phenyl | H | E | 465.1 | 1.21 | H' | / |
| 135 | CH2CF3 | 2-fluoro-5-methylpyridin-3-yl | H | E | 377.1 | 1.06 | H | / |
| 136 | CH2CF3 | 2-(N,N-diethylsulfamoyl)phenyl | H | E | 479.1 | 1.12 | H | / |

TABLE-continued (I)

| Compound No. | R1 | R2 | R3 | Synthetic route | MH+ | RT (min) | LCMS method | Salt |
|---|---|---|---|---|---|---|---|---|
| 137 | CH2CF3 | 6-amino-4-methylpyridin-3-yl | H | E | 416.2 | 0.93 | H | / |
| 138 | CH2CF3 | 6-methoxy-2-methylpyridin-3-yl | H | E | 389.1 | 4.06 | I | / |
| 139 | CH2CF3 | 3-methyl-2-(1,2,4-triazol-4-yl)pyridin-5-yl | H | E | 426.1 | 1.01 | H' | / |
| 140 | CH2CF3 | 4-methyl-2-(1,2,4-triazol-4-yl)pyridin-5-yl | H | E | 426.1 | 1.02 | H' | / |
| 141 | CH2CF3 | 6-(morpholine-4-carbonyl)pyridin-3-yl | H | E | 458.1 | 1.03 | H' | / |
| 142 | CH2CF3 | 6-amino-2-methylpyridin-3-yl | H | E | 416.2 | 0.94 | H | / |
| 143 | CH2CF3 | 4-methylpyrimidin-5-yl | H | E | 374.1 | 0.98 | H | / |
| 144 | CH2CF3 | 2-(methoxycarbonylmethyl)phenyl | H | E | 414.0 | 1.1 | H | / |

TABLE-continued (I)

| Compound No. | R1 | R2 | R3 | Synthetic route | MH+ | RT (min) | LCMS method | Salt |
|---|---|---|---|---|---|---|---|---|
| 145 | CH2CF3 | 4-methoxypyridin-2-yl | H | E | 373.1 | 0.87 | H | / |
| 146 | CH2CF3 | 4-propylpyrimidin-5-yl | H | E | 388.1 | 1.13 | H' | / |
| 147 | CH2CF3 | 6-(propanamido)-2-methylpyridin-3-yl | H | E | 430.2 | 1.00 | H | / |
| 148 | CH2CF3 | 2-(oxazol-5-yl)phenyl | H | E | 411.2 | 1.09 | H | / |
| 149 | CH2CF3 | 4-(dimethylamino)-2-methoxypyrimidin-5-yl | H | E | 417.1 | 0.85 | H | / |
| 150 | CH2CF3 | 2-(5-ethyl-1,2,4-oxadiazol-3-yl)phenyl | H | E | 440.1 | 1.23 | H' | / |

TABLE-continued
(I)
| Compound No. | R1 | R2 | R3 | Synthetic route | MH+ | RT (min) | LCMS method | Salt |
|---|---|---|---|---|---|---|---|---|
| 151 | CH2CF3 | 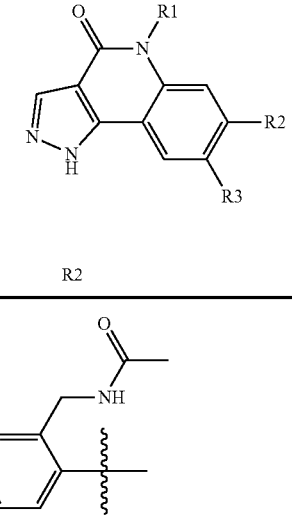 | H | E | 415.1 | 1.1 | H' | / |
| 152 | CH2CF3 | 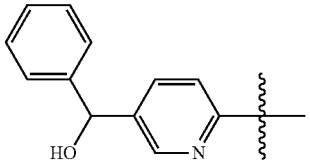 | H | E | 451.2 | 1.16 | H' | / |
| 153 | CH2CF3 | 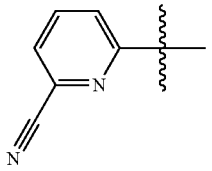 | H | E | 370.1 | 1.04 | H | / |
| 154 | CH2CF3 | 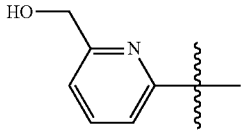 [SMILES: *c1cccc(CO)n1] | H | E | 375.1 | 0.93 | H | / |
| 155 | CH2CF3 | 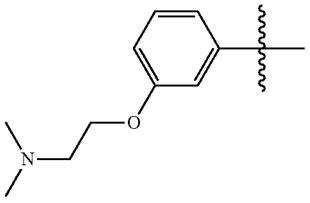 [SMILES: *c1cccc(OCCN(C)C)c1] | H | E | 431.2 | 0.97 | H' | / |
| 156 | CH2CF3 | 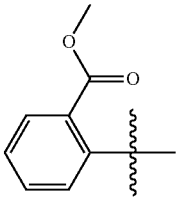 [SMILES: *c1ccccc1C(=O)OC] | H | E | 402.1 | 1.09 | H | / |
| 157 | CH2CF3 | 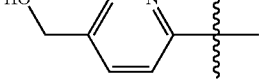 | H | E | 375.1 | 0.87 | H | / |

TABLE-continued
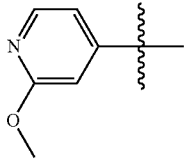 [SMILES: *c1ccnc(OC)c1]
(I)
| Compound No. | R1 | R2 | R3 | Synthetic route | MH+ | RT (min) | LCMS method | Salt |
|---|---|---|---|---|---|---|---|---|
| 158 | CH2CF3 | 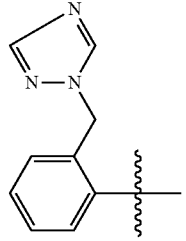 [SMILES: *c1ccccc1Cn1cncn1] | H | E | 363.1 | 1.03 | H | / |
| 159 | CH2CF3 | 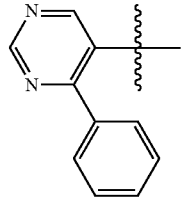 [SMILES: *c1cncnc1-c1ccccc1] | H | E | 425.2 | 1.01 | H | / |
| 160 | CH2CF3 | 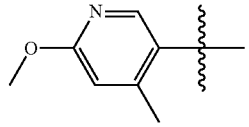 [SMILES: *c1cnc(OC)cc1C] | H | E | 420.1 | 1.04 | H | / |
| 161 | CH2CF3 | 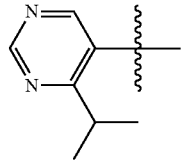 [SMILES: *c1cncnc1C(C)C] | H | E | 389.1 | 1.08 | H | / |
| 162 | CH2CF3 | 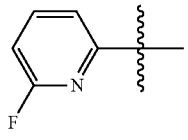 [SMILES: *c1cccc(F)n1] | H | E | 388.2 | 1.03 | H | / |
| 163 | CH2CF3 | 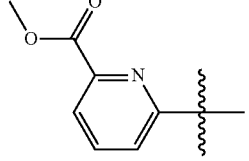 | H | E | 363.0 | 7.57 | A | / |
| 164 | CH2CF3 |  | H | E | 403.1 | 1.04 | H | / |

TABLE-continued (I)

| Compound No. | R1 | R2 | R3 | Synthetic route | MH+ | RT (min) | LCMS method | Salt |
|---|---|---|---|---|---|---|---|---|
| 165 | CH2CF3 | 5-fluoropyridin-2-yl | H | E | 363.1 | 7.42 | A | HCl |
| 166 | CH2CF3 | 2-(4-methylpiperazin-1-yl)pyridin-3-yl | H | E | 443.1 | 5.32 | A | HCl |
| 167 | CH2CF3 | 3-aminopyridin-4-yl | H | E | 360.2 | 4.59 | A | HCl |
| 168 | CH2CF3 | 2,6-dimethylpyridin-4-yl | H | E | 373.1 | 0.76 | H | / |
| 169 | CH2CF3 | 3-chloropyridin-2-yl | H | E | 379.2 | 7.16 | A | HCl |
| 170 | CH2CF3 | 3-(methoxycarbonyl)pyridin-2-yl | H | E | 403.2 | 6.49 | A | HCl |
| 171 | CH2CF3 | 6-methylpyridin-2-yl | H | E | 359.1 | 6.49 | A | HCl |

TABLE-continued (I)

| Compound No. | R1 | R2 | R3 | Synthetic route | MH+ | RT (min) | LCMS method | Salt |
|---|---|---|---|---|---|---|---|---|
| 172 | CH2CF3 | 3-(morpholin-4-yl)pyridin-2-yl | H | E | 430.3 | 2.39 | J | / |
| 173 | CH2CF3 | 2-(trifluoromethyl)pyridin-3-yl | H | E | 413.1 | 1.05 | H | / |
| 174 | CH2CF3 | 2-(cyclopropylamino)pyridin-3-yl | H | E | 400.3 | 2.32 | J | / |
| 175 | CH2CF3 | 3-(trifluoromethyl)pyridin-2-yl | H | E | 413.1 | 1.06 | H | / |
| 176 | CH2CF3 | 2-cyanopyridin-3-yl | H | E | 370.1 | 0.99 | H | / |
| 177 | CH2CF3 | 3-cyanopyridin-2-yl | H | E | 370.1 | 0.98 | H | / |
| 178 | CH2CF3 | methyl 2-pyridin-3-yl-carboxylate | H | E | 403.2 | 2.77 | J | / |

TABLE-continued
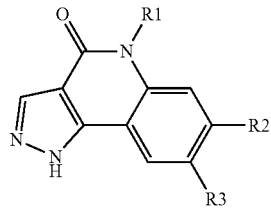
(I)
| Compound No. | R1 | R2 | R3 | Synthetic route | MH+ | RT (min) | LCMS method | Salt |
|---|---|---|---|---|---|---|---|---|
| 179 | CH2CF3 | 3-(2-propoxypyridin-3-yl) | H | E | 403.2 | 1.15 | H | / |
| 180 | CH2CF3 | 3-hydroxypyridin-2-yl | H | E | 361.3 | 2.44 | I | / |
| 181 | CH2CF3 | 2-(4-fluorophenylamino)pyridin-3-yl | H | E | 454.3 | 2.52 | J | / |
| 182 | CH2CF3 | 2-(methylamino)phenyl | H | E | 373.2 | 1.13 | H | / |
| 183 | CH2CF3 | 6-ethoxypyridazin-3-yl | H | E | 389.1 | 1.22 | H' | / |
| 184 | CH2CF3 | 2-isobutoxypyridin-3-yl | H | E | 403.2 | 1.16 | H | / |

TABLE-continued (I)

| Compound No. | R1 | R2 | R3 | Synthetic route | MH+ | RT (min) | LCMS method | Salt |
|---|---|---|---|---|---|---|---|---|
| 185 | CH2CF3 | 5-chloro-2-methoxypyridin-3-yl | H | E | 409.0 | 1.16 | H | / |
| 186 | CH2CF3 | 2-methylpyridin-4-yl | H | E | 359.1 | 0.77 | H | / |
| 187 | CH2CF3 | 4-methylpyridin-2-yl | H | E | 359.1 | 0.97 | H | / |
| 188 | CH2CF3 | 6-morpholinopyridin-2-yl | H | E | 430.2 | 1.09 | H | / |
| 189 | CH2CF3 | 4-(methylamino)phenyl | H | E | 373.1 | 1.03 | H | / |
| 190 | CH2CF3 | 6-(trifluoromethyl)pyridin-3-yl | H | E | 413.1 | 1.12 | H | / |
| 191 | CH2CF3 | 6-methoxypyridin-2-yl | H | E | 375.1 | 1.12 | H | / |
| 192 | CH2CF3 | 4-(2H-tetrazol-5-yl)phenyl | H | E | 412.2 | 1.51 | D | HCl |

TABLE-continued
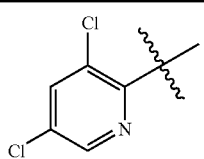
(I)
| Compound No. | R1 | R2 | R3 | Synthetic route | MH+ | RT (min) | LCMS method | Salt |
|---|---|---|---|---|---|---|---|---|
| 193 | CH2CF3 | 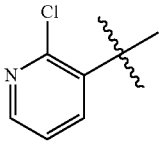 | H | E | 413.0 | 8.19 | A | HCl |
| 194 (Ex. 8) | CH2CF3 | 2-Pyridyl | Cl | F | 379.2 | 6.91 | A | HCl |
| 195 (Ex. 9) | CH2CF3 | 2-Pyridyl | Br | F | 425.2 | 7.00 | A | HCl |
| 196 | CH2CF3 | 4-Pyridyl | Cl | F | 379.0 | 5.55 | A | HCl |
| 197 | CH2CF3 | 4-Pyridyl | Br | F | 423.0 | 6.05 | A | HCl |
| 198 | Et | 4-Pyridyl | Cl | F | 325.1 | 2.12 | J | HCl |
| 199 | CH2CF3 | 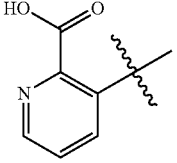 | Cl | F | 413.0 | 7.54 | A | / |
| 200 | CH2CF3 | 2-Pyridyl | Me | D | 359.2 | 6.29 | A | HCl |
| 201 (Ex. 10) | CH2CF3 | 4-Pyridyl | CN | G | 369.9 | 5.52 | C | HCl |
| 202 (Ex. 11) | CH2CF3 | 4-Pyridyl | CO2H | H | 389.0 | 4.37 | A | HCl |
| 203 (Ex. 12) | CH2CF3 | 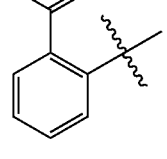 | H | I | 389 | 1.58 | E | HCl |
| 204 | CH2CF3 | 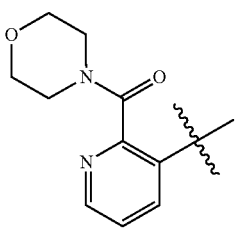 [SMILES: *c1cccnc1C(=O)N1CCOCC1] | H | I | 388.0 | 7.05 | A | / |
| 205 (Ex. 13) | CH2CF3 | 4-Pyridyl | CONH2 | J | 388.0 | 5.78 | C | / |
| 206 (Ex. 14) | CH2CF3 |  | H | J | 458.1 | 5.95 | A | HCl |

TABLE-continued (I)

| Compound No. | R1 | R2 | R3 | Synthetic route | MH+ | RT (min) | LCMS method | Salt |
|---|---|---|---|---|---|---|---|---|
| 207 | CH2CF3 | (2-(N,N-dimethylamino)ethyl-N-methyl-benzamide) | H | J | 472.2 | 5.46 | A | HCl |
| 208 | CH2CF3 | (2-(N,N-dimethylamino)ethyl-N-ethyl-benzamide) | H | J | 486.1 | 5.62 | A | HCl |
| 209 | CH2CF3 | (4-methyl-1,4-diazepan-1-yl)carbonyl-benzene | H | J | 484.2 | 9.17 | A | HCl |
| 210 | CH2CF3 | (4-methylpiperazin-1-yl)carbonyl-benzene | H | J | 470.1 | 5.31 | A | / |
| 211 | CH2CF3 | 3-(carbamoyl)phenyl-aminocarbonyl-benzene | H | J | 506.0 | 6.79 | A | HCl |

TABLE-continued
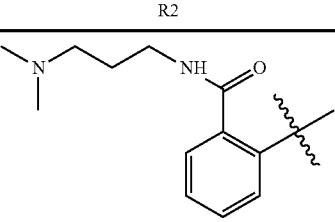
(I)
| Compound No. | R1 | R2 | R3 | Synthetic route | MH+ | RT (min) | LCMS method | Salt |
|---|---|---|---|---|---|---|---|---|
| 212 | CH2CF3 | 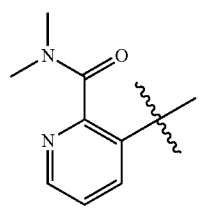 [SMILES: *c1cccnc1C(=O)N(C)C] | H | J | 472.2 | 5.18 | A | HCl |
| 213 | CH2CF3 | 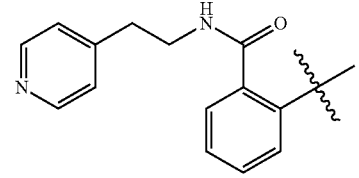 [SMILES: *c1ccccc1C(=O)NCCc1ccncc1] | H | J | 416.2 | 5.93 | A | HCl |
| 214 | CH2CF3 | 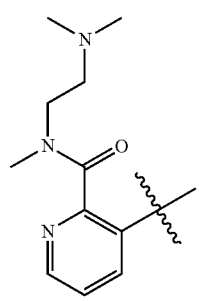 [SMILES: *c1cccnc1C(=O)N(C)CCN(C)C] | H | J | 492.2 | 5.26 | A | HCl |
| 215 | CH2CF3 | 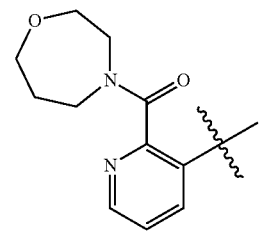 [SMILES: *c1cccnc1C(=O)N1CCCOCC1] | H | J | 473.1 | 4.98 | A | HCl |
| 216 | CH2CF3 | 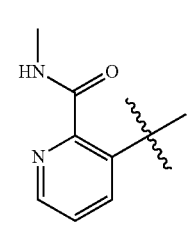 | H | J | 472.0 | 6.11 | A | HCl |
| 217 | CH2CF3 | | H | J | 402.2 | 5.84 | A | HCl |

TABLE-continued
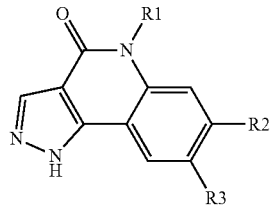
(I)
| Compound No. | R1 | R2 | R3 | Synthetic route | MH+ | RT (min) | LCMS method | Salt |
|---|---|---|---|---|---|---|---|---|
| 218 | CH2CF3 | (3-pyridylmethylamide benzamide) | H | J | 478.2 | 5.62 | A | HCl |
| 219 | CH2CF3 | (N-ethyl-N-(4-pyridylmethyl) benzamide) | H | J | 506.2 | 7.41 | C | HCl |
| 220 | CH2CF3 | (2-carbamoyl pyridin-3-yl) | H | J | 388.0 | 5.81 | A | HCl |
| 221 | CH2CF3 | (N-ethyl-N-(2-dimethylaminoethyl) pyridine-3-carboxamide) | H | J | 487.0 | 5.07 | A | HCl |
| 222 | CH2CF3 | (2,6-dimethylmorpholine pyridine-2-carbonyl) | H | J | 486.1 | 6.38 | A | HCl |

TABLE-continued
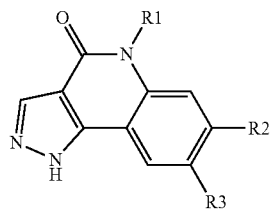
(I)
| Compound No. | R1 | R2 | R3 | Synthetic route | MH+ | RT (min) | LCMS method | Salt |
|---|---|---|---|---|---|---|---|---|
| 223 (Ex. 15) | CH2CF3 | | H | K | 402.2 | 5.56 | A | HCl |
| 224 | CH2CF3 | ![](dimethylamino-propanamido-phenyl) | H | K | 458.2 | 8.82 | A | HCl |
| 225 | CH2CF3 | ![](dimethylamino-butanamido-phenyl) | H | K | 472.2 | 5.36 | A | HCl |
| 226 | CH2CF3 | | H | K | 402.0 | 5.3 | A | HCl |
| 227 | CH2CF3 | ![](cyclopropanecarboxamido-pyridyl) | H | K | 428.1 | 5.87 | A | HCl |

TABLE-continued
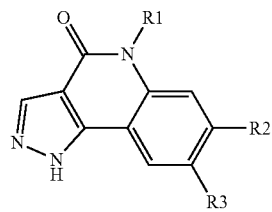
(I)
| Compound No. | R1 | R2 | R3 | Synthetic route | MH+ | RT (min) | LCMS method | Salt |
|---|---|---|---|---|---|---|---|---|
| 228 | CH2CF3 | -C(O)NH-pyridinyl) | H | K | 508.2 | 6.37 | A | / |
| 229 | CH2CF3 | -C(O)NH-pyridinyl) | H | K | 492.1 | 11.48 | B | / |
| 230 | CH2CF3 | NH-pyridinyl) | H | K | 512.3 | 11.86 | B | HCl |
| 231 | CH2CF3 | NH-pyridinyl) | H | K | 546.0 | 13.00 | B | HCl |
| 232 (Ex. 16) | CH2CF3 | | H | L | 437.1 | 13.31 | B | / |

TABLE-continued (I)

| Compound No. | R1 | R2 | R3 | Synthetic route | MH+ | RT (min) | LCMS method | Salt |
|---|---|---|---|---|---|---|---|---|
| 233 | CH2CF3 | 2-(dimethylamino)ethylsulfonamido-phenyl | H | L | 494.0 | 7.27 | A | HCl |
| 234 | CH2CF3 | benzylsulfonamido-phenyl | H | L | 513.0 | 8.10 | A | / |
| 235 | CH2CF3 | 3-chlorophenylsulfonamido-phenyl | H | L | 533.0 | 15.72 | B | / |
| 236 | CH2CF3 | methylsulfonamido-pyridinyl | H | L | 438.0 | 10.06 | B | HCl |

TABLE-continued
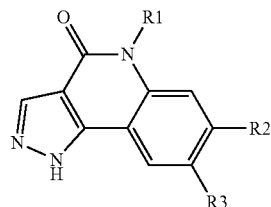
(I)
| Compound No. | R1 | R2 | R3 | Synthetic route | MH+ | RT (min) | LCMS method | Salt |
|---|---|---|---|---|---|---|---|---|
| 237 | CH2CF3 | (benzylsulfonamido-pyridinyl) | H | L | 514.0 | 12.64 | B | HCl |
| 238 | CH2CF3 | (3-chlorophenylsulfonamido-pyridinyl) | H | L | 534.0 | 12.51 | B | HCl |
| 239 | CH2CF3 | (5-acetamidomethyl-2-methoxyphenylsulfonamido-pyridinyl) | H | L | 601 | 6.02 | A | HCl |
| 240 | CH2CF3 | (2-phenoxyphenylsulfonamido-pyridinyl) | H | L | 592.2 | 7.64 | A | HCl |

TABLE-continued
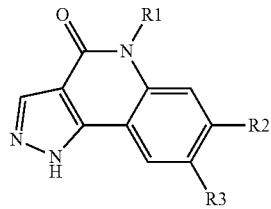
(I)
| Compound No. | R1 | R2 | R3 | Synthetic route | MH+ | RT (min) | LCMS method | Salt |
|---|---|---|---|---|---|---|---|---|
| 241 (Ex. 17) | CH2CF3 | ![acetyl-N-methyl pyridine] | H | M | 416.1 | 6.15 | A | HCl |
| 242 | CH2CF3 | ![cyclopropyl carbonyl-N-methyl pyridine] | H | M | 442.2 | 6.48 | A | HCl |
| 243 | CH2CF3 | ![HN-methyl pyridine] | H | M then I | 374.2 | 4.81 | A | HCl |
| 244 (Ex. 18) | CH2CF3 | ![diazepanyl pyridine] | H | N | 443.2 | 5.13 | A | HCl |
| 245 (Ex. 19) | CH2CF3 | ![piperidinyl pyridine] | H | N | 428.2 | 6.13 | A | HCl |
| 246 | CH2CF3 | ![hydroxypyrrolidinyl pyridine] | H | N | 430.2 | 4.86 | A | HCl |

TABLE-continued
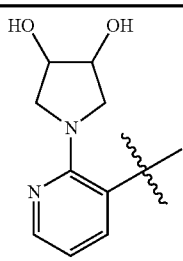
(I)
| Compound No. | R1 | R2 | R3 | Synthetic route | MH+ | RT (min) | LCMS method | Salt |
|---|---|---|---|---|---|---|---|---|
| 247 | CH2CF3 |  | H | N | 446.0 | 0.90 | D | HCl |
| 248 | CH2CF3 | 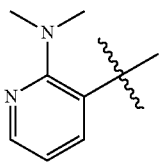 [SMILES: *c1cccnc1N(C)C] | H | N | 388.2 | 5.20 | A | HCl |
| 249 | CH2CF3 |  | H | N | 402.2 | 5.53 | A | HCl |
| 250 | CH2CF3 | 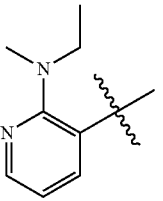 [SMILES: *c1cccnc1N(C)CC] | H | N | 418.0 | 5.09 | A | HCl |
| 251 | CH2CF3 |  | H | N | 414.1 | 5.18 | A | HCl |
| 252 | CH2CF3 | 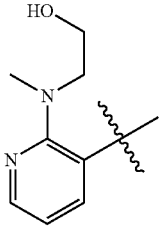 [SMILES: *c1cccnc1N(C)CCO] | H | N | 444.2 | 5.72 | A | / |

TABLE-continued (I)

| Compound No. | R1 | R2 | R3 | Synthetic route | MH+ | RT (min) | LCMS method | Salt |
|---|---|---|---|---|---|---|---|---|
| 253 | CH2CF3 | 3-oxopiperazin-1-yl-pyridin-2-yl | H | N | 443.2 | 6.14 | A | HCl |
| 254 | CH2CF3 | azetidin-1-yl-pyridin-2-yl | H | N | 400.2 | 4.79 | A | HCl |
| 255 | CH2CF3 | N-(2-methoxyethyl)-N-methylamino-pyridin-2-yl | H | N | 432.2 | 5.51 | A | HCl |
| 256 | CH2CF3 | 4-acetylpiperazin-1-yl-pyridin-2-yl | H | N | 471.1 | 6.20 | A | HCl |
| 257 | CH2CF3 | N,N-diethylamino-pyridin-2-yl | H | N | 416.1 | 6.04 | A | HCl |

TABLE-continued (I)

| Compound No. | R1 | R2 | R3 | Synthetic route | MH+ | RT (min) | LCMS method | Salt |
|---|---|---|---|---|---|---|---|---|
| 258 | CH2CF3 | (cyclobutyl-NH-pyridin-2-yl) | H | N | 414.2 | 5.41 | A | HCl |
| 259 | CH2CF3 | (2,6-dimethylmorpholin-4-yl-pyridin-2-yl) | H | N | 458.2 | 6.80 | A | HCl |
| 260 | CH2CF3 | (4-cyclopropylpiperazin-1-yl-pyridin-2-yl) | H | N | 469.2 | 5.29 | A | / |
| 261 | CH2CF3 | (cyclohexyl-NH-pyridin-2-yl) | H | N | 442.2 | 5.87 | A | HCl |
| 262 | CH2CF3 | (N-isopropyl-N-methylamino-pyridin-2-yl) | H | N | 416.2 | 5.99 | A | HCl |
| 263 | CH2CF3 | (cyclopentyl-NH-pyridin-2-yl) | H | N | 428.2 | 5.65 | A | HCl |

TABLE-continued
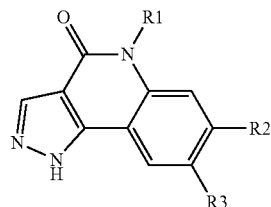
(I)
| Compound No. | R1 | R2 | R3 | Synthetic route | MH+ | RT (min) | LCMS method | Salt |
|---|---|---|---|---|---|---|---|---|
| 264 | CH2CF3 | (6-pyrrolidin-1-yl-pyridin-2-yl) | H | N | 414.2 | 7.00 | A | HCl |
| 265 | CH2CF3 | (6-(2,6-dimethylmorpholin-4-yl)pyridin-2-yl) | H | N | 458.1 | 8.50 | A | HCl |
| 266 | CH2CF3 | (2-(cyclohexyl(methyl)amino)pyridin-3-yl) | H | N | 456.1 | 6.35 | A | HCl |
| 267 (Ex. 20) | CH2CF3 | (2-(4-cyclopropylpiperazin-1-yl)pyridin-3-yl) | H | N | 469.2 | 5.32 | A | HCl |
| 268 | CH2CF3 | (3-(4-cyclopropylpiperazin-1-yl)phenyl) | H | N | 468.1 | 5.71 | A | HCl |

TABLE-continued
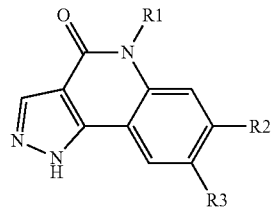
(I)
| Compound No. | R1 | R2 | R3 | Synthetic route | MH+ | RT (min) | LCMS method | Salt |
|---|---|---|---|---|---|---|---|---|
| 269 | CH2CF3 | ![acetyl-diazepane-pyridine] | H | K | 485.3 | 7.12 | C | HCl |
| 270 (Ex. 21) | CH2CF3 | ![methyl-diazepane-pyridine] | H | O | 457.2 | 5.21 | A | HCl |
| 271 (Ex. 22) | CH2CF3 | ![cyclopropyl-diazepane-pyridine] | H | O | 483.2 | 5.36 | A | HCl |
| 272 (Ex. 23) | CH2CF3 | ![fluoropyrrolidine-pyridine] | H | P | 432.1 | 5.50 | A | / |

TABLE-continued

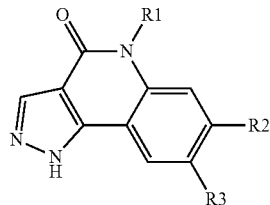

(I)

| Compound No. | R1 | R2 | R3 | Synthetic route | MH+ | RT (min) | LCMS method | Salt |
|---|---|---|---|---|---|---|---|---|
| 273 | CH2CF3 | (4-fluoropiperidin-1-yl)pyridin-3-yl | H | P | 446.1 | 6.67 | A | HCl |
| 274 (Ex. 24) | CH2CF3 | 2-hydroxypyridin-3-yl | H | Q | 361.0 | 5.91 | A | / |
| 275 (Ex. 25) | CH2CF3 | pyridine N-oxide (2-yl) | H | R | 361.2 | 5.53 | A | HCl |
| 276 | CH2CF3 | pyridine N-oxide (4-yl) | H | R | 361.0 | 5.47 | A | HCl |

The compounds according to the invention underwent biochemical studies in order to determine their capacity to inhibit the enzyme methionine-aminopeptidase2 (enzymatic test on isolated enzyme). The inhibitory activity of the compounds was than validated on a cell test (test of in vitro proliferation of HUVEC cells induced with FGF-2 (fibroblast growth factor 2)).

MetAP2 Enzymatic Screening Test

For the enzymatic test, human MetAP2 protein was obtained from a culture supernatant of insect cells (sf9) infected with MetAP2 recombinant baculovirus.

Before performing the experiment, dialysis of the MetAP2 supernatant is performed over 24 hours at 4° C. in a buffer (10 mM Hepes, 100 mM KCl, 10% glycerol, pH 7.4) in the presence of EDTA (1 mM) over the first 12 hours.

The dialysis supernatant is recovered and manganese, used as cofactor, is added to a final concentration of 300 µM.

The enzymatic test is a test in two steps.

In a first step, it consists in placing in contact the compound according to the invention, the dialysed MetAP2 protein and the substrate (Met-Pro-Arg-pNa peptide synthesized by Neosystem), the N-terminal methionine of which can be cleaved with MetAP2, and which bears at the C-terminal end a para-nitroaniline (pNa) chromophore, which can itself be released by another peptidase only when the N-terminal methionine has been cleaved beforehand.

Consequently, the second step consists in reacting the peptides cleaved in the preceding step with a second peptidase in order to release the chromophore. The peptidase used in this second step is cathepsin, which comes from the TagZyme "DAPase" kit (Quiagen, 34366).

The MetAP2 activity is proportional to the amount of para-nitroaniline released, which is measured by absorbance at 405 nm.

The IC50 values for the compounds of the invention are generally less than 550 nM, more particularly between 1 and 550 nM and even more particularly between 1 and 100 nM and/or show inhibition at 100 nM of greater than or equal to 34%, as indicated in the table below:

| Compound No. | hMETAP2 IC50 (M) | % inhibition hMETAP2 at 100 nM |
| --- | --- | --- |
| 1 | 7.53E−09 | |
| 2 | 7.06E−09 | |
| 3 | | 34 |
| 4 | 1.55E−07 | 65 |
| 5 | 2.20E−07 | 47 |
| 6 | 2.19E−08 | 73 |
| 7 | 2.00E−07 | |
| 8 | 1.80E−07 | 73 |
| 9 | | 78 |
| 10 | | 77 |
| 11 | | 76 |
| 12 | 1.21E−08 | |
| 13 | | 75 |
| 14 | 8.30E−08 | |
| 15 | | 74 |
| 16 | 1.74E−08 | |
| 17 | 1.70E−07 | 64 |
| 18 | | 72 |
| 19 | 3.94E−09 | |
| 20 | | 70 |
| 21 | | 70 |
| 22 | | 69 |
| 23 | 1.51E−07 | |
| 24 | | 67 |
| 25 | 4.11E−08 | |
| 26 | 1.17E−07 | 59 |
| 27 | | 67 |
| 28 | | 67 |
| 29 | | 67 |
| 30 | 2.13E−09 | |
| 31 | | 64 |
| 32 | 3.94E−08 | |
| 33 | | 62 |
| 34 | | 62 |
| 35 | | 62 |
| 36 | | 61 |
| 37 | | 60 |
| 38 | | 60 |
| 39 | | 60 |
| 40 | | 40 |
| 41 | | 40 |
| 42 | 1.69E−08 | 71 |
| 43 | 4.45E−08 | 70 |
| 44 | 1.43E−07 | 61 |
| 45 | 2.86E−07 | 64 |
| 46 | 9.03E−08 | 64 |
| 47 | 8.44E−08 | 68 |
| 48 | 1.02E−07 | 68 |
| 49 | | 45 |
| 50 | 3.32E−07 | 66 |
| 51 | 3.54E−07 | 63 |
| 52 | 3.51E−07 | 55 |
| 53 | | 43 |
| 54 | 2.39E−08 | 74 |
| 55 | | 40 |
| 56 | 1.57E−07 | 69 |
| 57 | | 38 |
| 58 | 1.81E−07 | 71 |
| 59 | 4.64E−08 | 75 |
| 60 | 5.96E−08 | 71 |
| 61 | 1.35E−07 | 68 |
| 62 | 2.00E−08 | 77 |
| 63 | 5.49E−08 | 69 |
| 64 | 2.60E−08 | 61 |
| 65 | 3.20E−07 | 71 |
| 66 | 3.06E−09 | |
| 67 | 2.29E−08 | 75 |
| 68 | 4.12E−09 | |
| 69 | 2.41E−08 | 76 |
| 70 | 5.62E−09 | |
| 71 | 5.25E−08 | 73 |
| 72 | 7.38E−09 | |
| 73 | 8.43E−08 | 66 |
| 74 | 5.87E−08 | 60 |
| 75 | 1.23E−08 | |
| 76 | 1.49E−08 | |
| 77 | 1.92E−08 | |
| 78 | 8.35E−08 | 57 |
| 79 | 2.14E−08 | |
| 80 | 2.27E−08 | |
| 81 | 9.99E−08 | 59 |
| 82 | 2.51E−08 | |
| 83 | 2.89E−08 | |
| 84 | 3.07E−08 | 69 |
| 85 | 3.57E−08 | 77 |
| 86 | 4.17E−08 | |
| 87 | 5.04E−08 | 70 |
| 88 | 5.10E−08 | |
| 89 | 6.69E−08 | |
| 90 | 8.70E−08 | 59 |
| 91 | 8.86E−08 | 65 |
| 92 | 1.06E−07 | 70 |
| 93 | 2.40E−07 | 64 |
| 94 | 1.14E−07 | 57 |
| 95 | 1.42E−07 | 63 |
| 96 | 1.88E−07 | 64 |
| 97 | 5.50E−07 | |
| 98 | | 36 |
| 99 | 6.19E−08 | 73 |
| 100 | 3.17E−07 | 55 |
| 101 | 1.42E−07 | 76 |
| 102 | 1.09E−07 | 69 |
| 103 | 1.33E−07 | 72 |
| 104 | 1.58E−07 | 71 |
| 105 | 2.06E−07 | 69 |
| 106 | 3.90E−07 | 65 |
| 107 | 2.74E−07 | 71 |
| 108 | 8.31E−08 | 73 |
| 109 | 7.10E−09 | |
| 110 | 1.11E−08 | |
| 111 | 7.42E−09 | |
| 112 | 8.70E−08 | |
| 113 | 2.07E−07 | 74 |
| 114 | 2.25E−08 | 76 |
| 115 | 4.01E−08 | 42 |
| 116 | 2.39E−08 | 75 |
| 117 | 3.50E−08 | 77 |
| 118 | 2.03E−08 | 35 |
| 119 | 1.18E−08 | 78 |
| 120 | 2.54E−08 | 75 |
| 121 | 4.29E−09 | 78 |
| 122 | 5.68E−08 | 75 |
| 123 | 3.13E−08 | 77 |
| 124 | 9.22E−09 | 73 |
| 125 | 3.04E−08 | 75 |
| 126 | 1.04E−08 | 72 |
| 127 | 3.05E−08 | 79 |
| 128 | | 41 |
| 129 | | 36 |
| 130 | | 48 |
| 131 | | 46 |
| 132 | | 46 |
| 133 | | 45 |
| 134 | | 45 |
| 135 | | 45 |
| 136 | | 45 |
| 137 | | 45 |
| 138 | | 44 |
| 139 | | 44 |
| 140 | | 44 |
| 141 | | 44 |
| 142 | | 44 |
| 143 | | 43 |
| 144 | | 43 |
| 145 | | 42 |
| 146 | | 42 |
| 147 | | 42 |
| 148 | | 42 |
| 149 | | 42 |
| 150 | | 42 |
| 151 | | 41 |
| 152 | | 41 |

| Compound No. | hMETAP2 IC50 (M) | % inhibition hMETAP2 at 100 nM |
|---|---|---|
| 153 | | 41 |
| 154 | | 41 |
| 155 | | 41 |
| 156 | | 41 |
| 157 | | 41 |
| 158 | | 40 |
| 159 | | 40 |
| 160 | | 40 |
| 161 | | 39 |
| 162 | | 38 |
| 163 | | 38 |
| 164 | | 37 |
| 165 | | 37 |
| 166 | 7.24E−09 | |
| 167 | 7.64E−09 | 78 |
| 168 | 8.81E−09 | |
| 169 | 8.83E−09 | |
| 170 | 9.36E−09 | |
| 171 | 1.73E−08 | |
| 172 | 2.40E−08 | 41 |
| 173 | 2.68E−08 | |
| 174 | 3.33E−08 | 73 |
| 175 | 4.28E−08 | |
| 176 | 5.19E−08 | |
| 177 | 6.12E−08 | |
| 178 | 6.22E−08 | 71 |
| 179 | 6.38E−08 | |
| 180 | 7.46E−08 | |
| 181 | 1.02E−07 | 75 |
| 182 | 1.13E−07 | |
| 183 | 1.13E−07 | |
| 184 | 2.98E−07 | |
| 185 | 4.25E−07 | |
| 186 | | 43 |
| 187 | | 40 |
| 188 | 3.62E−07 | |
| 189 | 6.06E−08 | |
| 190 | 2.94E−07 | |
| 191 | 3.73E−07 | |
| 192 | 2.63E−08 | |
| 193 | 7.20E−08 | |
| 194 | 8.22E−09 | |
| 195 | 2.24E−08 | |
| 196 | 7.77E−09 | 64 |
| 197 | 1.56E−08 | 68 |
| 198 | 2.40E−07 | 68 |
| 199 | 4.90E−09 | |
| 200 | 2.33E−08 | |
| 201 | 1.79E−08 | 72 |
| 202 | 4.34E−07 | 58 |
| 203 | 1.64E−07 | |
| 204 | 2.23E−07 | |
| 205 | 1.98E−07 | 66 |
| 206 | 1.41E−08 | |
| 207 | 9.53E−09 | |
| 208 | 3.64E−08 | |
| 209 | 8.98E−09 | |
| 210 | 1.38E−07 | |
| 211 | 2.67E−07 | |
| 212 | 1.83E−08 | 73 |
| 213 | 1.25E−08 | |
| 214 | 1.29E−08 | 70 |
| 215 | 1.45E−08 | |
| 216 | 1.47E−08 | |
| 217 | 2.17E−08 | |
| 218 | 2.78E−08 | 70 |
| 219 | 2.96E−08 | 75 |
| 220 | 3.62E−08 | |
| 221 | 7.14E−08 | |
| 222 | 4.26E−07 | |
| 223 | 9.01E−09 | |
| 224 | 4.06E−08 | |
| 225 | 3.29E−08 | |
| 226 | 4.68E−09 | |
| 227 | 1.53E−08 | |
| 228 | 5.51E−08 | 62 |
| 229 | 5.64E−08 | 71 |
| 230 | 2.06E−07 | 70 |
| 231 | 2.81E−07 | 67 |
| 232 | 5.33E−09 | 64 |
| 233 | 4.99E−09 | |
| 234 | 8.55E−08 | 64 |
| 235 | 1.60E−07 | 64 |
| 236 | 9.66E−09 | 64 |
| 237 | 1.02E−08 | 67 |
| 238 | 7.63E−08 | 60 |
| 239 | 8.50E−08 | 72 |
| 240 | 3.07E−07 | 67 |
| 241 | 2.42E−08 | |
| 242 | 7.52E−08 | |
| 243 | 1.06E−08 | |
| 244 | 6.08E−09 | |
| 245 | 8.28E−08 | |
| 246 | 1.46E−09 | |
| 247 | 6.41E−09 | |
| 248 | 3.87E−09 | |
| 249 | 4.19E−09 | |
| 250 | 4.41E−09 | |
| 251 | 5.34E−09 | |
| 252 | 8.35E−09 | |
| 253 | 9.44E−09 | |
| 254 | 1.30E−08 | |
| 255 | 2.40E−08 | |
| 256 | 2.80E−08 | |
| 257 | 3.11E−08 | |
| 258 | 3.45E−08 | |
| 259 | 3.45E−08 | |
| 260 | 7.09E−08 | |
| 261 | 8.57E−08 | |
| 262 | 8.60E−08 | |
| 263 | 1.06E−07 | |
| 264 | 1.20E−07 | |
| 265 | 2.68E−07 | |
| 266 | 3.82E−07 | |
| 267 | 4.30E−08 | |
| 268 | 1.14E−07 | |
| 269 | 1.69E−08 | |
| 270 | 6.00E−09 | |
| 271 | 2.43E−08 | |
| 272 | 3.40E−08 | |
| 273 | 3.45E−09 | |
| 274 | 1.13E−08 | |
| 275 | 1.80E−08 | |
| 276 | 6.57E−08 | 73 |

In order to determine the selectivity of the compounds of the invention towards the protein MetAP1, an enzymatic test on the isolated enzyme is performed. The MetAP1 recombinant protein was produced in *Escherichia coli*.

The MetAP1 enzymatic test is based on the same principle as the MetAP2 test.

The MetAP1 activity is proportional to the amount of para-nitroaniline released, which is measured by absorbance at 405 nm.

The compounds of the invention show no activity at 10 µM.

Test of In Vitro Proliferation of HUVEC Cells Induced with Fibroblast Growth Actor 2 (FGF-2).

It has been demonstrated that an angiogenesis inhibitor, fumagillin, is capable of selectively inhibiting the proliferation of endothelial cells (Wang J. et al., *J. Cell. Bloch.* 2000, vol. 77, 465-473). Consequently, the compounds of the invention that show good activity in the MetAP2 enzymatic test were evaluated in a test of in vitro proliferation of HUVEC cells induced with FGF-2.

Human venous endothelial cells HUVEC (promocell, C-12200) are seeded at a rate of 5000 cells per well in 96-well plates (Biocoat collagen I cellware, Becton Dickinson 354650) in 200 µl of EBM medium (Clonetics C3121) with 2% FCS (foetal calf serum) and hEGF (epidermal growth factor human) at 10 µg/ml and then incubated for 24 hours at 37° C. in the presence of $CO_2$. The medium is then aspirated and replaced with 200 µl of deprivation medium RPMI1640 (Invitrogen, 31872-025) supplemented with 0.5% FCS, 2 mM glutamine, 2 mM sodium pyruvate 1× (Invitrogen, 11360-039) and NEAA (non-essential amino acids) 1× (Invitrogen, 11140-035). The cells are then placed in contact with the compound according to the invention and FGF-2 in a proportion of 1 ng/ml (R&D System, 133-FB-025). After incubation for 48 hours, the medium is aspirated and replaced with the deprivation medium RPMI1640 mentioned previously. A second stimulation is then performed. The cells are again incubated at 37° C. in the presence of $CO_2$. After incubation for 72 hours, the medium is again aspirated and 100 µl of Cell Titer-GLO™ Luminescent Cell Viability Assay (Promega, G7571) are added over 10 minutes. The amount of ATP present in the cells, measured using a luminometer, is proportional to the number cells per well corresponding to the cell proliferation.

The IC50 values for the compounds of the invention are generally less than 900 nM, more particularly between 150 and 900 nM and even more particularly between 100 and 350 nM, as indicated, for example, for the compounds below:

| Compound No. | HUVEC Proliferation IC50 (M) |
|---|---|
| 1 | 220 nM |
| 2 | 480 nM |
| 3 | 660 nM |
| 6 | 340 nM |
| 7 | 695 nM |
| 19 | 415 nM |
| 67 | 335 nM |
| 68 | 440 nM |
| 69 | 130 nM |
| 72 | 480 nM |
| 74 | 180 nM |
| 75 | 125 nM |
| 76 | 305 nM |
| 77 | 235 nM |
| 79 | 510 nM |
| 83 | 370 nM |
| 86 | 939 nM |
| 88 | 210 nM |
| 89 | 840 nM |
| 110 | 746 nM |
| 111 | 205 nM |
| 168 | 435 nM |
| 169 | 900 nM |
| 170 | 430 nM |
| 171 | 440 nM |
| 172 | 485 nM |
| 176 | 435 nM |
| 177 | 725 nM |
| 186 | 360 nM |
| 193 | 870 nM |
| 196 | 270 nM |
| 199 | 450 nM |
| 209 | 565 nM |
| 225 | 789 nM |
| 232 | 505 nM |
| 248 | 705 nM |
| 251 | 100 nM |
| 257 | 860 nM |
| 258 | 630 nM |
| 266 | 780 nM |
| 273 | 870 nM |

It thus appears that the compounds according to the invention have inhibitory activity on MetAP2.

The compounds according to the invention may thus be used for the preparation of medicaments, in particular medicaments for preventing or treating any pathology in which MetAP2 is involved, more particularly those indicated below.

The compounds according to the invention may also be used for preventing or treating any pathology in which MetAP2 is involved, more particularly those indicated below.

Thus, according to another of its aspects, a subject of the invention is medicaments that comprise a compound of formula (I), or an addition salt thereof with a pharmaceutically acceptable acid, or alternatively a hydrate of the compound of formula (I).

Thus, the compounds according to the invention may be used, in man or animals, in the treatment or prevention of pulmonary and hepatic fibrosis.

The compounds according to the invention may also be used in the treatment or prevention of pathologies involving a reactivation of angiogenesis, such as diabetic retinopathy, age-related macular degeneration (ARMD) and psoriasis.

The compounds according to the invention may also be used in the treatment or prevention of any carcinoma having a substantial degree of vascularization, such as lung, breast, prostate, oesophageal, pancreatic, liver, colon or kidney carcinomas or carcinomas that induce metastases, such as colon, breast, liver and stomach carcinomas, and melanomas. These compounds may be used in monotherapy or combination with radiotherapy or chemotherapy.

The compounds according to the invention may also be used in antitumour treatment, alone or in combination with chemotherapy or solid tumours, such as pancreatic, breast, prostate, colon or kidney tumours, neuroblastomas and Kaposi's sarcoma.

The compounds according to the invention may also be used in the treatment or prevention of hepatocarcinomas, cholangiocarcinoma and also malignant mesothelioma, pancreatic cancer, haemoangioma, endometriosis, arthritis and in particular rheumatoid arthritis, autoimmune diseases, obesity and microsporidiosis.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prevention or treatment of the above disorders or diseases.

The appropriate unit administration forms include oral-route forms such as tablets, soft or hard gel capsules, powders, granules and oral solutions or suspensions, sublingual, buccal, intratracheal, intraocular, intranasal or inhalation administration forms, topical, parenteral such as transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| Compound according to the invention | 50.0 mg |
|---|---|
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

The dose of active principle administered per day may range from 0.01 to 100 mg/kg and preferentially 0.02 to 50 mg/kg, in one or more dosage intakes. In general, the daily dose of the compound of the invention will be the lowest effective dose of the compound that is capable of producing a therapeutic effect.

There may be particular cases in which higher or lower dosages are appropriate; such dosages do not depart from the scope of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration, to a patient, of an effective dose of a compound according to the invention, or a pharmaceutically acceptable salt thereof.

The invention claimed is:

1. A compound corresponding to formula (I):

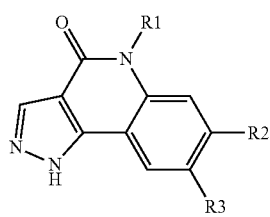
(I)

in which:

R1 represents:
—(C1-C4)alkyl
—(C1-C4) haloalkyl

R 2 represents:
a group:

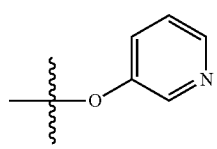

a group:

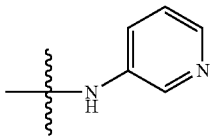 [SMILES: *Nc1cccnc1]

a group: -A -X

R3 represents:
—H
halogen
—(C1-C6)alkyl
a cyano group
—CO$_2$H
—CONH$_2$

A represents:
an aryl or heteroaryl group

X is absent or represents:
halogen
a cyano group
an oxo group
—(CH$_2$)nOH
—(C1-C6)haloalkyl
—(C1-C6)alkyl
—(C1-C6)alkoxy
—(CH2)n-aryl
—CHOH-aryl
heterocycle
heteroaryl
—(C1-C6)alkyl-heterocycle
—(C1-C6)alkyl-heteroaryl
—(C1-C6)alkyl-COORa
—(C1-C6)alkyl-NRaRb
-heteroaryl-(CH2)n-NRaRb
—(CH2)n-NRa—C(O)—Rb
—NRaRb
—NRa—(CH2)n-O—Rb
—NRa-heterocycle
—NRa-aryl
—NRa—C(O)—(CH2)n-NRaRb
—NRa—C(O)-aryl
—NRaC(O)—(C1-C6)alkyl
—NRa—C(O)—(C1-C6)alkyl-aryl
—NRa—C(O)—(CH2)n-O—Rb
—NRa—SO2-(CH2)n-aryl
—NRa—SO2-(CH2)n-NRaRb
—NRa—SO2-Rb
—NRa—SO2-aryl-O-aryl
—NRa—SO2-aryl-(CH2)n-NRb—C(O)—Rb
—COORa
—CONRaRb
—C(O)—NRa—(CH2)n-O—Rb
—C(O)—NRa-aryl-C(O)—NRaRb
—C(O)—NRa—(CH2)n-NRaRb
—C(O)—NRa—(CH2)n-heteroaryl
—O—(CH2)n-NRaRb
—O-heterocycle
—CO-heterocycle
—CO-heteroaryl
—SO2NRaRb
—SO2-heterocycle Ra and Rb represent, independently:
- —H
- —(C1-C6)alkyl n represents 0, 1, 2 or 3 in the form of the base or of an acid-addition salt, and also in hydrate form.

2. The compound according to claim 1, wherein R3 represents H or a halogen, in the form of the base or of an acid-addition salt, and also in hydrate form.

3. The compound according to claim 1, wherein R1 represents an ethyl or a trifluoroethyl; in the form of the base or of an acid-addition salt, and also in hydrate form.

4. The compound according to claim 1, wherein R2 represents a group -A -X with A which represents an aryl or heteroaryl group and X which is absent or represents a heterocycle, NRaRb, (C1-C6)alkyl, a halogen, a cyano group, NRa—SO2-Rb, CO-heterocycle; in the form of the base or of an acid-addition salt, and also in hydrate form.

5. The compound according to claim 1, chosen from the following compounds:

compound 1: 7-(pyrid-2-yl)-5-(2,2,2-trifluoroethyl)-1,5-dihydro-4H-pyrazolo[4,3-c]quinolin-4-one;
compound 2: 7-(2-aminopyrid-3-yl)-5-(2,2,2-trifluoroethyl)-1,5-dihydro-4H-pyrazolo[4,3-c]quinolin-4-one ;
compound 3: 7-(2-fluorophenyl)-5-(2,2,2-trifluoroethyl)-1,5-dihydro-4H-pyrazolo[4,3-c]quinolin-4-one ;
compound 4: 5-ethyl-7-pyrid-2-yl-1,5-dihydro-4H-pyrazolo[4,3-c]quinolin-4-one;
compound 5: 5-ethyl-7-(4-fluorophenyl)-2,5-dihydro-4H-pyrazolo[4,3-c]quinolin-4-one;
compound 6: 7-(pyrid-4-yl)-5-(2,2,2-trifluoroethyl)-1,5-dihydro-4H-pyrazolo[4,3-c]quinolin-4-one;
compound 7: 5-ethyl-7-pyrid-4-yl-1,5-dihydro-4H-pyrazolo[4,3-c]quinolin-4-one;
compound 8: 7-(2-dimethylaminophenyl)-5-ethyl-1,5-dihydro-4H-pyrazolo[4,3-c]quinolin-4-one;
compound 9: N-(3 -dimethylaminopropyl)-4-(5-ethyl-4-oxo-4,5-dihydro-1H-pyrazolo[4,3-c]quinolin-7-yl)benzamide;
compound 10: 5-ethyl-7-(4-piperazin-1-ylphenyl)-1,5-dihydro-4H-pyrazolo[4,3-c]quinolin-4-one;
compound 11: 5-ethyl-7-[4-(4-methylpiperazin-1-yl)phenyl]-1,5-dihydro-4H-pyrazolo[4,3-c]quinolin-4-one;
compound 12: 7-[2-(morpholin-4-ylcarbonyl)phenyl]-5-(2,2,2-trifluoroethyl)-1,5-dihydro-4H-pyrazolo[4,3-c]quinolin-4-one;
compound 13: N-(2-dimethylaminoethyl)-4-(5-ethyl-4-oxo-4,5-dihydro-1H-pyrazolo[4,3-c]quinolin-7-yl)benzamide;
compound 14: 7-(2-morpholin-4-ylphenyl)-5-(2,2,2-trifluoroethyl)-1,5-dihydro-4H-pyrazolo[4,3-c]quinolin-4-one;
compound 15: 7-[4-(1-dimethylaminoethyl)phenyl]-5-ethyl-1,5-dihydro-4H-pyrazolo[4,3-c]quinolin-4-one;
compound 16: 7-(2-morpholin-4-ylmethylphenyl)-5-(2,2,2-trifluoroethyl)-1,5-dihydro-4H-pyrazolo[4,3-c]quinolin-4-one;
compound 17: 5-ethyl-7-(2-morpholin-4-ylmethylphenyl)-1,5-dihydro-4H-pyrazolo[4,3-c]quinolin-4-one;
compound 18: 5-ethyl-7-[4-(piperazine-1-carbonyl)phenyl]-1,5-dihydro-4H-pyrazolo[4,3-c]quinolin-4-one;
compound 19: 7-[4-(4-methylpiperazin-1-yl)phenyl]-5-(2,2,2-trifluoroethyl)-1,5-dihydro-4H-pyrazolo[4,3-c]quinolin-4-one;
compound 20: 5-ethyl-7-(2-piperazin-1-ylpyrimidin-5-yl)-1,5-dihydro-4H-pyrazolo[4,3-c]quinolin-4-one;
compound 21: 5-ethyl-7-[4-(4-methylpiperazine-1-carbonyl)phenyl]-1,5-dihydro-4H-pyrazolo[4,3-c]quinolin-4-one;
compound 22: 5-ethyl-7-[4-(1-pyrrolidin-1-yl-ethyl)phenyl]-1,5-dihydro-4H-pyrazolo[4,3-c]quinolin-4-one;
compound 23: 7-(4-diethylaminophenyl)-5-(2,2,2-trifluoroethyl)-1,5-dihydro-4H-pyrazolo[4,3-c]quinolin-4-one;
compound 24: 7-(4-amino-2-methylphenyl)-5-ethyl-1,5-dihydro-4H-pyrazolo[4,3-c]quinolin-4-one;
compound 25: 7-(4-morpholin-4-ylphenyl)-5-(2,2,2-trifluoroethyl)-1,5-dihydro-4H-pyrazolo[4,3-c]quinolin-4-one
compound 26: 5-ethyl-7-(4-morpholin-4-ylphenyl)-1,5-dihydro-4H-pyrazolo[4,3-c]quinolin-4-one;
compound 27: 5-(5-ethyl-4-oxo-4,5-dihydro-1H-pyrazolo[4,3-c]quinolin-7-yl)-2-fluoro-N-methylbenzamide;
compound 28: 5-ethyl-7-(2-fluoro-5-methoxyphenyl)-1,5-dihydro-4H-pyrazolo[4,3-c]quinolin-4-one;
compound 29: 7-[3-chloro-4-(morpholine-4-carbonyl)phenyl]-5-ethyl-1,5-dihydro-4H-pyrazolo[4,3-c]quinolin-4-one;
compound 30: 7-[4-(piperazin-1-yl)phenyl]-5-(2,2,2-trifluoroethyl)-1,5-dihydro-4H-pyrazolo[4,3-c]quinolin-4-one;
compound 31: 5-ethyl-7-[2-(4-methylpiperazin-1-yl)pyrimidin-5-yl]-1,5-dihydro-4H-pyrazolo[4,3-c]quinolin-4-one;
compound 32: 7-(4-dimethylaminophenyl)-5-(2,2,2-trifluoroethyl)-1,5-dihydro-4H-pyrazolo[4,3-c]quinolin-4-one;
compound 33: 2-chloro-4-(5-ethyl-4-oxo-4,5-dihydro-1H-pyrazolo[4,3-c]quinolin-7-yl)benzamide;
compound 34: 5-ethyl-7-(1H-indazol-5-yl)-1,5-dihydro-4H-pyrazolo[4,3-c]quinolin-4-one;
compound 35: N-ethyl-3-(5-ethyl-4-oxo-4,5-dihydro-1H-pyrazolo[4,3-c]quinolin-7-yl)benzamide;
compound 36: 5-(5-ethyl-4-oxo-4,5-dihydro-1H-pyrazolo[4,3-c]quinolin-7-yl)-2-fluoro-benzamide;
compound 37: N-(2-dimethylaminoethyl)-3 -(5-ethyl-4-oxo-4,5-dihydro-1H-pyrazolo[4,3-c]quinolin-7-yl)benzamide;
compound 38: N-[4-(5-ethyl-4-oxo-4,5-dihydro-1H-pyrazolo[4,3-c]quinolin-7-yl)benzyl]acetamide;
compound 39: 3-(5-ethyl-4-oxo-4,5-dihydro-1H-pyrazolo[4,3-c]quinolin-7-yl)-N-(2-methoxyethyl)benzamide;
compound 40: 7-(3-hydroxyphenyl)-5-(2,2,2-trifluoroethyl)-1,5-dihydro-4H-pyrazolo [4,3-c]quinolin-4-one;
compound 41: 7-(2-chloro-3-fluoropyrid-4-yl)-5-(2,2,2-trifluoroethyl)-1,5-dihydro-4H-pyrazolo[4,3-c]quinolin-4-one;
compound 42: 7-(2-{5-[(propan-2-ylamino)methyl]furan-2-yl}phenyl)-5-(2,2,2-trifluoroethyl)-2,5-dihydro-4H-pyrazolo[4,3-c]quinolin-4-one;
compound 43: N-[2-(5-ethyl-4-oxo-4,5-dihydro-1H-pyrazolo[4,3-c]quinolin-7-yl)phenyl]methanesulfonamide;
compound 44: 7-(2-aminophenyl)-5-ethyl-1,5 -dihydro-4H-pyrazolo[4,3-c]quinolin-4-one;
compound 45: 5-ethyl-7-(3-morpholin-4-ylphenyl)-1,5-dihydro-4H-pyrazolo[4,3-c]quinolin-4-one;
compound 46: N-[2-(5-ethyl-4-oxo-4,5-dihydro-1H-pyrazolo[4,3-c]quinolin-7-yl)phenyl]acetamide;
compound 47: 5-ethyl-7-(2-hydroxyphenyl)-1,5-dihydro-4H-pyrazolo[4,3-c]quinolin-4-one;
compound 48: 5-ethyl-7-[4-(morpholine-4-sulfonyl)phenyl]-1,5-dihydro-4H-pyrazolo[4,3-c]quinolin-4-one;

compound 49: 7-(2-hydroxymethyl-4-methoxyphenyl)-5-(2,2,2-trifluoroethyl)-1,5-dihydro-4H-pyrazolo[4,3-c]quinolin-4-one;
compound 50: 5-ethyl-7-(3-pyrazol-1-ylphenyl)-1,5-dihydro-4H-pyrazolo[4,3-c]quinolin-4-one;
compound 51: 5-ethyl-7-(1H-indol-5-yl)-1,5-dihydro-4H-pyrazolo[4,3-c]quinolin-4-one;
compound 52: 5-(5-ethyl-4-oxo-4,5-dihydro-1H-pyrazolo[4,3-c]quinolin-7-yl)-thiophene-2-carbonitrile;
compound 53: 7-(3-chloro-2-hydroxyphenyl)-5-(2,2,2-trifluoroethyl)-1,5-dihydro-4H-pyrazolo [4,3-c]quinolin-4-one;
compound 54: 5-ethyl-7-(2-hydroxy-3-methoxyphenyl)-1,5-dihydro-4H-pyrazolo[4,3-c]quinolin-4-one;
compound 55: methyl 3-amino-4-[4-oxo-5-(2,2,2-trifluoroethyl)-4,5-dihydro-1H-pyrazolo[4,3-c]quinolin-7-yl]benzoate;
compound 56: 5-ethyl-7-(4-methyl-3,4-dihydro-2H-benzo[1,4]oxazin-7-yl)-1,5-dihydro-4H-pyrazolo [4,3-c]quinolin-4-one;
compound 57: 7-(2,5-dichloropyrid-3-yl)-5-(2,2,2-trifluoroethyl)-1,5-dihydro-4H-pyrazolo[4,3-c]quinolin-4-one;
compound 58: 7-(2-chloro-5-methoxyphenyl)-5-ethyl-1,5-dihydro-4H-pyrazolo[4,3-c]quinolin-4-one;
compound 59: N-(3-dimethylaminopropyl)-3-(5-ethyl-4-oxo-4,5-dihydro-1H-pyrazolo[4,3-c]quinolin-7-yl)benzamide;
compound 60: 5-ethyl-7-(4-fluoro-2-hydroxyphenyl)-1,5-dihydro-4H-pyrazolo[4,3-c]quinolin-4-one;
compound 61: 5-ethyl-7-(2-fluoro-4-methoxyphenyl)-1,5-dihydro-4H-pyrazolo[4,3-c]quinolin-4-one;
compound 62: 7-(4-aminomethylphenyl)-5-ethyl-1,5-dihydro-4H-pyrazolo[4,3-c]quinolin-4-one;
compound 63: 5-ethyl-7-(2-fluoro-3-methoxyphenyl)-1,5-dihydro-4H-pyrazolo[4,3-c]quinolin-4-one;
compound 64: 7-(2-dimethylaminomethylphenyl)-5-ethyl-1,5-dihydro-4H-pyrazolo[4,3-c]quinolin-4-one;
compound 65: 4-(5-ethyl-4-oxo-4,5-dihydro-1H-pyrazolo[4,3-c]quinolin-7-yl)benzoic acid;
compound 66: 7-[6-(piperazin-1-yl)pyrid-3-yl]-5-(2,2,2-trifluoroethyl)-1,5-dihydro-4H-pyrazolo[4,3-c] quinolin-4-one;
compound 67: 5-ethyl-7-[6-(piperazin-1-yl)pyrid-3-yl]-1,5-dihydro-4H-pyrazolo[4,3-c]quinolin-4-one;
compound 68: 7-[2-(4-methylpiperazin-1-yl)pyrid-4-yl]-5-(2,2,2-trifluoroethyl)-1,5-dihydro-4H-pyrazolo[4,3-c]quinolin-4-one;
compound 69: 5-ethyl-7-[2-(4-methylpiperazin-1-yl)pyrid-4-yl]-1,5-dihydro-4H-pyrazolo[4,3-c]quinolin-4-one;
compound 70: 7-[2-(piperazin-1-yl)pyrid-4-yl]-5-(2,2,2-trifluoroethyl)-1,5-dihydro-4H-pyrazolo[4,3-c]quinolin-4-one;
compound 71: 5-ethyl-7-(2-piperazin-1-ylpyrid-4-yl)-1,5-dihydro-4H-pyrazolo[4,3-c]quinolin-4-one;
compound 72: 7-(2-methylpyrid-3-yl)-5-(2,2,2-trifluoroethyl)-1,5-dihydro-4H-pyrazolo[4,3-c]quinolin-4-one;
compound 73: 5-ethyl-7-(2-methylpyrid-3-yl)-1,5-dihydro-4H-pyrazolo[4,3-c]quinolin-4-one;
compound 74: 7-(2-chloro-6-methylpyrid-3-yl)-5-ethyl-1,5-dihydro-4H-pyrazolo[4,3-c]quinolin-4-one;
compound 75: 7-(2-chloro-6-methylpyrid-3-yl)-5-(2,2,2-trifluoroethyl)-1,5-dihydro-4H-pyrazolo[4,3-c]quinolin-4-one;
compound 76: 7-(2-chloropyrid-4-yl)-5-(2,2,2-trifluoroethyl)-1,5-dihydro-4H-pyrazolo[4,3-c]quinolin-4-one;
compound 77: 7-(2-fluoropyrid-3-yl)-5-(2,2,2-trifluoroethyl)-1,5-dihydro-4H-pyrazolo[4,3-c]quinolin-4-one;
compound 78: 5-ethyl-7-(2-fluoropyrid-3-yl)-1,5-dihydro-4H-pyrazolo[4,3-c]quinolin-4-one;
compound 79: 7-(6-chloro-2-methylpyrid-3-yl)-5-(2,2,2-trifluoroethyl)-1,5-dihydro-4H-pyrazolo[4,3-c]quinolin-4-one;
compound 80: 7-(2-methoxypyrid-3-yl)-5-(2,2,2-trifluoroethyl)-2,5-dihydro-4H-pyrazolo[4,3-c]quinolin-4-one;
compound 81: 5-ethyl-7-(2-methoxypyrid-3-yl)-1,5-dihydro-4H-pyrazolo[4,3-c]quinolin-4-one;
compound 82: 7-(6-chloro-4-methylpyrid-3-yl)-5-(2,2,2-trifluoroethyl)-1,5-dihydro-4H-pyrazolo[4,3-c]quinolin-4-one;
compound 83: 7-[6-(morpholin-4-yl)pyrid-3-yl]-5-(2,2,2-trifluoroethyl)-1,5-dihydro-4H-pyrazolo[4,3-c]quinolin-4-one;
compound 84: 7-[6-(3-dimethylaminopropoxy)pyrid-3-yl]-5-ethyl-1,5-dihydro-4H-pyrazolo[4,3-c]quinolin-4-one;
compound 85: 5-ethyl-7-quinolin-8-yl-1,5-dihydro-4H-pyrazolo[4,3-c]quinolin-4-one;
compound 86: 7-(6-chloropyrid-2-yl)-5-(2,2,2-trifluoroethyl)-2,5-dihydro-4H-pyrazolo[4,3-c]quinolin-4-one;
compound 87: 5-ethyl-7-quinolin-6-yl-1,5-dihydro-4H-pyrazolo[4,3-c]quinolin-4-one;
compound 88: 7-(6-chloropyrid-3-yl)-5-(2,2,2-trifluoroethyl)-1,5-dihydro-4H-pyrazolo[4,3-c]quinolin-4-one;
compound 89: 7-(6-chloro-5-methylpyrid-3-yl)-5-(2,2,2-trifluoroethyl)-1,5-dihydro-4H-pyrazolo[4,3-c]quinolin-4-one;
compound 90: 5-ethyl-7-(3-fluoropyrid-4-yl)-1,5-dihydro-4H-pyrazolo[4,3-c] quinolin-4-one;
compound 91: 7-(3-chloropyrid-4-yl)-5-ethyl-1,5-dihydro-4H-pyrazolo[4,3-c]quinolin-4-one;
compound 92: 5-ethyl-7-(6-fluoro-5-methylpyrid-3-yl)-1,5-dihydro-4H-pyrazolo[4,3-c]quinolin-4-one;
compound 93: 7-(2-ethoxypyrid-3-yl)-5-ethyl-1,5-dihydro-4H-pyrazolo[4,3-c]quinolin-4-one;
compound 94: 5-ethyl-7-(5-methoxypyrid-3-yl)-1,5-dihydro-4H-pyrazolo[4,3-c]quinolin-4-one;
compound 95: 7-(6-aminopyrid-3-yl)-5-ethyl-1,5-dihydro-4H-pyrazolo[4,3-c]quinolin-4-one;
compound 96: 5-ethyl-7-pyrid-3-yl-2,5-dihydro-4H-pyrazolo[4,3-c]quinolin-4-one;
compound 97: 7-(2-chloro-6-isopropylpyrid-3-yl)-5-(2,2,2-trifluoroethyl)-1,5-dihydro-4H-pyrazolo[4,3-c]quinolin-4-one;
compound 98: 7-(5-chloro-2-methoxypyrid-4-yl)-5-(2,2,2-trifluoroethyl)-1,5-dihydro-4H-pyrazolo[4,3-c]quinolin-4-one;
compound 99: 7-(pyrid-3-yloxy)-5-(2,2,2-trifluoroethyl)-2,5-dihydro-4H-pyrazolo[4,3-c]quinolin-4-one;
compound 100: 5-ethyl-7-(pyrid-3-yloxy)-2,5-dihydro-4H-pyrazolo[4,3-c]quinolin-4-one;
compound 101: 7-(pyrid-3-ylamino)-5-(2,2,2-trifluoroethyl)-2,5-dihydro-4H-pyrazolo[4,3-c]quinolin-4-one;
compound 102: 5-(2,2-difluoroethyl)-7-pyrid-4-yl-1,5-dihydro-4H-pyrazolo[4,3-c]quinolin-4-one;
compound 103: 5-cyclopropylmethyl-7-pyrid-4-yl-1,5-dihydro-4H-pyrazolo[4,3-c]quinolin-4-one;
compound 104: 5-propyl-7-pyrid-4-yl-1,5-dihydro-4H-pyrazolo[4,3-c]quinolin-4-one;
compound 105: 5-(2,2-difluorocyclopropylmethyl)-7-pyrid-4-yl-1,5-dihydro-4H-pyrazolo[4,3-c]quinolin-4-one;

compound 106: 5-(2-fluoroethyl)-7-pyrid-4-yl-1,5-dihydro-4H-pyrazolo[4,3-c]quinolin-4-one;
compound 107: 5-isopropyl-7-pyrid-4-yl-1,5-dihydro-4H-pyrazolo[4,3-c]quinolin-4-one;
compound 108: 5-cyclopropyl-7-pyrid-4-yl-1,5-dihydro-4H-pyrazolo[4,3-c]quinolin-4-one;
compound 109: 8-fluoro-7-pyrid-2-yl-5-(2,2,2-trifluoroethyl)-1,5-dihydro-4H-pyrazolo[4,3-c]quinolin-4-one;
compound 110: 7-(2-chloropyrid-3-yl)-8-methyl-5-(2,2,2-trifluoroethyl)-1,5-dihydro-4H-pyrazolo[4,3-c]quinolin-4-one;
compound 111: 7-(2-chloropyrid-3-yl)-5-(2,2,2-trifluoroethyl)-1,5-dihydro-4H-pyrazolo[4,3-c]quinolin-4-one;
compound 112: 7-[2-(dimethylamino)phenyl]-5-(2,2,2-trifluoroethyl)-1,5-dihydro-4H-pyrazolo[4,3-c]quinolin-4-one;
compound 113: isopropyl 2-[4-oxo-5-(2,2,2-trifluoroethyl)-4,5-dihydro-1H-pyrazolo[4,3-c]quinolin-7-yl]benzoate;
compound 114: cyclopropanecarboxylic acid {2-[4-oxo-5-(2,2,2-trifluoroethyl)-4,5-dihydro-1H-pyrazolo[4,3-c]quinolin-7-yl]phenyl}amide;
compound 115: 7-[2-(1-methyl-1H-imidazole-2-carbonyl)phenyl]-5-(2,2,2-trifluoroethyl)-1,5-dihydro-4H-pyrazolo[4,3-c]quinolin-4-one;
compound 116: 7-(4-cyclopentylpyrimidin-5-yl)-5-(2,2,2-trifluoroethyl)-1,5-dihydro-4H-pyrazolo[4,3-c]quinolin-4-one;
compound 117: 7-(4-cyclohexylpyrimidin-5-yl)-5-(2,2,2-trifluoroethyl)-1,5-dihydro-4H-pyrazolo[4,3-c]quinolin-4-one;
compound 118: 7-(2-propylaminomethylphenyl)-5-(2,2,2-trifluoroethyl)-1,5-dihydro-4H-pyrazolo[4,3-c]quinolin-4-one;
compound 119: 2-methoxy-N-{2-[4-oxo-5-(2,2,2-trifluoroethyl)-4,5-dihydro-1H-pyrazolo[4,3-c]quinolin-7-yl]phenyl}acetamide;
compound 120: N-{2-[4-oxo-5-(2,2,2-trifluoroethyl)-4,5-dihydro-1H-pyrazolo[4,3-c]quinolin-7-yl]phenyl}isobutyramide;
compound 121: N-{4-methyl-2-[4-oxo-5-(2,2,2-trifluoroethyl)-4,5-dihydro-1H-pyrazolo[4,3-c]quinolin-7-yl]phenyl}propionamide;
compound 122: N-isopropyl-2-[4-oxo-5-(2,2,2-trifluoroethyl)-4,5-dihydro-1H-pyrazolo[4,3-c]quinolin-7-yl]benzamide;
compound 123: 7-[4-methyl-2-(piperidin-4-yloxy)phenyl]-5-(2,2,2-trifluoroethyl)-1,5-dihydro-4H-pyrazolo[4,3-c]quinolin-4-one;
compound 124: 7-[2-(1,4-diazepan-1-ylmethyl)phenyl]-5-(2,2,2-trifluoroethyl)-1,5-dihydro-4H-pyrazolo[4,3-c]quinolin-4-one;
compound 125: ethyl 2-[4-oxo-5-(2,2,2-trifluoroethyl)-4,5-dihydro-1H-pyrazolo[4,3-c]quinolin-7-yl]benzoate;
compound 126: 7-(2-aminophenyl)-5-(2,2,2-trifluoroethyl)-2,5-dihydro-4H-pyrazolo[4,3-c]quinolin-4-one;
compound 127: 7-(2-piperazin-1-ylphenyl)-5-(2,2,2-trifluoroethyl)-2,5-dihydro-4H-pyrazolo[4,3-c]quinolin-4-one;
compound 128: 7-(6-methoxypyrid-3-yl)-5-(2,2,2-trifluoroethyl)-1,5-dihydro-4H-pyrazolo[4,3-c]quinolin-4-one;
compound 129: 7-(5-chloro-2-fluoropyrid-3-yl)-5-(2,2,2-trifluoroethyl)-1,5-dihydro-4H-pyrazolo[4,3-c]quinolin-4-one;
compound 130: N-{5-methyl-3-[4-oxo-5-(2,2,2-trifluoroethyl)-4,5-dihydro-1H-pyrazolo[4,3-c]quinolin-7-yl]pyrid-2-yl}acetamide;
compound 131: 7-[2-(2-hydroxy-ethyl)phenyl]-5-(2,2,2-trifluoroethyl)-1,5-dihydro-4H-pyrazolo[4,3-c]quinolin-4-one;
compound 132: 7-(2-amino-5-fluoropyrid-3-yl)-5-(2,2,2-trifluoroethyl)-1,5-dihydro-4H-pyrazolo[4,3-c]quinolin-4-one;
compound 133: 7-[2-(pyrrolidine-1-sulfonyl)phenyl]-5-(2,2,2-trifluoroethyl)-1,5-dihydro-4H-pyrazolo[4,3-c]quinolin-4-one;
compound 134: N-isopropyl-2-[4-oxo-5-(2,2,2-trifluoroethyl)-4,5-dihydro-1H-pyrazolo[4,3-]quinolin-7-yl]benzene sulfonamide;
compound 135: 7-(2-fluoro-5-methylpyrid-3-yl)-5-(2,2,2-trifluoroethyl)-1,5-dihydro-4H-pyrazolo[4,3-c]quinolin-4-one;
compound 136: N,N-diethyl-2-[4-oxo-5-(2,2,2-trifluoroethyl)-4,5-dihydro-1H-pyrazolo[4,3-c]quinolin-7-yl]benzenesulfonamide;
compound 137: 7-(6-amino-4-methylpyrid-3-yl)-5-(2,2,2-trifluoroethyl)-1,5-dihydro-4H-pyrazolo[4,3-c]quinolin-4-one;
compound 138: 7-(6-methoxy-2-methylpyrid-3-yl)-5-(2,2,2-trifluoroethyl)-1,5-dihydro-4H-pyrazolo[4,3-c]quinolin-4-one;
compound 139: 7-(5-methyl-6-[1,2,4]triazol-4-ylpyrid-3-yl)-5-(2,2,2-trifluoroethyl)-1,5-dihydro-4H-pyrazolo[4,3-c]quinolin-4-one;
compound 140: 7-(4-methyl-6-[1,2,4]triazol-4-ylpyrid-3-yl)-5-(2,2,2-trifluoroethyl)-1,5-dihydro-4H-pyrazolo[4,3-c]quinolin-4-one;
compound 141: 7-[6-(morpholine-4-carbonyl)pyrid-3-yl]-5-(2,2,2-trifluoroethyl)-1,5-dihydro-4H-pyrazolo[4,3-c]quinolin-4-one;
compound 142: 7-(6-amino-2-methylpyrid-3-yl)-5-(2,2,2-trifluoroethyl)-1,5-dihydro-4H-pyrazolo[4,3-c]quinolin-4-one;
compound 143: 7-(4-ethylpyrimidin-5-yl)-5-(2,2,2-trifluoroethyl)-1,5-dihydro-4H-pyrazolo[4,3-c]quinolin-4-one;
compound 144: methyl {2-[4-oxo-5-(2,2,2-trifluoroethyl)-4,5-dihydro-1H-pyrazolo[4,3-c]quinolin-7-yl]phenyl}acetate;
compound 145: 7-(4-methoxypyrid-2-yl)-5-(2,2,2-trifluoroethyl)-1,5-dihydro-4H-pyrazolo[4,3-c]quinolin-4-one;
compound 146: 7-(4-propylpyrimidin-5-yl)-5-(2,2,2-trifluoroethyl)-1,5-dihydro-4H-pyrazolo[4,3-c]quinolin-4-one;
compound 147: N-{6-methyl-5-[4-oxo-5-(2,2,2-trifluoroethyl)-4,5-dihydro-1H-pyrazolo[4,3-c]quinolin-7-yl]pyrid-2-yl}propionamide;
compound 148: 7-(2-oxazol-5-ylphenyl)-5-(2,2,2-trifluoroethyl)-1,5-dihydro-4H-pyrazolo[4,3-c]quinolin-4-one;
compound 149: 7-(4-dimethylamino-2-methoxypyrimidin-5-yl)-5-(2,2,2-trifluoroethyl)-1,5-dihydro-4H-pyrazolo[4,3-c]quinolin-4-one;
compound 150: 7-[2-(5-ethyl-[1,2,4]oxadiazol-3-yl)phenyl]-5-(2,2,2-trifluoroethyl)-1,5-dihydro-4H-pyrazolo[4,3-c]quinolin-4-one;
compound 151: N-{2-[4-oxo-5-(2,2,2-trifluoroethyl)-4,5-dihydro-1H-pyrazolo[4,3-c]quinolin-7-yl]benzyl}acetamide;

compound 152: 7-[5-(hydroxyphenylmethyl)pyrid-2-yl]-5-(2,2,2-trifluoroethyl)-1,5-dihydro-4H-pyrazolo[4,3-c]quinolin-4-one;

compound 153: 6-[4-oxo-5-(2,2,2-trifluoroethyl)-4,5-dihydro-1H-pyrazolo[4,3-c]quinolin-7-yl]pyridine-2-carbonitrile;

compound 154: 7-(6-hydroxymethylpyrid-2-yl)-5-(2,2,2-trifluoroethyl)-1,5-dihydro-4H-pyrazolo[4,3-c]quinolin-4-one;

compound 155: 7-[3-(2-dimethylaminoethoxy)phenyl]-5-(2,2,2-trifluoroethyl)-1,5-dihydro-4H-pyrazolo[4,3-c]quinolin-4-one;

compound 156: methyl 2-[4-oxo-5-(2,2,2-trifluoroethyl)-4,5-dihydro-1H-pyrazolo[4,3-c]quinolin-7-yl]benzoate;

compound 157: 7-(5-hydroxymethylpyrid-2-yl)-5-(2,2,2-trifluoroethyl)-1,5-dihydro-4H-pyrazolo[4,3-c]quinolin-4-one;

compound 158: 7-(2-methoxypyrid-4-yl)-5-(2,2,2-trifluoroethyl)-1,5-dihydro-4H-pyrazolo[4,3-c]quinolin-4-one;

compound 159: 7-(2-[1,2,4]triazol-1-ylmethylphenyl)-5-(2,2,2-trifluoroethyl)-1,5-dihydro-4H-pyrazolo[4,3-c]quinolin-4-one;

compound 160: 7-(4-phenylpyrimidin-5-yl)-5-(2,2,2-trifluoroethyl)-1,5-dihydro-4H-pyrazolo[4,3-c]quinolin-4-one;

compound 161: 7-(6-methoxy-4-methylpyrid-3-yl)-5-(2,2,2-trifluoroethyl)-1,5-dihydro-4H-pyrazolo[4,3-c]quinolin-4-one;

compound 162: 7-(4-isopropylpyrimidin-5-yl)-5-(2,2,2-trifluoroethyl)-1,5-dihydro-4H-pyrazolo[4,3-c]quinolin-4-one;

compound 163: 7-(6-fluoropyrid-2-yl)-5-(2,2,2-trifluoroethyl)-1,5-dihydro-4H-pyrazolo[4,3-c]quinolin-4-one;

compound 164: methyl 6-[4-oxo-5-(2,2,2-trifluoroethyl)-4,5-dihydro-1H-pyrazolo[4,3-c]quinolin-7-yl]pyridine-2-carboxylate;

compound 165: 7-(5-fluoropyrid-2-yl)-5-(2,2,2-trifluoroethyl)-1,5-dihydro-4H-pyrazolo[4,3-c]quinolin-4-one;

compound 166: 7-[2-(4-methylpiperazin-1-yl)pyrid-3-yl]-5-(2,2,2-trifluoroethyl)-1,5-dihydro-4H-pyrazolo[4,3-c]quinolin-4-one;

compound 167: 7-(3-aminopyrid-4-yl)-5-(2,2,2-trifluoroethyl)-1,5-dihydro-4H-pyrazolo[4,3-c]quinolin-4-one;

compound 168: 7-(2,6-dimethylpyrid-4-yl)-5-(2,2,2-trifluoroethyl)-1,5-dihydro-4H-pyrazolo[4,3-c]quinolin-4-one;

compound 169: 7-(3-chloropyrid-2-yl)-5-(2,2,2-trifluoroethyl)-1,5-dihydro-4H-pyrazolo[4,3-c]quinolin-4-one;

compound 170: methyl 3-[4-oxo-5-(2,2,2-trifluoroethyl)-4,5-dihydro-1H-pyrazolo[4,3-c]quinolin-7-yl]pyridine-2-carboxylate;

compound 171: 7-(6-methylpyrid-2-yl)-5-(2,2,2-trifluoroethyl)-1,5-dihydro-4H-pyrazolo[4,3-c]quinolin-4-one;

compound 172: 7-[2-(morpholin-4-yl)pyrid-3-yl]-5-(2,2,2-trifluoroethyl)-1,5-dihydro-4H-pyrazolo[4,3-c]quinolin-4-one;

compound 173: 5-(2,2,2-trifluoroethyl)-7-(2-trifluoromethylpyrid-3-yl)-1,5-dihydro-4H-pyrazolo[4,3-c]quinolin-4-one;

compound 174: 7-(2-cyclopropylaminopyrid-3-yl)-5-(2,2,2-trifluoroethyl)-1,5-dihydro-4H-pyrazolo[4,3-c]quinolin-4-one;

compound 175: 5-(2,2,2-trifluoroethyl)-7-(3-trifluoromethylpyrid-2-yl)-1,5-dihydro-4H-pyrazolo[4,3-c]quinolin-4-one;

compound 176: 3-[4-oxo-5-(2,2,2-trifluoroethyl)-4,5-dihydro-1H-pyrazolo[4,3-c]quinolin-7-yl]pyridine-2-carbonitrile;

compound 177: 2-[4-oxo-5-(2,2,2-trifluoroethyl)-4,5-dihydro-1H-pyrazolo[4,3-c]quinolin-7-yl]pyridine-3-carbonitrile;

compound 178: methyl 2-[4-oxo-5-(2,2,2-trifluoroethyl)-4,5-dihydro-1H-pyrazolo[4,3-c]quinolin-7-yl]nicotinoate;

compound 179: 7-(2-propoxypyrid-3-yl)-5-(2,2,2-trifluoroethyl)-1,5-dihydro-4H-pyrazolo[4,3-c]quinolin-4-one;

compound 180: 7-(3-hydroxypyrid-2-yl)-5-(2,2,2-trifluoroethyl)-1,5-dihydro-4H-pyrazolo[4,3-c]quinolin-4-one;

compound 181: 7-[2-(4-fluorophenylamino)pyrid-3-yl]-5-(2,2,2-trifluoroethyl)-1,5-dihydro-4H-pyrazolo[4,3-c]quinolin-4-one;

compound 182: 7-(2-methylaminophenyl)-5-(2,2,2-trifluoroethyl)-1,5-dihydro-4H-pyrazolo[4,3-c]quinolin-4-one;

compound 183: 7-(2-ethoxypyrid-3-yl)-5-(2,2,2-trifluoroethyl)-1,5-dihydro-4H-pyrazolo[4,3-c]quinolin-4-one;

compound 184: 7-(2-isopropoxypyrid-3-yl)-5-(2,2,2-trifluoroethyl)-1,5-dihydro-4H-pyrazolo[4,3-c]quinolin-4-one;

compound 185: 7-(5-chloro-2-methoxypyrid-3-yl)-5-(2,2,2-trifluoroethyl)-1,5-dihydro-4H-pyrazolo[4,3-c]quinolin-4-one;

compound 186: 7-(2-methylpyrid-4-yl)-5-(2,2,2-trifluoroethyl)-1,5-dihydro-4H-pyrazolo[4,3-c]quinolin-4-one;

compound 187: 7-(4-methylpyrid-2-yl)-5-(2,2,2-trifluoroethyl)-1,5-dihydro-4H-pyrazolo[4,3-c]quinolin-4-one;

compound 188: 7-(6-morpholin-4-ylpyrid-2-yl)-5-(2,2,2-trifluoroethyl)-1,5-dihydro-4H-pyrazolo[4,3-c]quinolin-4-one;

compound 189: 7-(4-methylaminophenyl)-5-(2,2,2-trifluoroethyl)-1,5-dihydro-4H-pyrazolo[4,3-c]quinolin-4-one;

compound 190: 5-(2,2,2-trifluoroethyl)-7-(6-trifluoromethylpyrid-3-yl)-1,5-dihydro-4H-pyrazolo[4,3-c]quinolin-4-one;

compound 191: 7-(6-methoxypyrid-2-yl)-5-(2,2,2-trifluoroethyl)-1,5-dihydro-4H-pyrazolo[4,3-c]quinolin-4-one;

compound 192: 7-[4-(2H-tetrazol-5-yl)phenyl]-5-(2,2,2-trifluoroethyl)-2,5-dihydro-4H-pyrazolo[4,3-c]quinolin-4-one;

compound 193: 7-(3,5-dichloropyrid-2-yl)-5-(2,2,2-trifluoroethyl)-1,5-dihydro-4H-pyrazolo[4,3-c]quinolin-4-one;

compound 194: 8-chloro-7-(pyrid-2-yl)-5-(2,2,2-trifluoroethyl)-1,5-dihydro-4H-pyrazolo[4,3-c]quinolin-4-one;

compound 195 8-bromo-7-pyrid-2-yl-5-(2,2,2-trifluoroethyl)-1,5-dihydro-4H-pyrazolo[4,3-c]quinolin-4-one;

compound 196: 8-chloro-7-(pyrid-4-yl)-5-(2,2,2-trifluoroethyl)-1,5-dihydro-4H-pyrazolo[4,3-c]quinolin-4-one;

compound 197: 8-bromo-7-(pyrid-4-yl)-5-(2,2,2-trifluoroethyl)-2,5-dihydro-4H-pyrazolo[4,3-c]quinolin-4-one;

compound 198: 8-chloro-5-ethyl-7-pyrid-4-yl-1,5-dihydro-4H-pyrazolo[4,3-c]quinolin-4-one;

compound 199: 8-chloro-7-(2-chloropyrid-3-yl)-5-(2,2,2-trifluoroethyl)-1,5-dihydro-4H-pyrazolo[4,3-c]quinolin-4-one;

compound 200: 8-methyl-7-pyrid-2-yl-5-(2,2,2-trifluoroethyl)-1,5-dihydro-4H-pyrazolo[4,3-c]quinolin-4-one;

compound 201: 4-oxo-7-pyrid-4-yl-5-(2,2,2-trifluoroethyl)-4,5-dihydro -2H,4H-pyrazolo[4,3-c]quinoline-8-carbonitrile;

compound 202: 4-oxo-7-pyrid-4-yl-5-(2,2,2-trifluoroethyl)-4,5-dihydro-2H,4H-pyrazolo[4,3-c]quinoline-8-carboxylic acid;

compound 203: 3-[4-oxo-5-(2,2,2-trifluoroethyl)-4,5-dihydro-1H-pyrazolo[4,3-c]quinolin-7-yl]pyridine-2-carboxylic acid;

compound 204: 2-[4-oxo-5-(2,2,2-trifluoroethyl)-4,5-dihydro-1H-pyrazolo[4,3-c]quinolin-7-yl]benzoic acid;

compound 205: 4-oxo-7-(pyrid-4-yl)-5-(2,2,2-trifluoroethyl)-4,5-dihydro-2H-pyrazolo[4,3-c]quinoline-8-carboxamide;

compound 206: 7-[2-(morpholin-4-ylcarbonyl)pyrid-3-yl]-5-(2,2,2-trifluoroethyl)-1,5-dihydro-4H-pyrazolo[4,3-c]quinolin-4-one;

compound 207: N-[2-(dimethylamino)ethyl]-N-methyl-2-[4-oxo-5-(2,2,2-trifluoroethyl)-4,5-dihydro-1H-pyrazolo[4,3-c]quinolin-7-yl]benzamide;

compound 208: N-(2-dimethylaminoethyl)-N-ethyl-2-[4-oxo-5-(2,2,2-trifluoroethyl)-4,5-dihydro-1H-pyrazolo[4,3-c]quinolin-7-yl]benzamide;

compound 209: 7-{2-[(4-methyl-1,4-diazepan-1-yl)carbonyl]phenyl}-5-(2,2,2-trifluoroethyl)-1,5-dihydro-4H-pyrazolo[4,3-c]quinolin-4-one;

compound 210: 7-{2-[(4-methylpiperazin-1-yl)carbonyl]phenyl}-5-(2,2,2-trifluoroethyl)-1,5-dihydro-4H-4H-pyrazolo[4,3-c]quinolin-4-one;

compound 211: N-(3-carbamoylphenyl)-2-[4-oxo-5-(2,2,2-trifluoroethyl)-4,5-dihydro-1H-pyrazolo[4,3-c]quinolin-7-yl]benzamide;

compound 212: N-(3-dimethylaminopropyl)-2-[4-oxo-5-(2,2,2-trifluoroethyl)-4,5-dihydro-1H-pyrazolo[4,3-c]quinolin-7-yl]benzamide;

compound 213: N,N-dimethyl-3-[4-oxo-5-(2,2,2-trifluoroethyl)-4,5-dihydro-1H-pyrazolo[4,3-c]quinolin-7-yl]pyridine-2-carboxamide;

compound 214: 2-[4-oxo-5-(2,2,2-trifluoroethyl)-4,5-dihydro-1H-pyrazolo[4,3-c]quinolin-7-yl]-N-[2-(pyrid-4-yl)ethyl]benzamide;

compound 215: N-[2-(dimethylamino)ethyl]-N-methyl-3-[4-oxo-5-(2,2,2-trifluoroethyl)-4,5-dihydro-1H-pyrazolo[4,3-c]quinolin-7-yl]pyridine-2-carboxamide;

compound 216: 7-[2-(1,4-oxazepan-4-ylcarbonyl)pyrid-3-yl]-5-(2,2,2-trifluoroethyl)-1,5-dihydro-4H-pyrazolo[4,3-c]quinolin-4-one;

compound 217: N-methyl-3-[4-oxo-5-(2,2,2-trifluoroethyl)-4,5-dihydro-1H-pyrazolo[4,3-c]quinolin-7-yl]pyridine-2-carboxamide;

compound 218: 2-[4-oxo-5-(2,2,2-trifluoroethyl)-4,5-dihydro-1H-pyrazolo[4,3-c]quinolin-7-yl]-N-(pyrid-3-ylmethyl)benzamide;

compound 219: N-ethyl-2-[4-oxo-5-(2,2,2-trifluoroethyl)-4,5-dihydro-1H-pyrazolo[4,3-c]quinolin-7-yl]-N-(pyrid-4-ylmethyl)benzamide;

compound 220: 3-[4-oxo-5-(2,2,2-trifluoroethyl)-4,5 -dihydro-1H-pyrazolo[4,3-c]quinolin-7-yl]pyridine-2-carboxamide;

compound 221: N-[2-(dimethylamino)ethyl]-N-ethyl-3-[4-oxo-5-(2,2,2-trifluoroethyl)-4,5-dihydro-1H-pyrazolo[4,3-c]quinolin-7-yl]pyridine-2-carboxamide;

compound 222: 7-[2-((2S,6R)-2,6-dimethylmorpholine-4-carbonyl)pyrid-3-yl]-5-(2,2,2-trifluoroethyl)-1,5-dihydro-4H-pyrazolo[4,3-c]quinolin-4-one;

compound 223: N-{3-[4-oxo-5-(2,2,2-trifluoroethyl)-4,5-dihydro-1H-pyrazolo[4,3-c]quinolin-7-yl]pyrid-2-yl}acetamide;

compound 224: 3-dimethylamino-N-{2-[4-oxo-5-(2,2,2-trifluoroethyl)-4,5-dihydro-2H,4H-pyrazolo[4,3-c]quinolin-7-yl]phenyl}propionamide;

compound 225: 4-(dimethylamino)-N-{2-[4-oxo-5-(2,2,2-trifluoroethyl)-4,5-dihydro-1H-pyrazolo[4,3-c]quinolin-7-yl]phenyl}butanamide;

compound 226: N-{4-[4-oxo-5-(2,2,2-trifluoroethyl)-4,5-dihydro-1H-pyrazolo[4,3-c]quinolin-7-yl]pyrid-3-yl}acetamide;

compound 227: N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 228: 2-methoxy-N-{4-[4-oxo-5-(2,2,2-trifluoroethyl)-4,5-dihydro-1H-pyrazolo[4,3-c]quinolin-7-yl]pyrid-3-yl}-2-phenylacetamide;

compound 229: N-{4-[4-oxo-5-(2,2,2-trifluoroethyl)-4,5-dihydro-1H-pyrazolo[4,3-c]quinolin-7-yl]pyrid-3-yl}-2-phenylpropionamide;

compound 230: 2-(3-chlorophenyl)-N-{4-[4-oxo-5-(2,2,2-trifluoroethyl)-4,5-dihydro-1H-pyrazolo[4,3-c]quinolin-7-yl]pyrid-3-yl}acetamide;

compound 231: 2-(2,4-dichlorophenyl)-N-{4-[4-oxo-5-(2,2,2-trifluoroethyl)-4,5-dihydro-1H-pyrazolo[4,3-c]quinolin-7-yl]pyrid-3-yl}acetamide;

compound 232: N-{2-[4-oxo-5-(2,2,2-trifluoroethyl)-4,5-dihydro-2H-pyrazolo[4,3-c]quinolin-7-yl]phenyl}methanesulfonamide;

compound 233: 2-(dimethylamino)-N-{2-[4-oxo-5-(2,2,2-trifluoroethyl)-4,5-dihydro-1H-pyrazolo[4,3-c]quinolin-7-yl]phenyl } ethanesulfonamide;

compound 234: N-{2-[4-oxo-5-(2,2,2-trifluoroethyl)-4,5-dihydro-1H-pyrazolo[4,3-c]quinolin-7-yl]phenyl}-1-phenylmethanesulfonamide;

compound 235: 3-chloro-N-{2-[4-oxo-5-(2,2,2-trifluoroethyl)-4,5-dihydro-1H-pyrazolo[4,3-c]quinolin-7-yl]phenyl }benzene sulfonamide;

compound 236: N-{4-[4-oxo-5-(2,2,2-trifluoroethyl)-4,5-dihydro-1H-pyrazolo[4,3-c]quinolin-7-yl]pyrid-3-yl}methanesulfonamide;

compound 237: N-{4-[4-oxo-5-(2,2,2-trifluoroethyl)-4,5-dihydro-1H-pyrazolo[4,3-c]quinolin-7-yl]pyrid-3-yl}-1 -phenylmethanesulfonamide;

compound 238: 3-chloro-N-{4-[4-oxo-5-(2,2,2-trifluoroethyl)-4,5-dihydro-1H-pyrazolo[4,3-c]quinolin-7-yl]pyrid-3-yl }benzenesulfonamide;

compound 239: N-(4-methoxy-3-{4-[4-oxo-5-(2,2,2-trifluoroethyl)-4,5-dihydro-1H-pyrazolo[4,3-c]quinolin-7-yl]pyrid-3-ylsulfamoyl }benzyl)acetamide;

compound 240: N-{4-[4-oxo-5-(2,2,2-trifluoroethyl)-4,5-dihydro-1H-pyrazolo[4,3-c]quinolin-7-yl]pyrid-3-yl}-2-phenoxybenzenesulfonamide;

compound 241: N-methyl-N-{3-[4-oxo-5-(2,2,2-trifluoroethyl)-4,5-dihydro-1H-pyrazolo[4,3-c]quinolin-7-yl]pyrid-2-yl}acetamide;

compound 242: N-methyl-N-{3-[4-oxo-5-(2,2,2-trifluoroethyl)-4,5-dihydro-1H-pyrazolo[4,3-c]quinolin-7-yl]pyrid-2-yl}cyclopropanecarboxamide;

compound 243: 7-[2-(methylamino)pyrid-3-yl]-5-(2,2,2-trifluoroethyl)-1,5-dihydro-4H-pyrazolo[4,3-c]quinolin-4-one;

compound 244: 7-[2-(1,4-diazepan-1-yl)pyrid-3-yl]-5-(2,2,2-trifluoroethyl)-1,5-dihydro-4H-pyrazolo[4,3-c]quinolin-4-one;

compound 245: 7-(3,4,5,6-tetrahydro-2H-[1,2']bipyridinyl-3'-yl)-5-(2,2,2-trifluoroethyl)-2,5-dihydro-4H-pyrazolo[4,3-c]quinolin-4-one;

compound 246: 7-[2-(3-hydroxypyrrolidin-1-yl)pyrid-3-yl]-5-(2,2,2-trifluoroethyl)-1,5-dihydro-4H-pyrazolo[4,3-c]quinolin-4-one;

compound 247: 7-[2-(3,4-dihydroxypyrrolidin-1-yl)pyrid-3-yl]-5-(2,2,2-trifluoroethyl)-2,5-dihydro-4H-pyrazolo[4,3-c]quinolin-4-one;

compound 248: 7-[2-(dimethylamino)pyrid-3-yl]-5-(2,2,2-trifluoroethyl)-1,5-dihydro-4H-pyrazolo[4,3-c]quinolin-4-one;

compound 249: 7-{2-[ethyl(methyl)amino]pyrid-3-yl}-5-(2,2,2-trifluoroethyl)-1,5-dihydro-4H-pyrazolo[4,3-c]quinolin-4-one;

compound 250: 7-{2-[(2-hydroxyethyl)(methyl)amino]pyrid-3-yl}-5-(2,2,2-trifluoroethyl)-1,5-dihydro-4H-pyrazolo[4,3-c]quinolin-4-one;

compound 251: 7-[2-(pyrrolidin-1-yl)pyrid-3-yl]-5-(2,2,2-trifluoroethyl)-1,5-dihydro-4H-pyrazolo[4,3-c]quinolin-4-one;

compound 252: 7-[2-(1,4-oxazepan-4-yl)pyrid-3-yl]-5-(2,2,2-trifluoroethyl)-1,5-dihydro-4H-pyrazolo[4,3-c]quinolin-4-one;

compound 253: 7-[2-(3-oxopiperazin-1-yl)pyrid-3-yl]-5-(2,2,2-trifluoroethyl)-1,5-dihydro-4H-pyrazolo[4,3-c]quinolin-4-one;

compound 254: 7-[2-(azetidin-1-yl)pyrid-3-yl]-5-(2,2,2-trifluoroethyl)-1,5-dihydro-4H-pyrazolo[4,3-c]quinolin-4-one;

compound 255: 7-{2-[(2-methoxyethyl)methylamino]pyrid-3-yl}5-(2,2,2-trifluoroethyl)-2,5-dihydro-4H-pyrazolo[4,3-c]quinolin-4-one;

compound 256: 7-[2-(4-acetylpiperazin-1-yl)pyrid-3-yl]-5-(2,2,2-trifluoroethyl)-2,5-dihydro-4H-pyrazolo[4,3-c]quinolin-4-one;

compound 257: 7-[2-(diethylamino)pyrid-3-yl]-5-(2,2,2-trifluoroethyl)-1,5-dihydro-4H-pyrazolo[4,3-c]quinolin-4-one;

compound 258: 7-[2-(cyclobutylamino)pyrid-3-yl]-5-(2,2,2-trifluoroethyl)-1,5-dihydro-4H-pyrazolo[4,3-c]quinolin-4-one;

compound 259: 7-[2-(2,6-dimethylmorpholin-4-yl)pyrid-3-yl]-5-(2,2,2-trifluoroethyl)-2,5-dihydro-4H-pyrazolo[4,3-c]quinolin-4-one;

compound 260: 7-[2-(4-cyclopropylpiperazin-1-yl)pyrid-4-yl]-5-(2,2,2-trifluoroethyl)-2,5-dihydro-4H-pyrazolo[4,3-c]quinolin-4-one;

compound 261: 7-(2-cyclohexylaminopyrid-3-yl)-5-(2,2,2-trifluoroethyl)-2,5-dihydro-4H-pyrazolo[4,3-c]quinolin-4-one;

compound 262: 7-[2-(isopropylmethylamino)pyrid-3-yl]-5-(2,2,2-trifluoroethyl)-2,5-dihydro-4H-pyrazolo[4,3-c]quinolin-4-one;

compound 263: 7-(2-cyclopentylaminopyrid-3-yl)-5-(2,2,2-trifluoroethyl)-2,5-dihydro-4H-pyrazolo[4,3-c]quinolin-4-one;

compound 264: 7-(6-pyrrolidin-1-ylpyrid-2-yl)-5-(2,2,2-trifluoroethyl)-2,5-dihydro-4H-pyrazolo[4,3-c]quinolin-4-one;

compound 265: 7-[6-(2,6-dimethylmorpholin-4-yl)pyrid-2-yl]-5-(2,2,2-trifluoroethyl)-2,5-dihydro-4H-pyrazolo[4,3-c]quinolin-4-one;

compound 266: 7-{2-[cyclohexyl(methyl)amino]pyrid-3-yl}-5-(2,2,2-trifluoroethyl)-1,5-dihydro-4H-pyrazolo[4,3-c]quinolin-4-one;

compound 267: 7-[2-(4-cyclopropylpiperazin-1-yl)pyrid-3-yl]-5-(2,2,2-trifluoroethyl)-2,5-dihydro-4H-pyrazolo[4,3-c]quinolin-4-one;

compound 268: 7-[3-(4-cyclopropylpiperazin-1-yl)phenyl]-5-(2,2,2-trifluoroethyl)-1,5-dihydro-4H-pyrazolo[4,3-c]quinolin-4-one;

compound 269: 7-[2-(4-acetyl-1,4-diazepan-1-yl)pyrid-3-yl]-5-(2,2,2-trifluoroethyl)-1,5-dihydro-4H-pyrazolo[4,3-c]quinolin-4-one;

compound 270: 7-[2-(4-methyl-1,4-diazepan-1-yl)pyrid-3-yl]-5-(2,2,2-trifluoroethyl)-1,5-dihydro-4H-pyrazolo[4,3-c]quinolin-4-one;

compound 271: 7-[2-(4-cyclopropyl-[1,4]diazepan-1-yl)pyrid-3-yl]-5-(2,2,2-trifluoroethyl)-2,5-dihydro-4H-pyrazolo[4,3-c]quinolin-4-one;

compound 272: 7-[2-(3-fluoropyrrolidin-1-yl)pyrid-3-yl]-5-(2,2,2-trifluoroethyl)-2,5-dihydro-4H-pyrazolo[4,3-c]quinolin-4-one;

compound 273: 7-[2-(4-fluoropiperidin-1-yl)pyrid-3-yl]-5-(2,2,2-trifluoroethyl)-1,5-dihydro-4H-pyrazolo[4,3-c]quinolin-4-one;

compound 274: 7-(2-hydroxypyrid-3-yl)-5-(2,2,2-trifluoroethyl)-1,5-dihydro-4H-pyrazolo[4,3-c]quinolin-4-one;

compound 275: 7-(1-oxypyrid-2-yl)-5-(2,2,2-trifluoroethyl)-1,5-dihydro-4H-pyrazolo[4,3-c]quinolin-4-one;

compound 276: 7-(1-oxypyrid-4-yl)-5-(2,2,2-trifluoroethyl)-1,5-dihydro-4H-pyrazolo[4,3-c]quinolin-4-one;

in the form of the base or of an acid-addition salt, and also in hydrate form.

6. A compound of formula (V)

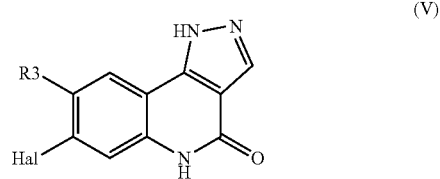

in which R3 represents hydrogen, halogen, —($C_1$-$C_6$) alkyl, a cyano group, —$CO_2$H or —$COH_2$ and Hal represents a halogen atom; in the form of the base or of an acid-addition salt, and also in hydrate form.

7. A compound of formula (VI); (VII); or (VIII)

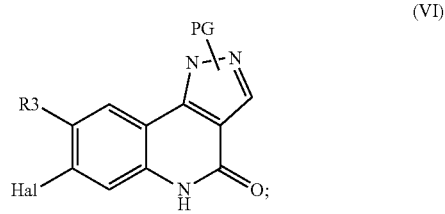

-continued

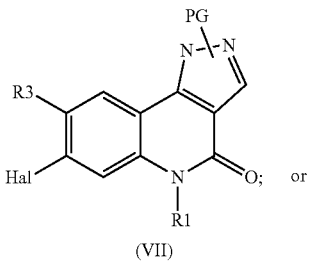
(VII)

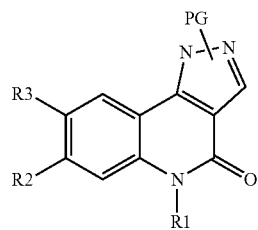
(VIII)

in which R1 represents —($C_1$-$C_4$)alkyl or —($C_1$-$C_4$)haloalkyl, R2 represents
a group:

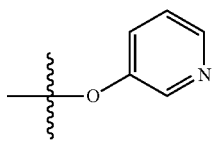

a group:

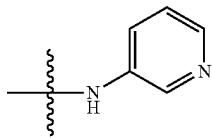

a group: -A -X
A represents:
   an aryl or heteroaryl group
X is absent or represents:
   halogen
   a cyano group
   an oxo group
   —($CH_2$)nOH
   —(C1-C6)haloalkyl
   —(C1-C6)alkyl
   —(C1-C6)alkoxy
   —(CH2)n-aryl
   —CHOH-aryl
   heterocycle
   heteroaryl
   —(C1-C6)alkyl-heterocycle
   —(C1-C6)alkyl-heteroaryl
   —(C1-C6)alkyl-COORa
   —(C1-C6)alkyl-NRaRb
   —heteroaryl-(CH2)n-NRaRb
   —(CH2)n-NRa—C(O)—Rb
   —NRaRb
   —NRa—(CH2)n-O—Rb
   —NRa-heterocycle
   —NRa-aryl
   —NRa—C(O)—(CH2)n-NRaRb
   —NRa—C(O)-aryl
   —NRaC(O)—(C1-C6)alkyl
   —NRa—C(O)—(C1-C6)alkyl-aryl
   —NRa—C(O)—(CH2)n-O—Rb
   —NRa—SO2-(CH2)n-aryl
   —NRa—SO2-(CH2)n-NRaRb
   —NRa—SO2-Rb
   —NRa—SO2-aryl-O-aryl
   —NRa—SO2-aryl-(CH2)n-NRb—C(O)—Rb
   —COORa
   —CONRaRb
   —C(O)—NRa—(CH2)n-O—Rb
   —C(O)—NRa-aryl-C(O)—NRaRb
   —C(O)—NRa—(CH2)n-NRaRb
   —C(O)—NRa—(CH2)n-heteroaryl
   —O—(CH2)n-NRaRb
   —O-heterocycle
   —CO-heterocycle
   —CO-heteroaryl
   —SO2NRaRb
   —SO2-heterocycle R3 represents hydrogen, halogen, —($C_1$-$C_6$)alkyl, a cyano group, —$CO_2H$ or —$COH_2$ and Hal represents a halogen atom and PG represents 2-(trimethylsilyl)ethoxymethyl (SEM) or tetrahydropyranyl (THP); in the form of the base or of an acid-addition salt, and also in hydrate form.

8. A compound of formula (IX):

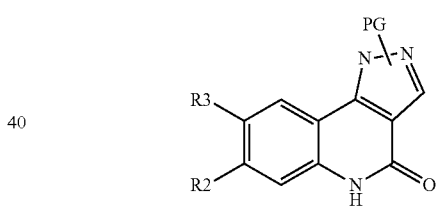
(IX)

in which R2 represents a group:

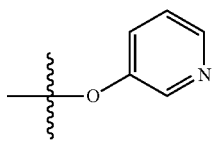

a group:

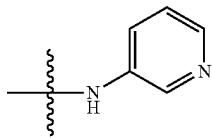

a group: -A -X
A represents:
   an aryl or heteroaryl group

X is absent or represents:
  halogen
  a cyano group
  an oxo group
  —(CH$_2$)nOH
  —(C1-C6)haloalkyl
  —(C1-C6)alkyl
  —(C1-C6)alkoxy
  —(CH2)n-aryl
  —CHOH-aryl
  heterocycle
  heteroaryl
  —(C1-C6)alkyl-heterocycle
  —(C1-C6)alkyl-heteroaryl
  —(C1-C6)alkyl-COORa
  —(C1-C6)alkyl-NRaRb
  —heteroaryl-(CH2)n-NRaRb
  —(CH2)n-NRa—C(O)—Rb
  —NRaRb
  —NRa—(CH2)n-O—Rb
  —NRa-heterocycle
  —NRa-aryl
  —NRa—C(O)—(CH2)n-NRaRb
  —NRa—C(O)-aryl
  —NRaC(O)—(C1-C6)alkyl
  —NRa—C(O)—(C1-C6)alkyl-aryl
  —NRa—C(O)—(CH2)n-O—Rb
  —NRa—SO2-(CH2)n-aryl
  —NRa—SO2-(CH2)n-NRaRb
  —NRa—SO2-Rb
  —NRa—SO2-aryl-O-aryl
  —NRa—SO2-aryl-(CH2)n-NRb—C(O)—Rb
  —COORa
  —CONRaRb
  —C(O)—NRa—(CH2)n-O—Rb
  —C(O)—NRa-aryl-C(O)—NRaRb
  —C(O)—NRa—(CH2)n-NRaRb
  —C(O)—NRa—(CH2)n-heteroaryl
  —O—(CH2)n-NRaRb
  —O-heterocycle
  —CO-heterocycle
  —CO-heteroaryl
  —SO2NRaRb
  —SO2-heterocycle
R3 represents —H, a halogen, —(C1-C6)alkyl, a cyano group or —CONH$_2$ and PG represents 2-(trimethylsilyl) ethoxymethyl (SEM) or tetrahydropyranyl (THP); in the form of the base or of an acid-addition salt, and also in hydrate form.

9. A compound of formula (XIV):

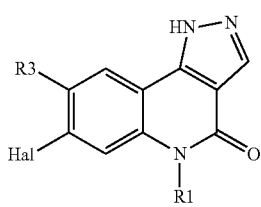

(XIV)

in which R1 represents represents
  —(C1-C4)alkyl
  —(C1-C4)haloalkyl and R3 represents
  —H
  halogen
  —(C1-C6)alkyl
  a cyano group
  —CO$_2$H
  —CONH$_2$
and Hal represents a halogen atom; in the form of the base or of an acid-addition salt, and also in hydrate form.

10. A compound of formula (XIX) or (XX)

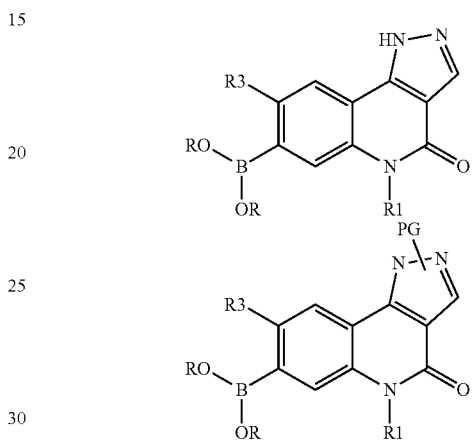

in which R1 represents
  —(C1-C4)alkyl
  —(C1-C4)haloalkyl
and R3 represents
  —H
  halogen
  —(C1 -C6)alkyl
  a cyano group
  —CO$_2$H
  —CONH$_2$ and R represents a hydrogen atom or both the groups R are carbon atoms bonded together and optionally substituted with one or more groups (C1-C4) alkyl and PG represents a 2-(trimethylsilyl)ethoxymethyl (SEM) or tetrahydropyranyl (THP); in the form of the base or of an acid-addition salt, and also in hydrate form.

11. A pharmaceutical composition comprising the compound of claim 1, in the form of the base or of an acid-addition salt, and also in hydrate form.

12. The pharmaceutical composition of claim 11 further comprising at least one pharmaceutically acceptable excipient.

13. The compound of claim 2 wherein said halogen is chlorine.

14. The compound of claim 4 wherein said halogen is chlorine or fluorine.

* * * * *